(12) United States Patent
Patel et al.

(10) Patent No.: US 12,268,359 B2
(45) Date of Patent: Apr. 8, 2025

(54) HANDHELD UNIT FOR ENDOSCOPY, LAPAROSCOPY, AND OTHER SCOPIC PROCEDURES AND METHODS OF MANUFACTURE AND USE THEREOF

(71) Applicant: Endoluxe Inc., Dunwoody, GA (US)

(72) Inventors: Neal Patel, Atlanta, GA (US); Philip Zhao, New York, NY (US); Scott Dentino, Asbury Park, NJ (US)

(73) Assignee: Endoluxe Inc., Allentown, PA (US)

( * ) Notice: Subject to any disclaimer, the term of this patent is extended or adjusted under 35 U.S.C. 154(b) by 0 days.

(21) Appl. No.: 18/603,867

(22) Filed: Mar. 13, 2024

(65) Prior Publication Data

US 2024/0341572 A1   Oct. 17, 2024

Related U.S. Application Data

(60) Provisional application No. 63/451,829, filed on Mar. 13, 2023.

(51) Int. Cl.
*A61B 1/00* (2006.01)
*A61B 1/018* (2006.01)
(Continued)

(52) U.S. Cl.
CPC ...... *A61B 1/00108* (2013.01); *A61B 1/00016* (2013.01); *A61B 1/00032* (2013.01); *A61B 1/0004* (2022.02); *A61B 1/00066* (2013.01); *A61B 1/00091* (2013.01); *A61B 1/00097* (2022.02); *A61B 1/00101* (2013.01); *A61B 1/00103* (2013.01); *A61B 1/00105* (2013.01); *A61B 1/00124* (2013.01);
(Continued)

(58) Field of Classification Search
None
See application file for complete search history.

(56) References Cited

U.S. PATENT DOCUMENTS 5,523,782 A * 6/1996 Williams ........... A61B 1/00188
348/E5.025
6,135,947 A * 10/2000 Watanabe ............ A61B 1/0669
600/178
(Continued)

FOREIGN PATENT DOCUMENTS

JP           6305899      4/2018
JP        2021521989      8/2021

*Primary Examiner* — John P Leubecker
(74) *Attorney, Agent, or Firm* — Dentons US LLP

(57) ABSTRACT

This disclosure enables various technologies for endoscopy, laparoscopy, and other endoscopic or scopic procedures and methods of manufacture and use thereof. One of such technologies includes a handheld unit and a computing terminal. The handheld unit has a handle, an energy store, a scope, and a first wireless communication interface. The handle has a channel. The energy store has a body and a tower extending radially from the body. The tower hosts a control panel for the scope. The tower extends within the channel when the energy store is assembled with the handle by a user. The computing terminal hosts a second wireless communication interface, where the second wireless communication interface receives an imagery of a cavity captured via the scope powered by the energy store when the scope extends within the cavity as the user holds the handle outside the cavity.

30 Claims, 31 Drawing Sheets

(51) Int. Cl.
*A61B 1/05* (2006.01)
*A61B 1/06* (2006.01)

(52) U.S. Cl.
CPC .............. *A61B 1/018* (2013.01); *A61B 1/051* (2013.01); *A61B 1/0676* (2013.01)

(56) References Cited

U.S. PATENT DOCUMENTS

| | | | |
|---|---|---|---|
| 10,130,244 B2 | 11/2018 | Patel et al. | |
| 10,420,916 B1* | 9/2019 | Nelson | A61B 1/00082 |
| 10,772,488 B2 | 9/2020 | Zhao et al. | |
| 11,478,140 B1 | 10/2022 | Street et al. | |
| 2002/0163578 A1* | 11/2002 | Adair | A61B 1/00016 348/E5.026 |
| 2004/0252188 A1* | 12/2004 | Stantchev | A61B 1/0676 348/E7.087 |
| 2005/0085690 A1* | 4/2005 | Tien | A61B 1/00105 348/E7.087 |
| 2007/0060789 A1* | 3/2007 | Uchimura | A61B 1/00105 600/110 |
| 2007/0162095 A1* | 7/2007 | Kimmel | A61B 1/042 600/172 |
| 2007/0225556 A1* | 9/2007 | Ortiz | A61B 1/0684 600/172 |
| 2008/0195128 A1* | 8/2008 | Orbay | A61B 1/00048 600/183 |
| 2009/0225159 A1* | 9/2009 | Schneider | A61B 1/00034 348/82 |
| 2009/0287192 A1* | 11/2009 | Vivenzio | A61B 1/00105 606/1 |
| 2010/0145146 A1* | 6/2010 | Melder | A61B 1/00052 600/112 |
| 2011/0009694 A1 | 1/2011 | Schultz et al. | |
| 2011/0257481 A1 | 10/2011 | Ogawa et al. | |
| 2011/0275895 A1* | 11/2011 | MacKin | A61M 16/04 600/112 |
| 2012/0289858 A1* | 11/2012 | Ouyang | A61B 1/00101 600/562 |
| 2013/0123577 A1* | 5/2013 | Ho | A61B 8/12 600/109 |
| 2014/0107416 A1* | 4/2014 | Birnkrant | A61B 1/00124 600/110 |
| 2014/0275763 A1* | 9/2014 | King | A61B 1/00105 600/110 |
| 2015/0057952 A1* | 2/2015 | Coombs | G01N 29/04 702/38 |
| 2015/0293877 A1* | 10/2015 | Liang | A61B 1/00016 710/33 |
| 2015/0313446 A1* | 11/2015 | Ogawa | A61B 1/00009 600/117 |
| 2017/0105603 A1* | 4/2017 | Hosaka | A61B 1/00052 |
| 2017/0127909 A1* | 5/2017 | Prendergast | A61B 1/00009 |
| 2017/0188795 A1* | 7/2017 | Ouyang | A61B 1/015 |
| 2018/0132700 A1* | 5/2018 | Ouyang | A61B 1/00052 |
| 2018/0326144 A1* | 11/2018 | Truckai | A61B 18/1485 |
| 2019/0159662 A1* | 5/2019 | Papas | A61B 1/00032 |
| 2019/0298159 A1* | 10/2019 | Kimura | A61B 1/00002 |
| 2019/0328217 A1* | 10/2019 | Moreau | A61B 1/00174 |
| 2019/0357758 A1* | 11/2019 | Malinskiy | A61B 1/0669 |
| 2020/0196836 A1 | 6/2020 | De Jong et al. | |
| 2020/0305688 A1* | 10/2020 | Sharp | A61B 1/00128 |
| 2020/0397224 A1 | 12/2020 | Mirza et al. | |
| 2021/0038053 A1* | 2/2021 | Lesch | H04N 23/54 |
| 2021/0161555 A1 | 6/2021 | Winegar et al. | |
| 2021/0244265 A1* | 8/2021 | Chou | A61B 1/00121 |
| 2022/0047153 A1* | 2/2022 | Hedges | A61B 1/0607 |
| 2022/0395160 A1* | 12/2022 | Salman | A61B 1/0669 |
| 2023/0329525 A1* | 10/2023 | OuYang | A61B 1/00032 |
| 2024/0122449 A1* | 4/2024 | Sharma | A61B 1/0684 |
| 2024/0277214 A1* | 8/2024 | Sharp | A61B 1/00142 |

* cited by examiner

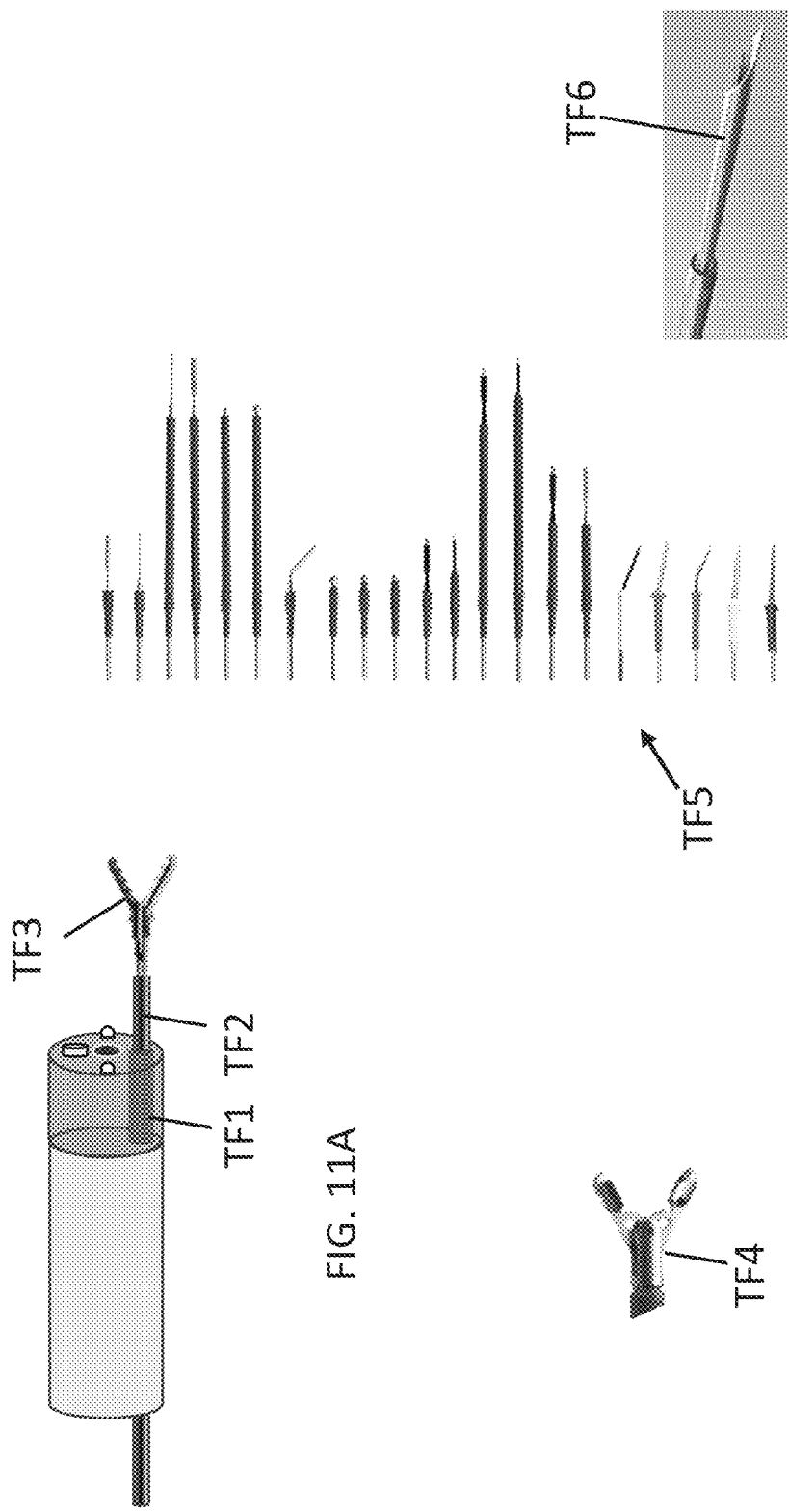

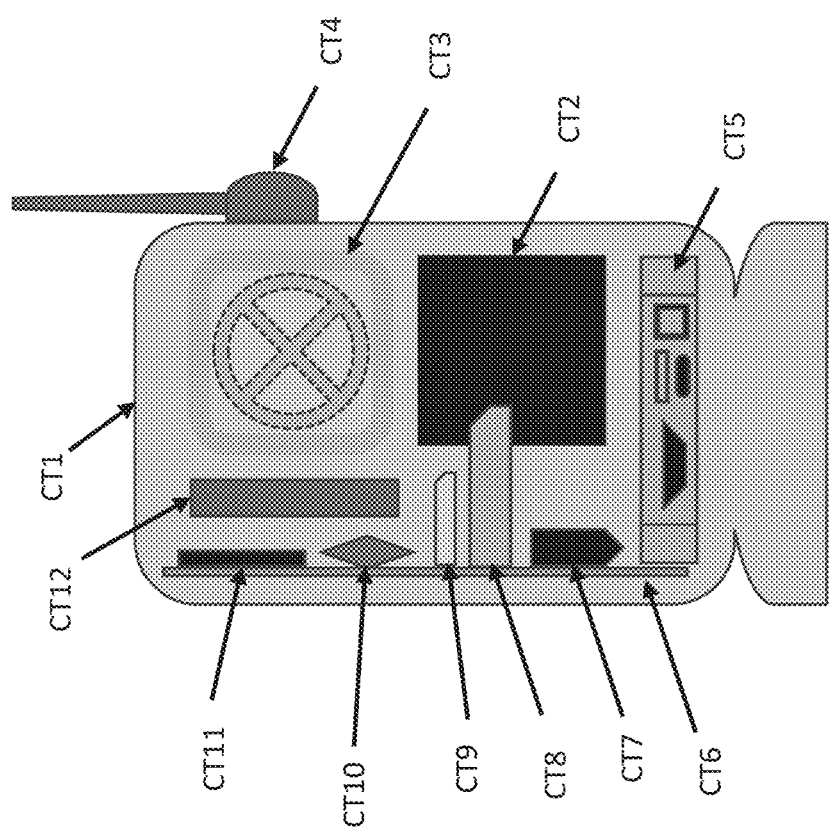

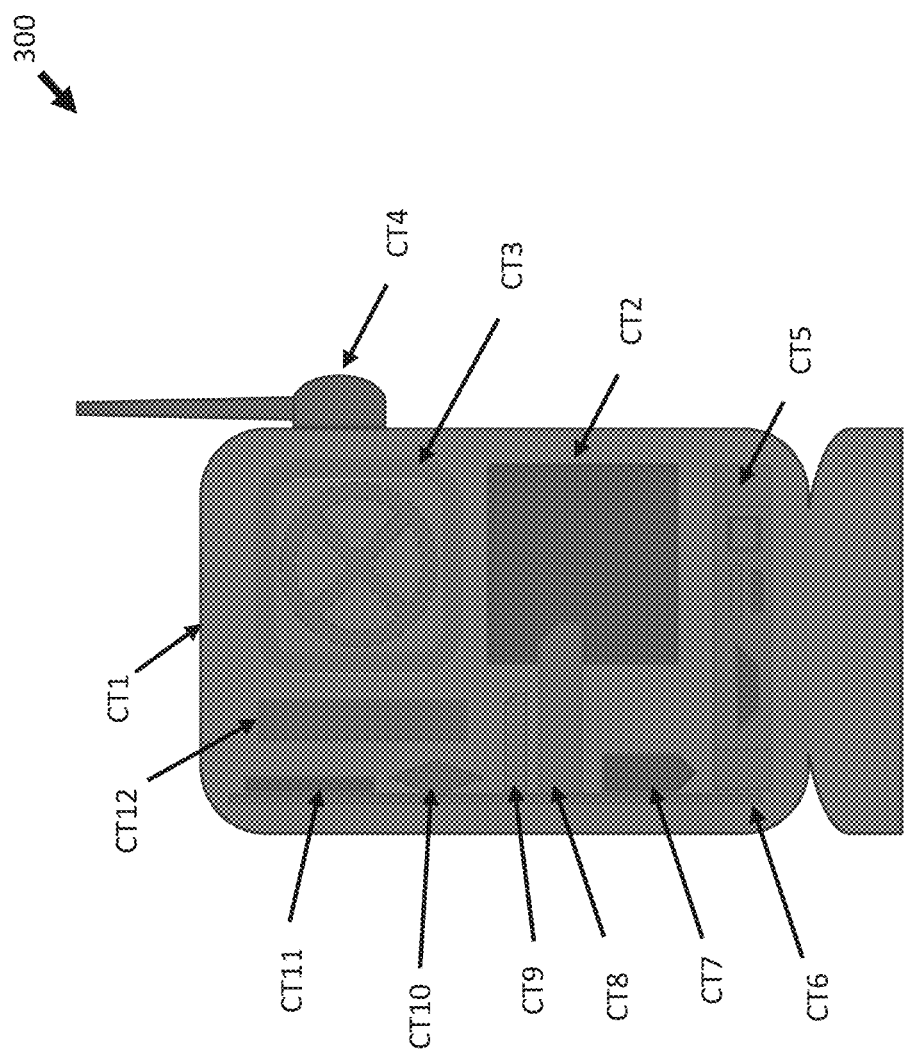

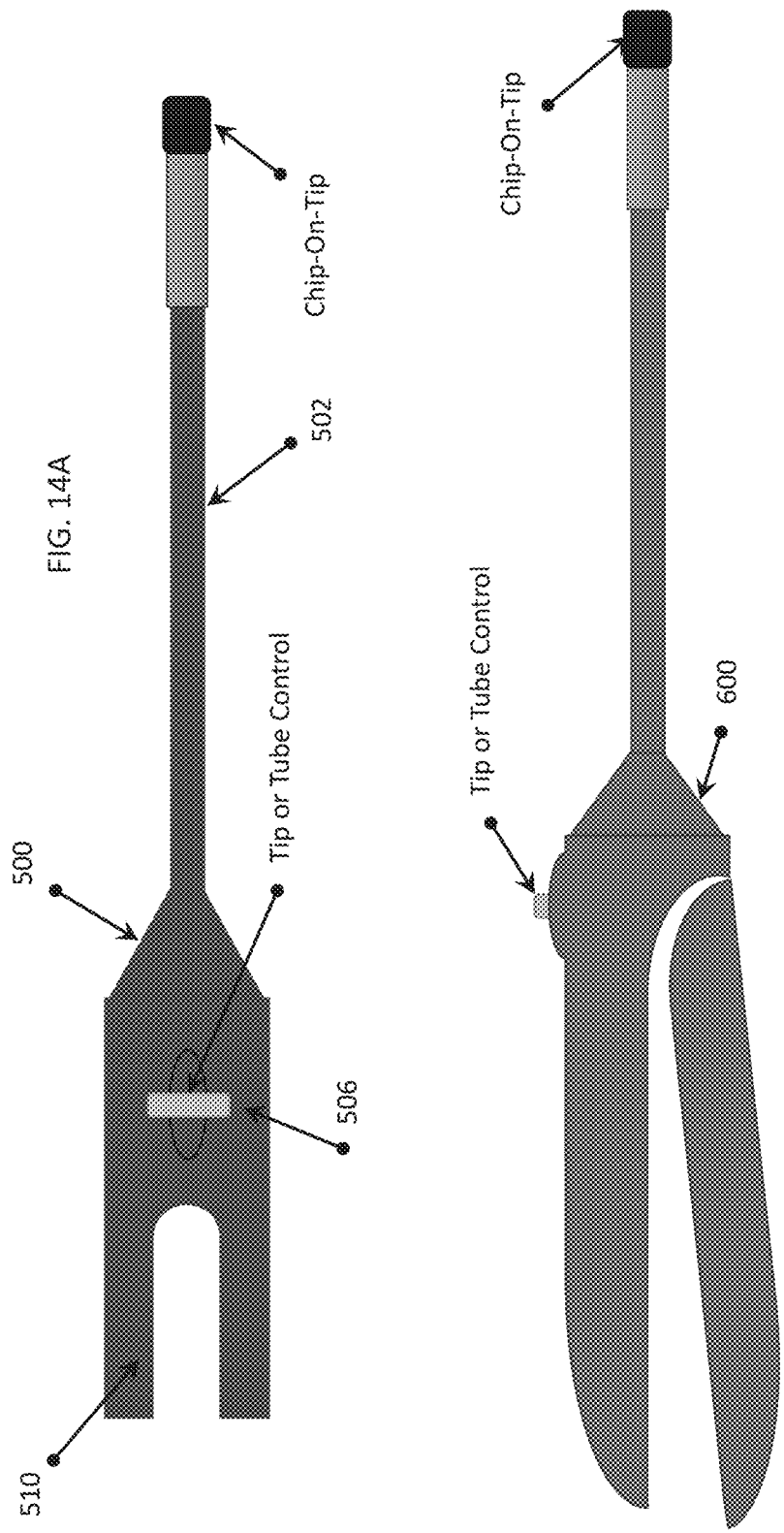

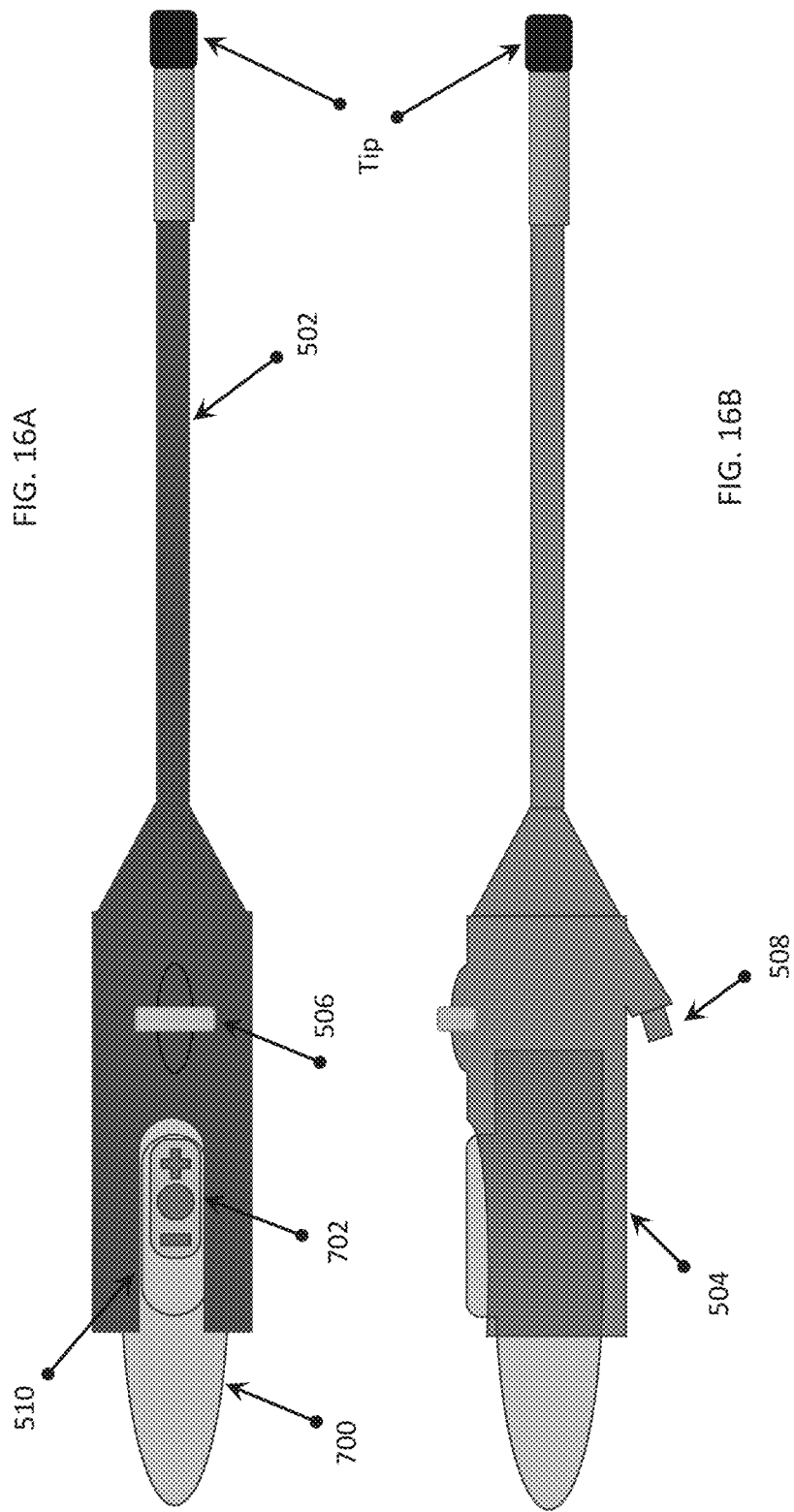

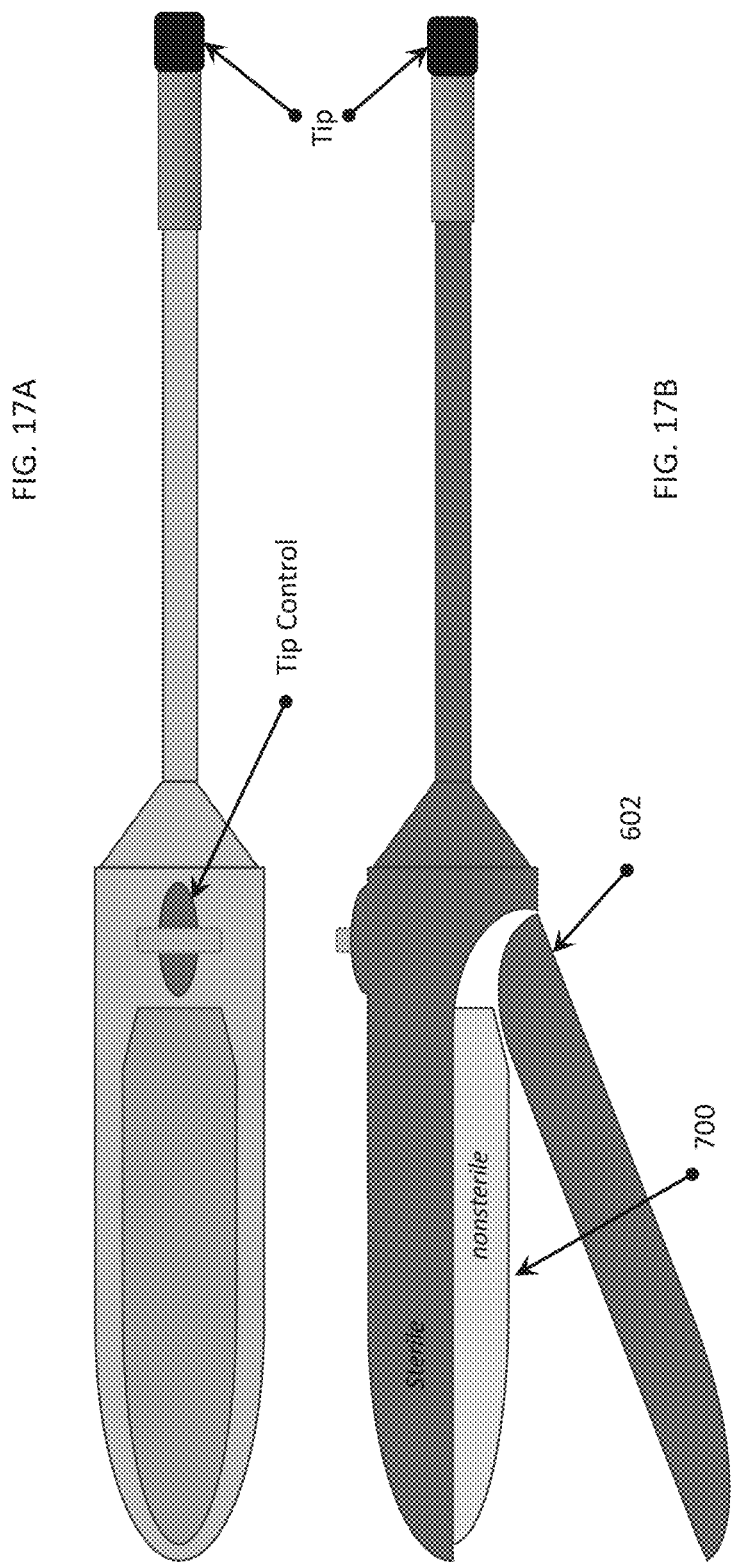

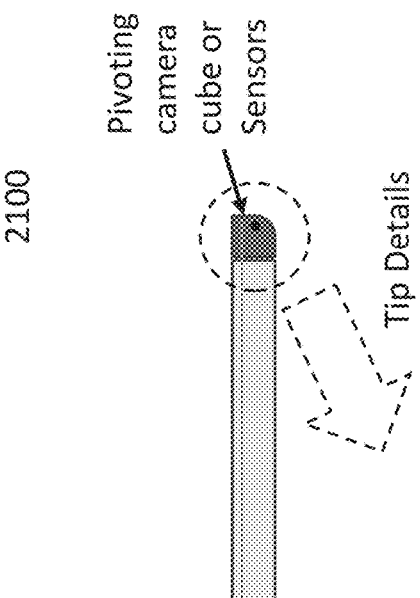
FIG. 21A
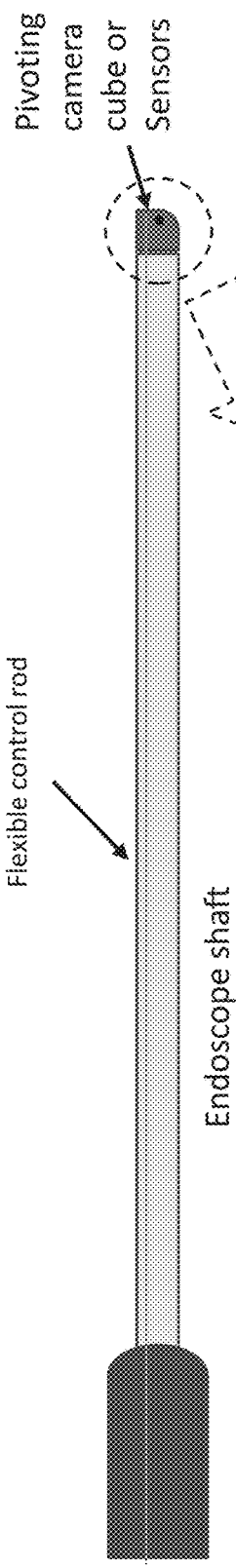
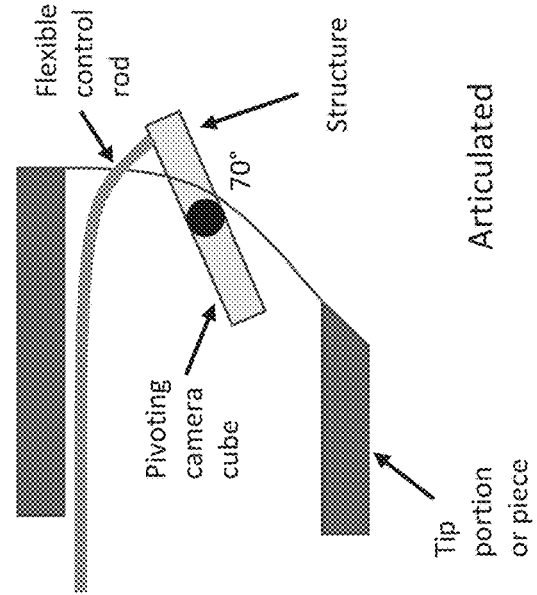
FIG. 21C
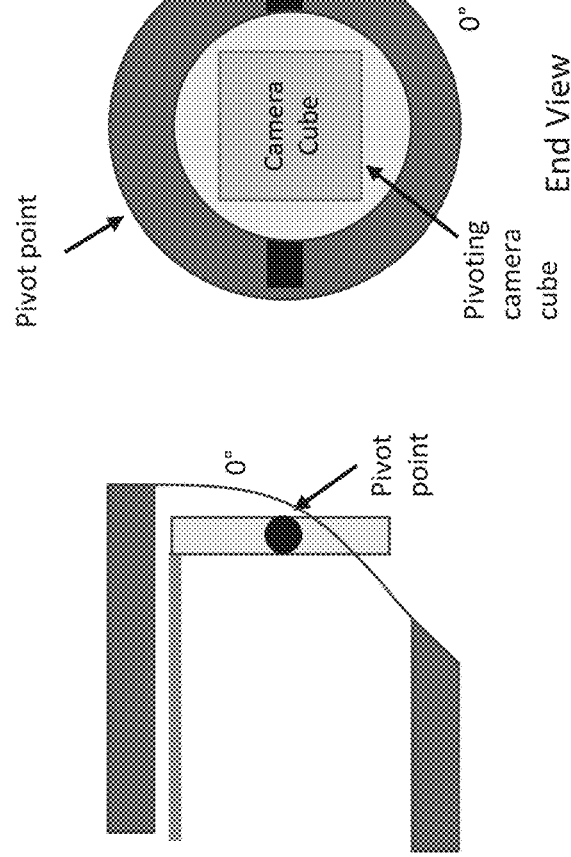
FIG. 21B
FIG. 21D

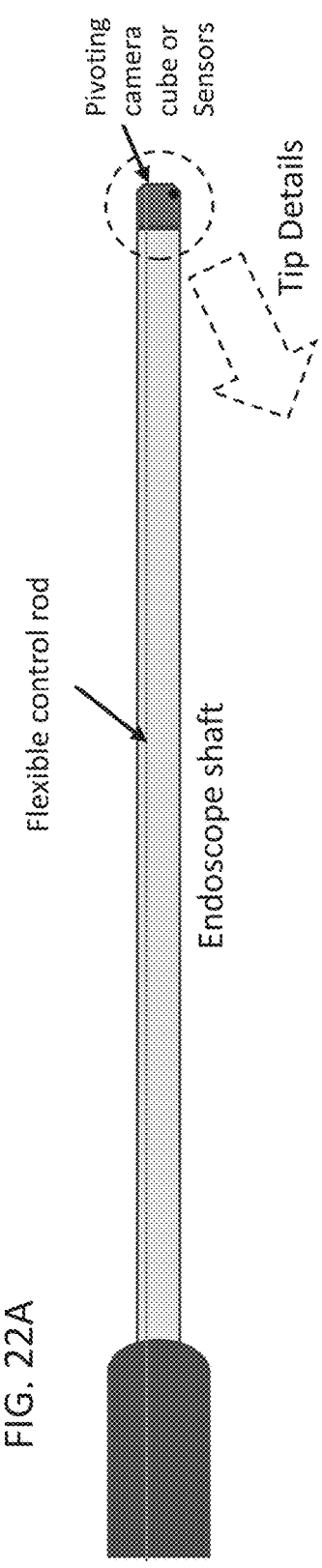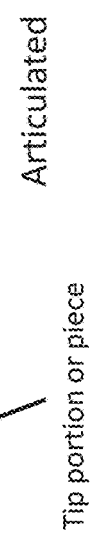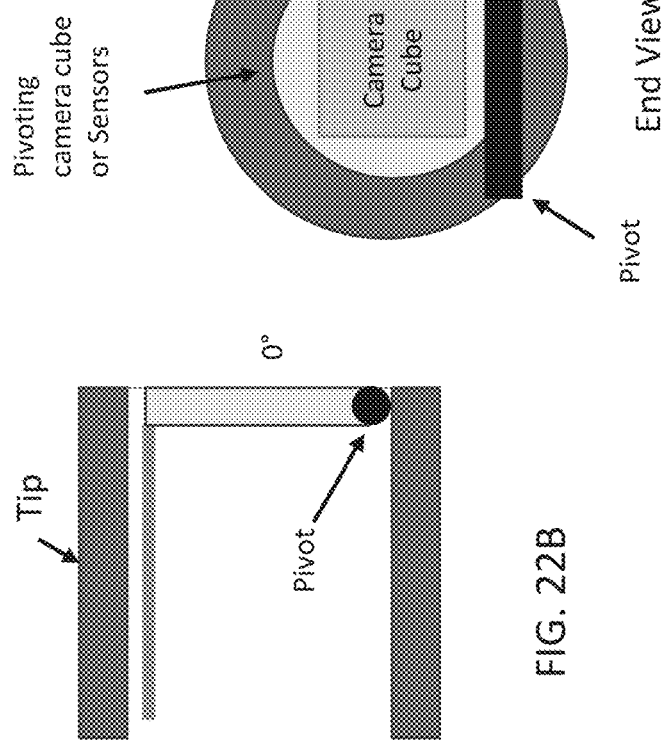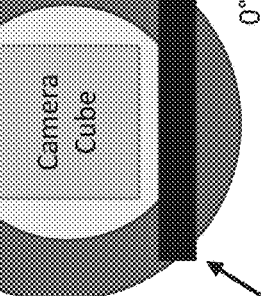
FIG. 22A
FIG. 22B
FIG. 22C
FIG. 22D

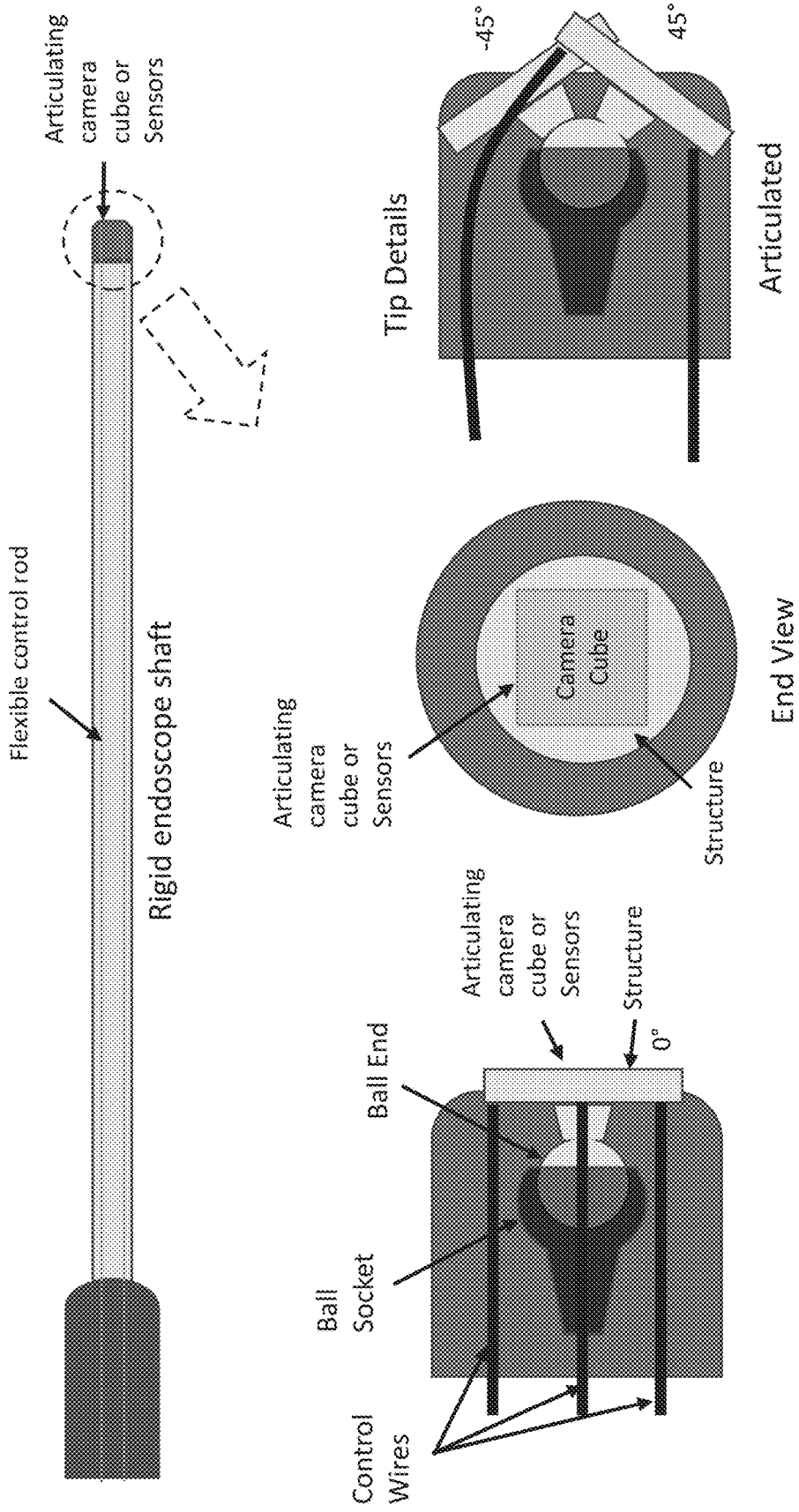

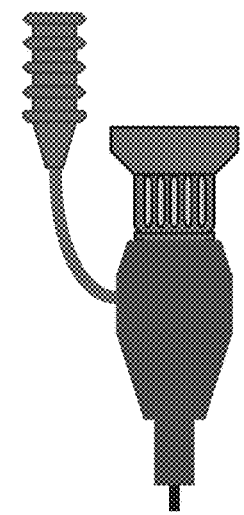
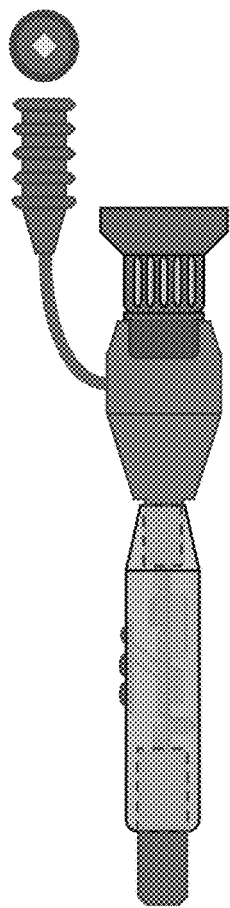
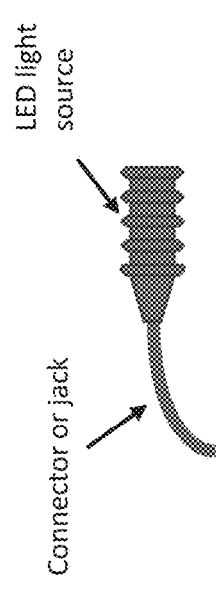
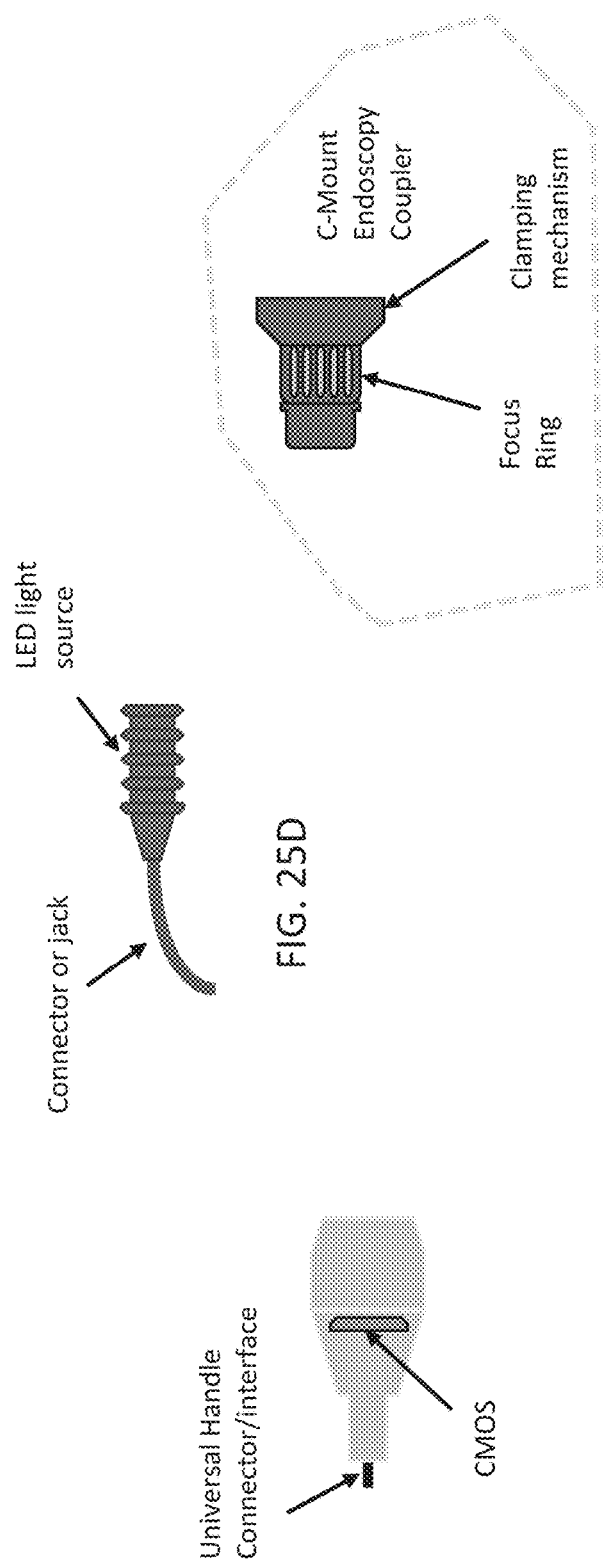
FIG. 25A
FIG. 25B
FIG. 25C
FIG. 25D
FIG. 25E
2500
LED light source
Connector or jack
Universal Handle Connector/interface
CMOS
C-Mount Endoscopy Coupler
Clamping mechanism
Focus Ring

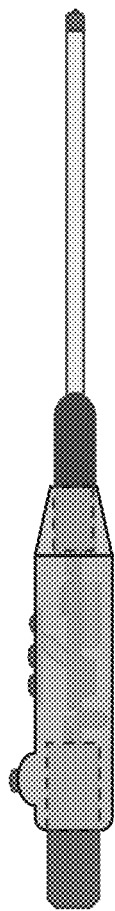
FIG. 28A
FIG. 28B

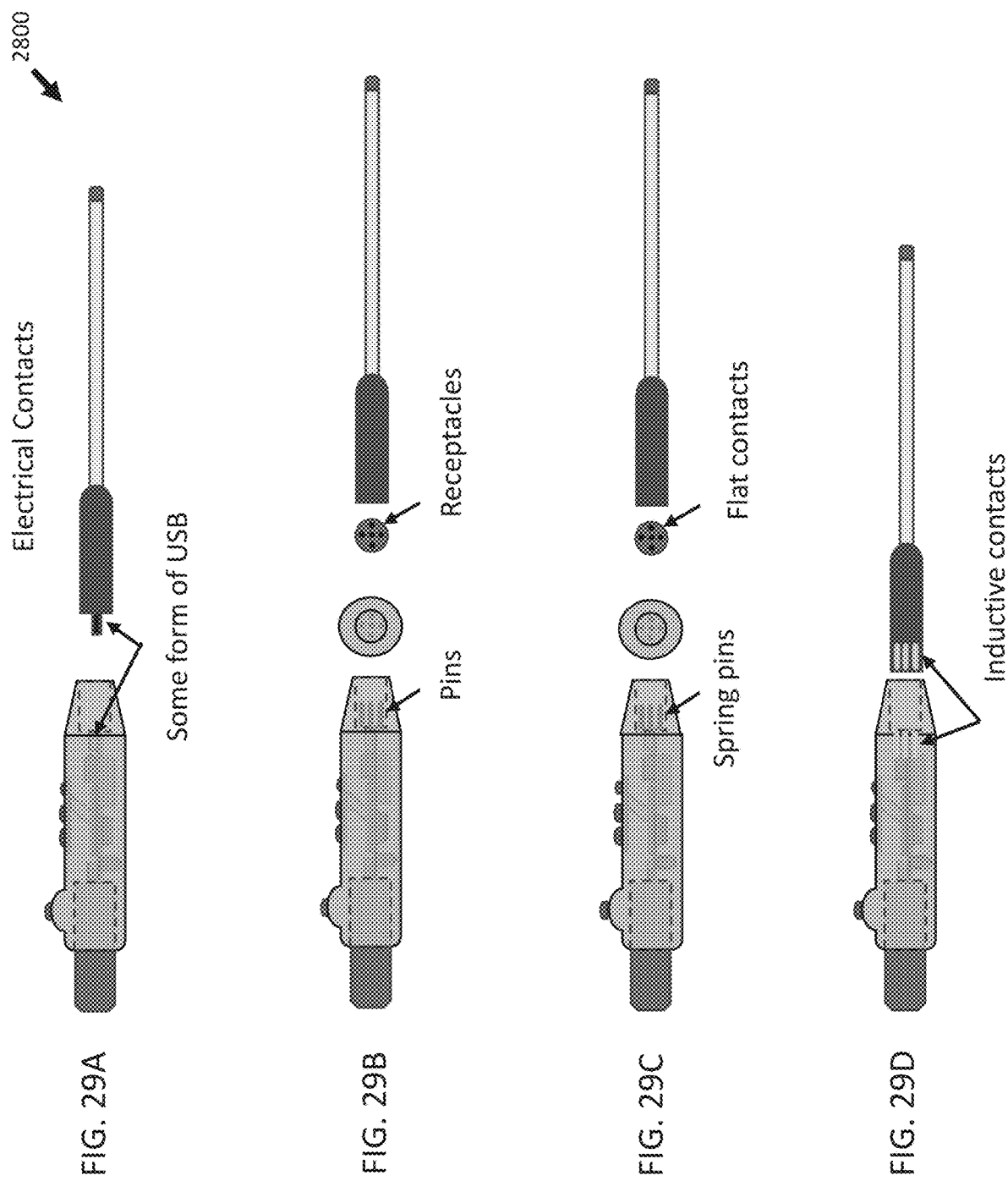

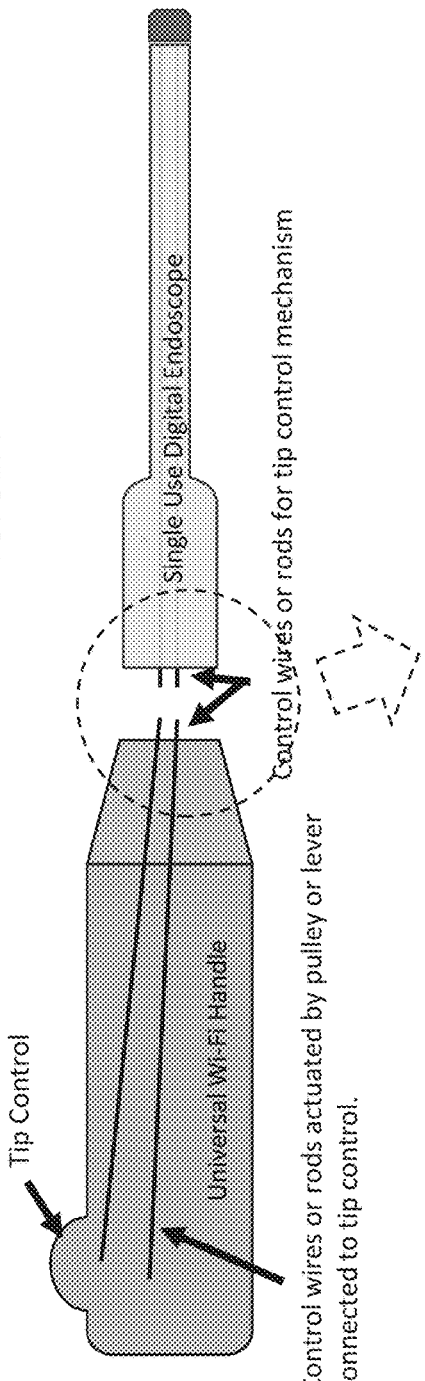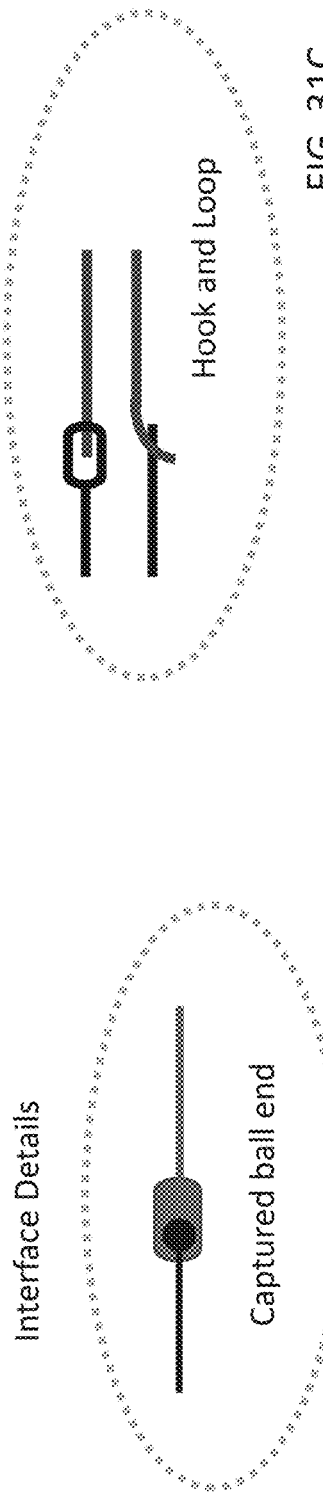

HANDHELD UNIT FOR ENDOSCOPY, LAPAROSCOPY, AND OTHER SCOPIC PROCEDURES AND METHODS OF MANUFACTURE AND USE THEREOF

CROSS-REFERENCE TO RELATED PATENT APPLICATION

This patent application claims a benefit of priority to U.S. patent application 63/451,829 filed 13 Mar. 2023, which is incorporated by reference herein in its entirety for all purposes.

TECHNICAL FIELD

This disclosure relates to technologies enabling various endoscopic procedures.

BACKGROUND

An endoscope is an instrument with various components, including a lens and a light source, that enables a cavity to be inspected, both bodily and nonbodily. Although the endoscope is useful in many situations, there are still various drawbacks limiting its functionality and usage. For example, the endoscope may be powered by a battery. As such, if the battery is depleted during a procedure, then the procedure is halted until the endoscope is powered by another energy source. Further, the endoscope may have a scope that is a reusable unit. As such, if the procedure requires the scope to be designed for a single use, then the scope is not known to be configurable for such use. Additionally, the scope may have a tip portion lacking in any sensing or end-effecting functionality. As such, if the procedure requires the scope to have such functionality, then the scope is not known to be configurable to do so. Also, the endoscope may need to minimize external wires (e.g., not tethered by a power cord or a cable to a camera or a light source), which may cause tripping or limit distance or environment of use.

SUMMARY

This disclosure enables various technologies for endoscopy, laparoscopy, and other endoscopic or scopic procedures and methods of manufacture and use thereof. For example, there may be a handheld unit (e.g., an endoscope, a laparoscope) configured to perform an endoscopic or scopic procedure in a cavity of an animate object (e.g., a mammal, an animal, a human, a pet) or an inanimate object (e.g., a tube, a container, a building, a vehicle, a plumbing item). As such, the handheld unit may be used in endoscopy, laparoscopy, colonoscopy, sinoscopy, hysteroscopy, arthroscopy, bronchoscopy, otolaryngoscopy, cystoscopy, ureteroscopy, and other suitable endoscopic or scopic procedures, whether for medical purposes (e.g., in a mammal, an animal, a human, a pet) or non-medical purposes (e.g., in a tube, a container, a building, a vehicle, a plumbing item). The handheld unit can be used together with a computing terminal (e.g., a desktop computer, a laptop computer, a smartphone, a wearable computer, a headgear computer) or a charging dock, as disclosed herein. For example, the handheld unit may include a handle and an endoscope component, whether designed for a single use (e.g., disposable) or reusable (e.g., non-disposable), where the endoscope component is insertable into the cavity for inspection of the cavity (e.g., assessment).

DESCRIPTION OF DRAWINGS

FIGS. 11A-11D show a schematic diagram of an embodiment of a scope with a portion that is retractable, expandable, or capable of cutting or inputting or outputting a gas, a gel, a foam, a solid, or a liquid according to this disclosure.

FIG. 12 shows a schematic diagram of an embodiment of a computing terminal according to this disclosure.

FIG. 13 shows a schematic diagram of an embodiment of a computing terminal with a list of features thereof according to this disclosure.

FIGS. 14A-14B show a schematic diagram of an embodiment of a scope configured to receive a power module in a non-encapsulated manner and an embodiment of a handheld unit configured to receive a power module in an encapsulated manner according to this disclosure.

FIGS. 16A-16B show a schematic diagram of an embodiment of a scope in receipt of a power module in a non-encapsulated manner according to this disclosure.

FIGS. 17A-17B show a schematic diagram of an embodiment of a handheld unit configured to receive a power module in an encapsulated manner according to this disclosure.

FIGS. 21A-21D shows a schematic diagram of an embodiment of a scope having an end portion that is pivotable according to this disclosure.

FIGS. 22A-22D show a schematic diagram of an embodiment of a scope having an end portion that is pivotable according to this disclosure.

FIGS. 23A-23D show a schematic diagram of an embodiment of a scope having an end portion hosting a ball and socket joint according to this disclosure.

FIGS. 25A-25E show a schematic diagram of an embodiment of a handle engaging an adapter engageable with an endoscope according to this disclosure.

FIGS. 28A-28B show a schematic diagram of an embodiment of a handheld unit with an interface according to this disclosure.

FIGS. 29A-29D show a schematic diagram of an embodiment of a handheld unit with a set of interfaces according to this disclosure.

FIGS. 31A-31D show a schematic diagram of an embodiment of a handheld unit with a set of interfaces according to this disclosure.

DETAILED DESCRIPTION

Figure 1:
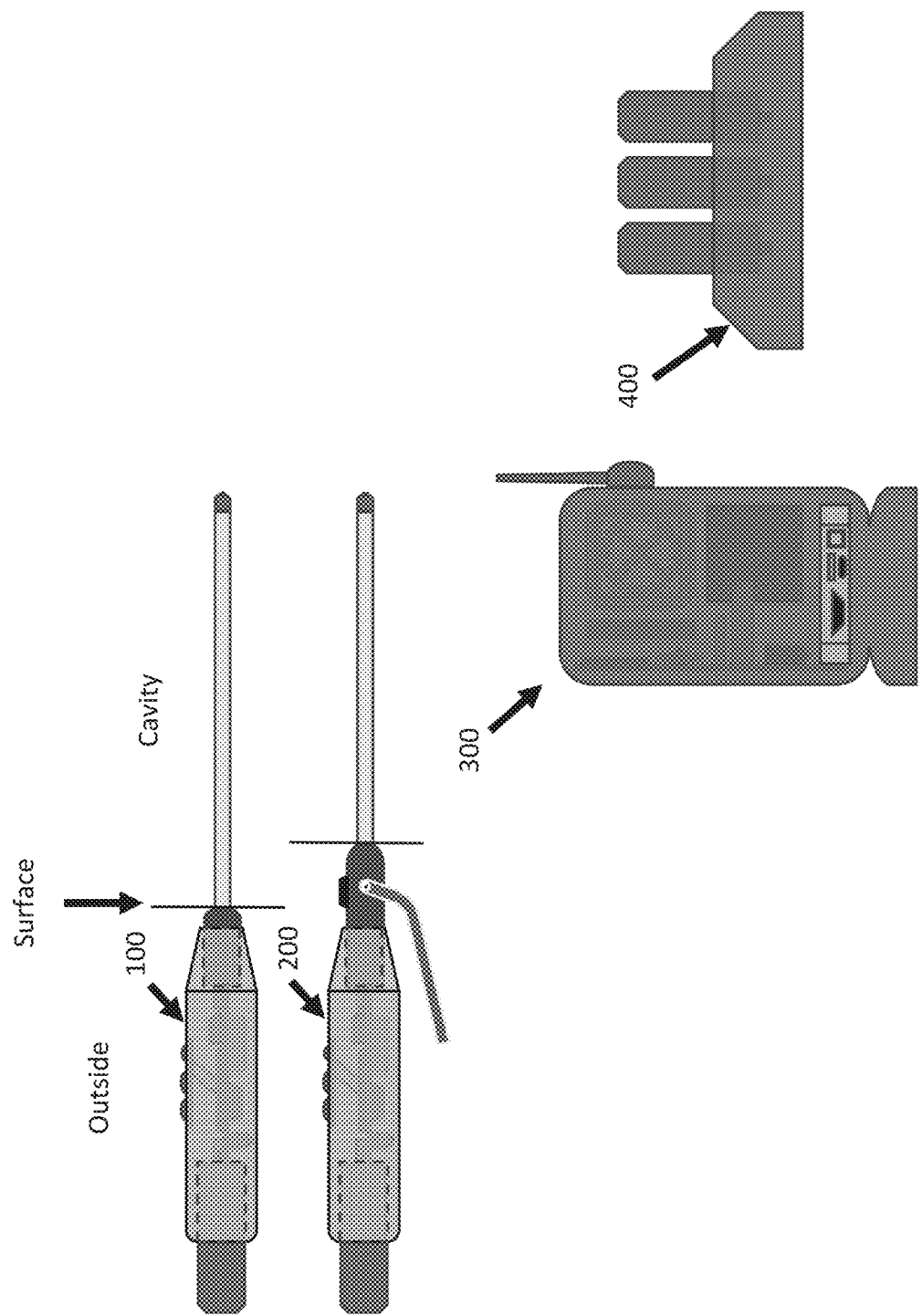
FIG. 1 shows a schematic diagram of an embodiment of a system or a kit according to this disclosure.

As explained above, this disclosure enables various technologies for endoscopy, laparoscopy, and other endoscopic or scopic procedures and methods of manufacture and use thereof. For example, there may be a handheld unit (e.g., an endoscope, a laparoscope) configured to perform an endoscopic or scopic procedure in a cavity of an animate object (e.g., a mammal, an animal, a human, a pet) or an inanimate object (e.g., a tube, a container, a building, a vehicle, a plumbing item). As such, the handheld unit may be used in endoscopy, laparoscopy, colonoscopy, sinoscopy, hysteroscopy, arthroscopy, bronchoscopy, otolaryngoscopy, cystoscopy, ureteroscopy, and other suitable endoscopic or scopic procedures, whether for medical purposes (e.g., in a mammal, an animal, a human, a pet) or non-medical purposes (e.g., in a tube, a container, a building, a vehicle, a plumbing item). The handheld unit can be used together with a computing terminal (e.g., a desktop computer, a laptop computer, a smartphone, a wearable computer, a headgear computer) or a charging dock, as disclosed herein. For example, the handheld unit may include a handle and an endoscope component, whether designed for a single use (e.g., disposable) or reusable (e.g., non-disposable), where the endoscope component is insertable into the cavity for inspection of the cavity (e.g., assessment). However, note that this disclosure may be embodied in many different forms and should not be construed as necessarily being limited to various embodiments disclosed herein. Rather, these embodiments are provided so that this disclosure is thorough and complete, and fully conveys various concepts of this disclosure to skilled artisans. Note that like numbers or similar numbering schemes can refer to like or similar elements throughout.

Various terminology used herein can imply direct or indirect, full or partial, temporary or permanent, action or inaction. For example, when an element is referred to as being "on," "connected" or "coupled" to another element, then the element can be directly on, connected or coupled to the other element or intervening elements can be present, including indirect or direct variants. In contrast, when an element is referred to as being "directly connected" or "directly coupled" to another element, there are no intervening elements present.

As used herein, a term "about" or "substantially" refers to a +/−10% variation from a nominal value/term.

Although various terms, such as first, second, third, and so forth can be used herein to describe various elements, components, regions, layers, or sections, note that these elements, components, regions, layers, or sections should not necessarily be limited by such terms. Rather, these terms are used to distinguish one element, component, region, layer, or section from another element, component, region, layer, or section. As such, a first element, component, region, layer, or section discussed below could be termed a second element, component, region, layer, or section, without departing from this disclosure.

As used herein, when this disclosure states herein that something is "based on" something else, then such statement refers to a basis which may be based on one or more other things as well. In other words, unless expressly indicated otherwise, as used herein "based on" inclusively means "based at least in part on" or "based at least partially on."

As used herein, a term "or" is intended to mean an inclusive "or" rather than an exclusive "or." That is, unless specified otherwise, or clear from context, "X employs A or B" is intended to mean any of natural inclusive permutations. That is, if X employs A; X employs B; or X employs both A and B, then "X employs A or B" is satisfied under any of the foregoing instances. For example, X includes A or B can mean X can include A, X can include B, and X can include A and B, unless specified otherwise or clear from context.

As used herein, each of singular terms "a," "an," and "the" is intended to include a plural form (e.g., two, three, four, five, six, seven, eight, nine, ten, tens, hundreds, thousands, millions) as well, including intermediate whole or decimal forms (e.g., 0.0, 0.00, 0.000), unless context clearly indicates otherwise. Likewise, each of singular terms "a," "an," and "the" shall mean "one or more," even though a phrase "one or more" may also be used herein.

As used herein, each of terms "comprises," "includes," or "comprising," "including" specify a presence of stated features, integers, steps, operations, elements, or components, but do not preclude a presence or addition of one or more other features, integers, steps, operations, elements, components, or groups thereof.

As used herein, terms, such as "then," "next," or other similar forms are not intended to limit an order of steps. Rather, these terms are simply used to guide a reader through this disclosure. Although process flow diagrams may describe some operations as a sequential process, many of those operations can be performed in parallel or concurrently. In addition, the order of operations may be re-arranged.

As used herein, a term "response" or "responsive" are intended to include a machine-sourced action or inaction, such as an input (e.g., local, remote), or a user-sourced action or inaction, such as an input (e.g., via user input device).

Unless otherwise defined, all terms (including technical and scientific terms) used herein have a same meaning as commonly understood by skilled artisans to which this disclosure belongs. These terms, such as those defined in commonly used dictionaries, should be interpreted as having a meaning that is consistent with their meaning in context of relevant art and should not be interpreted in an idealized or overly formal sense, unless expressly so defined herein.

Features or functionality described with respect to certain embodiments may be combined and sub-combined in or with various other embodiments. Also, different aspects, components, or elements of embodiments, as disclosed herein, may be combined and sub-combined in a similar manner as well. Further, some embodiments, whether individually or collectively, may be components of a larger system, wherein other procedures may take precedence over or otherwise modify their application. Additionally, a number of steps may be required before, after, or concurrently with embodiments, as disclosed herein. Note that any or all methods or processes, as disclosed herein, can be at least partially performed via at least one entity or actor in any manner.

Hereby, all issued patents, published patent applications, and non-patent publications that are mentioned or referred to in this disclosure are herein incorporated by reference in their entirety for all purposes, to a same extent as if each individual issued patent, published patent application, or non-patent publication were specifically and individually indicated to be incorporated by reference. To be even more clear, all incorporations by reference specifically include those incorporated publications as if those specific publications are copied and pasted herein, as if originally included in this disclosure for all purposes of this disclosure. Therefore, any reference to something being disclosed herein includes all subject matter incorporated by reference, as explained above. However, if any disclosures are incorporated herein by reference and such disclosures conflict in part or in whole with this disclosure, then to an extent of the conflict or broader disclosure or broader definition of terms, this disclosure controls. If such disclosures conflict in part or in whole with one another, then to an extent of conflict, the later-dated disclosure controls.

Figure 2:
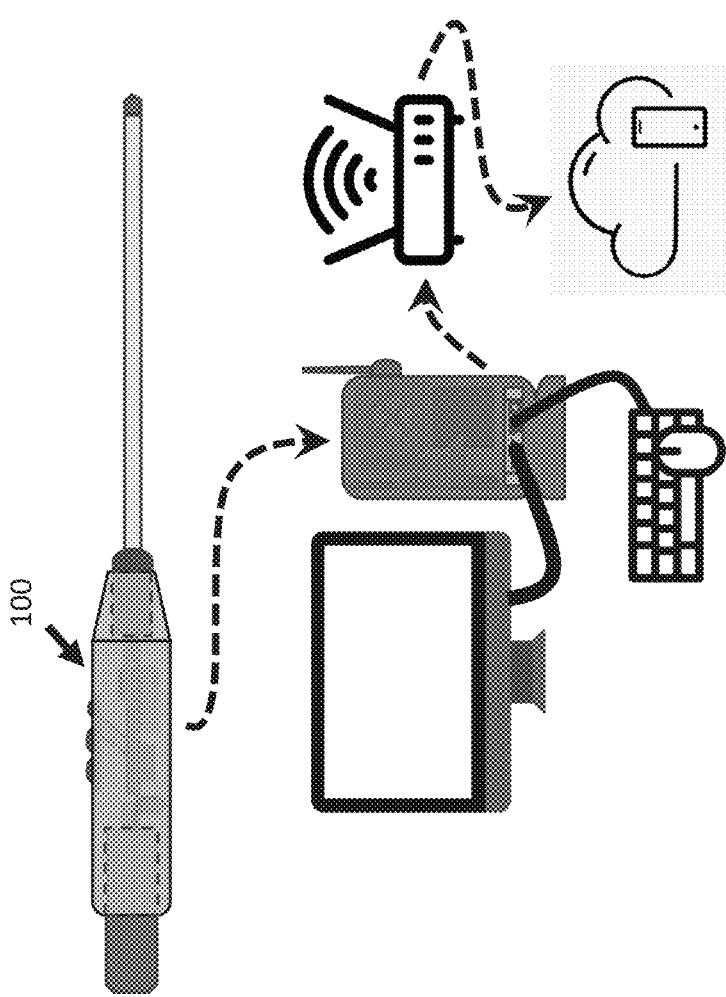
FIG. 2 shows a schematic diagram of an embodiment of a system or a kit being manufactured or used according to this disclosure.

FIG. 1 shows a schematic diagram of an embodiment of a system or a kit according to this disclosure. FIG. 2 shows a schematic diagram of an embodiment of a system or a kit being manufactured or used according to this disclosure. In particular, there is a system or a kit including a handheld unit 100 or a handheld unit 200, a computing terminal 300, and a charging dock 400. The system or the kit may include the handheld unit 100 or the handheld 200 or both. As disclosed herein, the handheld unit 100 and the handheld unit 200 are generally similar to each other, but differ from each other in its respective scopes being rigid (the handheld unit 100) or steerable (the handheld unit 200).

Regardless of how the handheld unit 100 or the handheld unit 200 is configured, the system or the kit enable performance of endoscopy, laparoscopy, and other scopic procedures. For example, the handheld unit 100 or the handheld unit 200 may be embodied as an endoscope, a laparoscope, or another suitable form factor and be configured to perform a scopic procedure in a cavity of an animate object (e.g., a mammal, an animal, a human, a pet) or an inanimate object (e.g., a tube, a container, a building, a vehicle, a plumbing item). As such, the handheld unit 100 or the handheld unit 200 may be used in endoscopy, laparoscopy, colonoscopy, sinoscopy, hysteroscopy, arthroscopy, bronchoscopy, otolaryngoscopy, cystoscopy, ureteroscopy, and other suitable scopic procedures, whether for medical purposes (e.g., in a mammal, an animal, a human, a pet) or non-medical purposes (e.g., in a tube, a container, a building, a vehicle, a plumbing item). For example, each of the handheld unit 100 or the handheld unit 200 may include a handle and a scope, as disclosed herein, where the scope or the handle may be designed for a single use or multiple uses. For example, the handle and the scope may be longitudinally co-aligned with each other along a common plane or a common axis (e.g., symmetry or rotation), as shown in FIGS. 1-18. The handheld unit 100 or the handheld unit 200 can be used together with the computing terminal 200, which may be embodied as a desktop computer, a laptop computer, a smartphone, a wearable computer, a headgear computer, or another suitable computing form factor, or the charging dock 400, as disclosed herein.

Although variations are possible, generally, to perform a scopic procedure with the system or the kit referenced above, the handheld unit 100 or the handheld unit 200 wirelessly connect to and wirelessly communicate with the computing terminal 300 using Wi-Fi, Bluetooth, Li-Fi, or another suitable radio or line-of-sight (e.g., optical, infrared, sound) communication protocol. This form of connection and communication may happen before, during, or after the handheld unit 100 or the handheld unit 200 is inserted into a cavity to be inspected. For example, the cavity may be within an object, whether animate (e.g., a mammal, an animal, a human, a pet) or inanimate (e.g., a plumbing component, a dangerous area). When the handheld unit 100 or the handheld unit 200 hosts a battery powering its operations (e.g., imaging, steering), the battery may be hot-swappable during such operations, without halting those operations, with another battery, which may be charged at the charging dock 400, as disclosed herein.

Once the handheld unit 100 or the handheld unit 200 are wirelessly connected to the computing terminal 300, the handheld unit 100 or the handheld unit 200 may wirelessly communicate with the computing terminal 300 and wirelessly send (e.g., wirelessly stream) an imagery of the cavity from the handheld unit 100 or the handheld unit 200 to the computing terminal 300. As such, this enables the system or the kit including the handheld unit 100 or the handheld unit 200 hosting a handle, an energy store, a scope, and a first wireless communication interface; and the computing terminal 300 hosting a second wireless communication interface, where the second wireless communication interface receives an imagery of a cavity captured via the scope powered by the energy store when the scope extends within the cavity as a user holds the handle outside the cavity, as disclosed herein. For example, the handheld unit 100 or the handheld unit 200 may host an encoder or another suitable encoding form factor, whether in hardware or software, to encode the imagery or otherwise suitably process, whether in hardware or software, the imagery to enable wireless streaming from the handheld unit 100 or the handheld unit 200. For example, the imagery may have a resolution and such encoding may increase or reduce the resolution, as needed. However, encoding for other purposes (e.g., bandwidth management, power management) may be possible, whether additionally or alternatively.

The computing terminal 300 may itself display or enable display by an electronic display (e.g., a liquid crystal display (LCD), a plasma display, an electrophoretic display, a volumetric display, a wearable display, a head-mounted display) connected (e.g., wired, wireless, waveguide) to the computing terminal 300 of the imagery received from the handheld unit 100 or the handheld unit 200. For example, the computing terminal 300 may have an High-Definition Multimedia Interface (HDMI) port or another suitable port or interface, whether hardware or software, through which the imagery may be displayed if the electronic display is connected (e.g., wired, wireless, waveguide) to the computing terminal 300 via the HDMI port or another suitable port.

The computing terminal 300 may have a user input device or a set of user input devices that enable control of the imagery or other relevant functions related to the imagery. For example, the user input device or the set of user input devices may include a physical keyboard, a virtual keyboard, a cursor control device, a mouse, a touchpad, a trackball, a touchscreen, a microphone, or another suitable user input form factor.

The computing terminal 300 may connect, whether directly or indirectly, with a local area network (LAN), a wide area network (WAN), a cellular network (e.g., 3G, 4G, 5G, 6G, 7G), a satellite network, or another suitable network form factor, to communicate with a web application hosted on a server (e.g., physical or virtual) remote to the computing terminal 300. For example, the computing terminal 300 may connect (e.g., wired, wirelessly, waveguide, directly, indirectly) to a network router, a network switch, a network extender, a network access point, or another suitable network access form factor connected to the LAN, WAN, the cellular network, the satellite network, or another suitable network form factor.

The web application may communicate with a database (e.g., relational, graph, in-memory) storing a set of records, where the web application may retrieve at least some of those records and present those records for the user to review or edit, on-demand, whether from the computing terminal 300 or another computing terminal (e.g., a desktop computer, a laptop computer, a smartphone, a wearable computer, a headgear computer). For example, the set of records may be a set of electronic medical records (EMR) and the user may be a physician, a nurse, or another suitable medical professional reviewing or editing at least some of those records from the computing terminal 300 or another computing terminal, where at least some of those records may include the imagery captured by the handheld unit 100 or the handheld unit 200 when inspecting a cavity within a patient (e.g., an adult human, a child human, an elderly human), which may be during a medical procedure (e.g., endoscopy, laparoscopy, colonoscopy, sinoscopy, hysteroscopy, arthroscopy bronchoscopy, otolaryngoscopy, cystoscopy, ureteroscopy). For example, such imagery may be time-stamped or date-stamped by the handheld unit 100, the handheld unit 200, the computing terminal 300, the web application, or the database.

Figure 3:
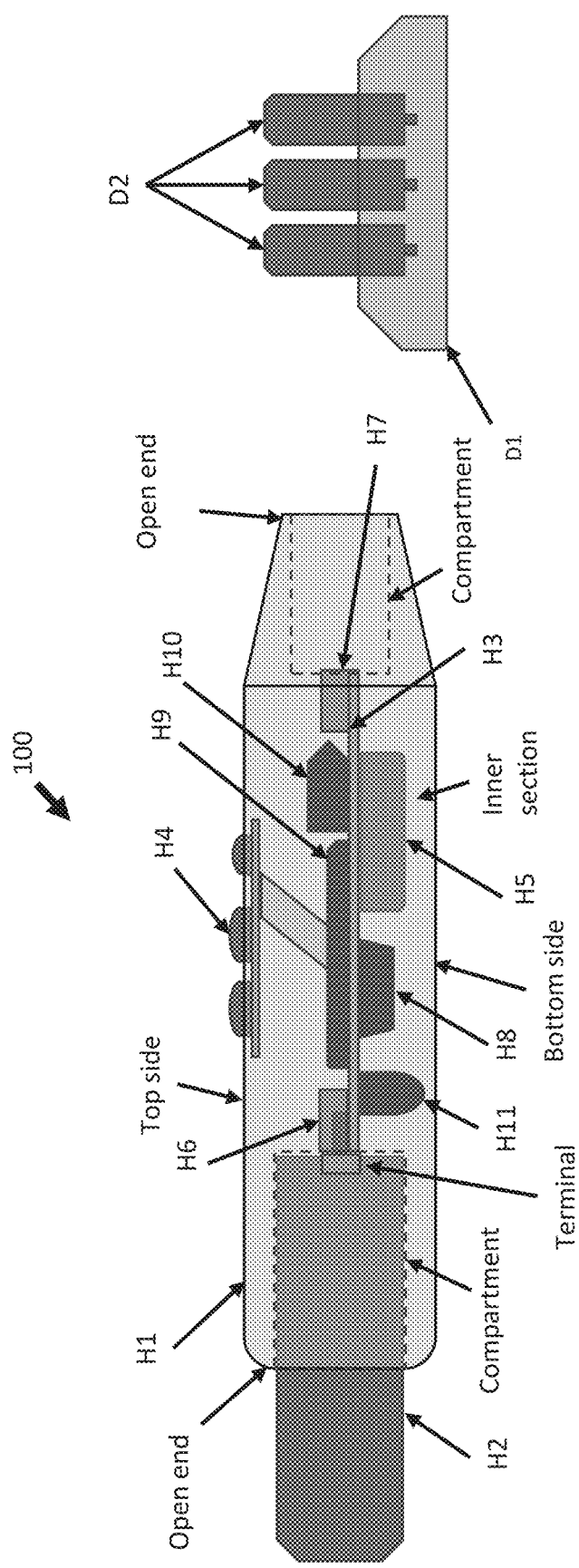
FIG. 3 shows a schematic diagram of an embodiment of a handle of a handheld unit and an embodiment of a dock according to this disclosure.
Figure 4:
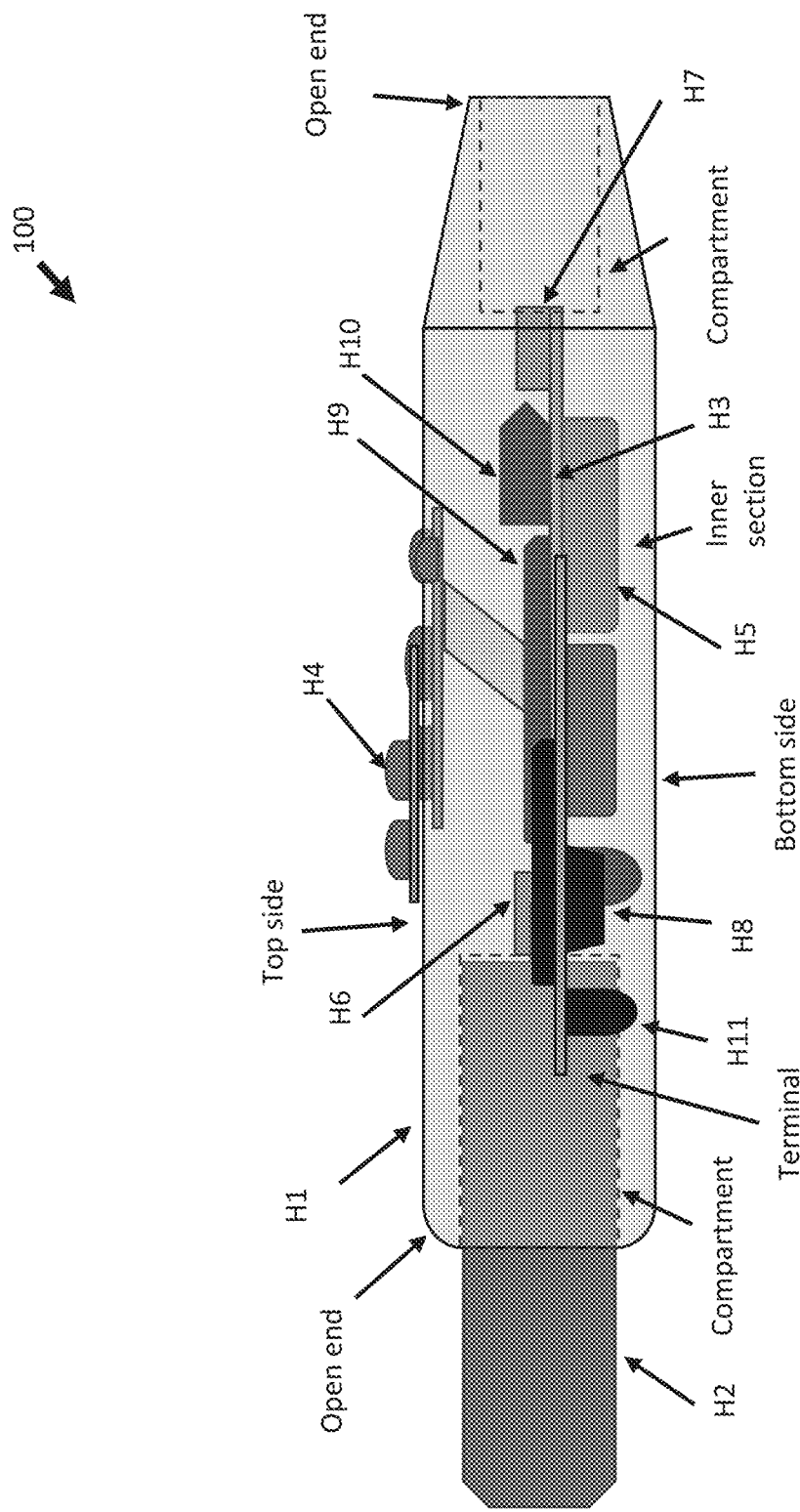
FIG. 4 shows a schematic diagram of an embodiment of a handle of a handheld unit with a list of features thereof according to this disclosure.

FIG. 3 shows a schematic diagram of an embodiment of a handle of a handheld unit and an embodiment of a dock according to this disclosure. FIG. 4 shows a schematic diagram of an embodiment of a handle of a handheld unit with a list of features thereof according to this disclosure. In particular, the handheld unit 100 or the handheld unit 200 may include a handle H1, an external energy store H2, a circuit board H3, a control panel H4, an internal energy store H5, an charging interface H6, a scope interface H7, a gyroscope or an accelerometer H8, a processor H9, a wireless communication interface H10, and a microphone H11. The charging dock 400 (e.g., a docking station) includes a base D1 and a set of external energy stores D2.

The handle H1 is rectilinearly tubular in shape (similar to a handle of a handheld screwdriver or a handheld electric toothbrush), but can be shaped differently. For example, the handle H1 may be shaped as non-rectilinear, non-tubular, a puck, a sphere, a spheroid, a cube, a cuboid, an arc, a crescent, a pyramid, a cone, or another suitable shape, whether open-shaped or closed-shaped, whether symmetrical or asymmetrical.

The handle H1 extends longitudinally along a plane. As shown in FIG. 3, the handle H1 extends longitudinally along a horizontal plane, although this extension can vary depending on how the handle H1 is oriented. For example, the handle H1 can extend longitudinally along a vertical plane or a diagonal plane, depending on how the handle H1 is oriented. Similarly, the handle H1 extends longitudinally along an axis, whether an axis of symmetry or an axis of rotation. For example, the handle H1 has a symmetrical shape along the horizontal plane, although this shaping may vary and the handle H1 may have an asymmetrical shape along the horizontal plane, the vertical plane, or the diagonal plane. The handle H1 may have a circular cross-section, although another suitable cross-section is possible (e.g., open-shaped, closed-shape, symmetrical, asymmetrical, square, rectangle, octagon, pentagon, triangle, trapezoid).

The handle H1 constitutes plastic, but can constitute other suitable materials. For example, the handle H1 may constitute metal, alloy, rubber, silicone, or other suitable materials, whether natural or synthetic. In some situations, the handle H1 is configured for or constituted of such materials that are safe for sterilization, which may be performed via heat, chemicals, radiation, or other suitable processes, whether before or after scoping, as disclosed herein. For example, such sterilization may occur via exposure to steam, ultraviolet (UV) light, or another form of sterilization, whether within an autoclave or another suitable apparatus. In some situations, the handle H1 is water-proof, water-tight, water-resistant, or another suitable anti-water configuration. For example, the handle H1 may be configured for use when diving in a body of water (e.g., within about 10 meters, about 25 meters, about 50 meters). The handle H1 hosts, whether interiorly or exteriorly, the external energy store H2, the circuit board H3, the control panel H4, the internal energy store H5, the charging interface H6, the scope interface H7, the gyroscope or the accelerometer H8, the processor H9, the wireless communication interface H10, and the microphone H11.

As shown in FIG. 3, the handle H1 is a housing, a case, or an enclosure that houses, encases, or encloses, whether interiorly or exteriorly, the external energy store H2, the circuit board H3, the control panel H4, the internal energy store H5, the charging interface H6, the scope interface H7, the gyroscope or the accelerometer H8, the processor H9, the wireless communication interface H10, and the microphone H11. As such, the handle H1 has a first end portion (left side), a first compartment, an inner section, a second compartment, and a second end portion (right side). The handle H1 also has a top side and a bottom side. The first end portion is open and leads to the first compartment along the horizontal plane, the axis of symmetry, and the axis of rotation, as shown in FIG. 3, although other configurations are possible (e.g., an elbow shape, a sinusoidal shape). The first compartment extends between the top side and the bottom side along the horizontal plane, the axis of symmetry, and the axis of rotation, as shown in FIG. 3, although other configurations are possible. The second end portion is open and leads to the second compartment along the horizontal plane, the axis of symmetry, and the axis of rotation, as shown in FIG. 3, although other configurations are possible (e.g., an elbow shape, a sinusoidal shape). The second compartment extends between the top side and the bottom side along the horizontal plane, the axis of symmetry, and the axis of rotation, as shown in FIG. 3, although other configurations are possible (e.g., an elbow shape, a sinusoidal shape). The inner section extends between the first compartment and the second compartment along the horizontal plane, the axis of symmetry, and the axis of rotation, as shown in FIG. 3, although other configurations are possible. The inner section extends between the top side and the bottom side along the horizontal plane, the axis of symmetry, and the axis of rotation, as shown in FIG. 3, although other configurations are possible. Note that these configurations are not required and the handle H1 may have a single compartment spanning at least two of the first compartment, the inner section, or the second compartment, where the first end portion leads to the single compartment or the second end portion leads to the single compartment.

The external energy store H2 is a housing, a case, or an enclosure that houses, encases, or encloses, whether interiorly or exteriorly, a store of energy (e.g., chemical, electrical, mechanical, thermal). For example, the store of energy may be a battery (e.g., AA, AAA, coin cell), an energy cell, a capacitor, a spring, a heat pack, or another suitable energy form factor, whether rechargeable or non-rechargeable. For example, the external energy store H2 may be a module embodied as the housing, the case, or the enclosure that houses, encases, or encloses the store of energy. The external energy store H2 is swappable, which may be hot-swappable, as disclosed herein, before, during, or after a procedure. The external energy store H2 can be designed for a single use (e.g., disposable) or multiple uses (e.g., rechargeable).

The external energy store H2 is rectilinearly tubular in shape (similar to a handle of a handheld screwdriver or a handheld electric toothbrush), but can be shaped differently. For example, the external energy store H2 may be shaped as non-rectilinear, non-tubular, a puck, a sphere, a spheroid, a cube, a cuboid, an arc, a crescent, a pyramid, a cone, or another suitable shape, whether open-shaped or closed-shaped, whether symmetrical or asymmetrical. The external energy store H2 may have a circular cross-section, although another suitable cross-section is possible (e.g., open-shaped, closed-shape, symmetrical, asymmetrical, square, rectangle, octagon, pentagon, triangle, trapezoid).

The external energy store H2 extends longitudinally along a plane. As shown in FIG. 3, the external energy store H2 extends longitudinally along a horizontal plane, although this extension can vary depending on how the external energy store H2 is oriented. For example, the external energy store H2 can extend longitudinally along a vertical plane or a diagonal plane, depending on how the external energy store H2 is oriented. Similarly, the external energy store H2 extends longitudinally along an axis, whether an axis of symmetry or an axis of rotation. For example, the external energy store H2 has a symmetrical shape along the horizontal plane, although this shaping may vary and the external energy store H2 may have an asymmetrical shape along the horizontal plane, the vertical plane, or the diagonal plane.

The external energy store H2 constitutes plastic, but can constitute other suitable materials. For example, the external energy store H2 may constitute metal, alloy, rubber, silicone, or other suitable materials, whether natural or synthetic. In some situations, the external energy store H2 is configured for or constituted of such materials that are safe for sterilization, which may be performed via heat, chemicals, radiation, or other suitable processes, whether before or after scoping, as disclosed herein. For example, such sterilization may occur via exposure to steam, UV light, or another form of sterilization, whether within an autoclave or another suitable apparatus. In some situations, the external energy store H2 is water-proof, water-tight, water-resistant, or another suitable anti-water configuration. For example, the external energy store H2 may be configured for use when diving in a body of water (e.g., within about 10 meters, about 25 meters, about 50 meters).

The external energy store H2 has a terminal (e.g., electrical, mechanical) that allows for the external energy store H2 to provide an amount of energy when activated, as disclosed herein. The external energy store H2 has a portion hosting the terminal, where the portion is configured (e.g., sized, shaped, constituted) for entry into or exit from the first end portion of the handle H1 and containment within the first compartment of the handle H1 when the handheld unit 100 or the handheld unit 200 is used. In some situations, the first compartment of the handle H1 may have a means for engaging with the portion of the external energy store H2 to secure the portion of the external energy store H2 therein such that the external energy store H2 does not fall out from the first compartment of the handle H1 through the first end portion of the handle H1, thereby enable the external energy store H2 to continuously provide the amount of energy when the handheld unit 100 or the handheld unit 200 is in use. For example, the means may include a lock, a magnet, a snap, a latch, a catch, a hook, a hook-and-loop, a eyelet, a screw, a bolt, a nail, a button, a lever, an adhesive, a mating interface, a suction cup, or another suitable means. For example, the first compartment of the handle H1 may have a socket that is threaded (similar to an Edison socket) and the external energy store H2 may have the portion or the terminal being threaded (similar to an Edison screw) or vice versa, where the portion or the terminal of the external energy store H2 may thread into or from the socket within the first compartment of the handle H1 or vice versa.

As shown in FIG. 3, the horizontal plane along which the external energy store H2 longitudinally extends and the horizontal plane along which the handle H1 extends may be one common horizontal plane. Likewise, the axis of symmetry or the axis of rotation along which the external energy store H2 longitudinally extends and the axis of symmetry or the axis of rotation along which the handle H1 extends may be one common axis of symmetry or axis of rotation. For example, the portion of the external energy store H2 may be configured to concentrically nest within the first compartment of the handle H1, although this modality is not required and other forms of containment of the portion of the external energy store H2 within the first compartment of the handle H1 are possible.

The circuit board H3 may be a printed circuit board (PCB) that hosts a set of circuitry to operate or control the handheld unit 100 (including its internal components) or the handheld unit 200 (including its internal components), as disclosed herein. For example, the circuit board H3 may include a circuit, an amplifier, a switch, a transistor, a semiconductor, a controller, or other relevant electrical components to enable operation or control of the handheld unit 100 or the handheld unit 200. For example, the circuit board H3 may operate or control via or with a wireless communication interface, as disclosed herein. For example, such operation or control may occur external or off the handheld unit 100 or the handheld unit 200. For example, a user (e.g., a nurse, a doctor, a technician) may use a user input device (e.g., a cursor control device, a mouse, a touchpad, a trackball, a keyboard) connected (e.g., wired, wireless, waveguide) to or a component of a computing terminal, as disclosed herein, to control features or abilities of the handheld unit 100 or the handheld unit 200, as disclosed herein. The circuit board H3 extends within inner section of the handle H1 between the first compartment of the handle H1 and the second compartment of the handle H1 between the top side and the bottom side. The circuit board H3 extends within the inner section of the handle H1 between the first end portion of the handle H1 and the second end portion of the handle H1. In some situations, the circuit board H3 may extend within the first compartment of the handle H1 or the second compartment of the handle H1.

The control panel H4 is a user interface that allows for control of various components of the handheld unit 100 or the handheld unit 200, as disclosed herein. The control panel H4 may be virtual or physical. When control panel H4 is virtual, the control panel H4 has a touchscreen (e.g., monochrome, color, LCD, plasma, electrophoretic) with a set of virtual user input elements, such as a button, a switch, a lever, a dial, a knob, or another suitable virtual user input element. When the control panel H4 is physical, the control panel H4 has a set of physical user input elements, such as a button, a switch, a lever, a dial, a knob, or another suitable physical user input element. For example, when the control panel H4 is physical, the control panel H4 may constitute rubber, plastic, or silicone, but can constitute other suitable materials. For example, the control panel H4 may constitute metal, alloy, or other suitable materials, whether natural or synthetic.

Regardless of how the control panel H4 is manifested, the control panel H4 is configured for or constituted of such materials that are safe for sterilization, which may be performed via heat, chemicals, radiation, or other suitable processes, whether before or after scoping, as disclosed herein. For example, such sterilization may occur via exposure to steam, UV light, or another form of sterilization, whether within an autoclave or another suitable apparatus. In some situations, the control panel H4 is water-proof, water-tight, water-resistant, or another suitable anti-water configuration. For example, the control panel H4 may be configured for use when diving in a body of water (e.g., within about 10 meters, about 25 meters, about 50 meters).

The control panel H4 is electrically connected to the circuit board H3, as shown in FIG. 3. As such, the control panel H4 enables manual control of power (e.g., turn on and turn off, activate and deactivate), light intensity (e.g., more or less), light color (e.g., visible, infrared, black), zooming in or out, and other features, as disclosed herein. The control panel H4 is embedded into or extends on or along the top side of the handle H1, although the control panel H4 can also be embedded into or extend on or along the bottom side (or lateral side) of the handle H1. As such, the circuit board H3 may extend within the inner section of the handle H1 between the control panel H4 and the bottom side or vice versa.

The internal energy store H5 is a store of energy (e.g., chemical, electrical, mechanical, thermal). For example, the store of energy may be a battery (e.g., AA, AAA, coin cell), an energy cell, a capacitor, a spring, a heat pack, or another suitable energy form factor, whether rechargeable or non-rechargeable. The internal energy store H5 is connected, embedded in, hosted by, or extends from the circuit board H3. The internal energy store H5 is sufficiently energy dense to solely and simultaneously power all operations of the handheld unit 100 or the handheld unit 200, as disclosed herein, for a period of time. For example, the period of time may be about 5 minutes or under, about 10 minutes or under, about 15 minutes or under, about 20 minutes or under, about 25 minutes or under, about 30 minutes or under, about 60 minutes or under, about 120 minutes or under, about 180 minutes or under, or another suitable time period. For example, the period of time may be from about 0 hours to about 10 hours, depending on power needs and the store of energy. The internal energy store H5 extends between (i) the circuit board H3 and the bottom side of the handle H1, (ii) the control panel H4 and the bottom side of the handle H1, or (iii) the first end portion of the handle H1 and the second end portion of the handle H1, although this configuration is not required. For example, the internal energy store H5 may extend between the control panel H4 and the circuit board H3.

The internal energy store H5 may be recharged on-demand by the external energy store H2 being plugged into the handle H1 by the user, as disclosed herein. When the external energy store H2 is depleted, the external energy store H2 may be unplugged from the handle H1 (e.g., by pulling the external energy store H2 away from the handle H1) by the user and substituted on-demand with another external energy store H2 being plugged into the handle H1 by the user. This process may be repeated by the user, limited by availability of charged external energy stores H2. As such, this configuration enables hot-swapping of the external energy store H2 from the handle H1 while the handheld unit 100 or the handheld unit 200 is used, as disclosed herein, which enables continuity of use of the handheld unit 100 or the handheld unit 200 longer than the internal energy store H5 alone without recharging. For example, if the internal energy store H5 is close to depletion during a procedure involving the handheld unit 100 or the handheld unit 200, then the procedure is not halted until the handheld unit 100 or the handheld unit 200 is powered by another energy source, but instead the procedure is continued, since the external energy store H2 may be plugged into handle H1 by the user to recharge the internal energy store H5 and then hot-swapped again by the user with another external energy store H2 if the external energy store H2 is depleted when recharging the internal energy store H5. Therefore, the handheld unit 100 may host the external energy store H2 to charge the internal energy store H5 such that the external energy store H2 is hot-swappable from the handheld unit 100 by the user as the wireless communication interface of the computing terminal 300 receives the imagery of the cavity captured via the scope powered by the internal energy store H5 when the scope extends within the cavity as the user holds the handle H1 outside the cavity. The handle H1 may host the internal energy store H5 and the external energy store H2 simultaneously. The handle H1 has a portion extending between the scope and the second external store H2, where the portion hosts the control panel H4 for the user to control the scope and where the internal energy store H5 powers the control panel H4 as the wireless communication interface of the computing terminal 300 receives the imagery of the cavity captured via the scope powered by the internal energy store H5 when the scope extends within the cavity as the user holds the handle H1 outside the cavity. The handle H1 and the external energy store H2 are sterilizable when the handle H1 hosts the external energy store H2. The base D1 may have having a set of charging terminals capable of charging the external energy store when H2 the external energy store H2 is docked in the base D1. The set of charging terminals is capable of charging the external energy store H2 when the external energy store H2 is docked in the base D1.

The charging interface H6 (e.g., a male interface, a female interface, a fastening interface, a magnetizing interface) is configured to engage (e.g., mechanically, electrically, chemically, thermally, magnetically) with the external energy store H2 to enable the external energy store H2 to recharge the internal energy store H5 via the charging interface H6, as disclosed herein. The charging interface H6 is connected to, extends from, hosted by, or embedded with the circuit board H3 to enable the external energy store H2 to recharge the internal energy store H5 via the charging interface H6, as disclosed herein. For example, the charging interface H6 may longitudinally extend (e.g., rectilinearly, non-rectilinearly, arcuate, sinusoidal) from the circuit board H3. The charging interface H6 may include an insulating material, which include an electrically insulating material, a heat insulating material, or another suitable material. For example, the charging interface H6 may be a Universal Serial Bus (USB) interface, a USB-C interface, a Thunderbolt interface, or another suitable interface, whether propriety or open-source. As such, the portion of the external energy store H2 can mechanically connect with the charging interface H6 when the portion of the external energy store H2 is inserted into the first compartment of the handle H1 via the first end portion of the handle H1. Likewise, the portion of the external energy store H2 can electrically connect with the charging interface H6 when the portion of the external energy store H2 is inserted into the first compartment of the handle H1 via the first end portion of the handle H1. Therefore, when the portion of the external energy store H2 is mechanically and electrically connected to the charging interface H6, as disclosed herein, the external energy store H2 can begin to recharge the internal energy store H5 via the terminal of the portion of the external energy source H2 and the charging interface H6, which may be automatic, although manual activation of recharging of the internal energy store H6 is possible (e.g., via the control panel H4).

In some situations, the charging interface H6 is configured for or constituted of such materials that are safe for sterilization, which may be performed via heat, chemicals, radiation, or other suitable processes, whether before or after scoping, as disclosed herein. For example, such sterilization may occur via exposure to steam, UV light, or another form of sterilization, whether within an autoclave or another suitable apparatus. In some situations, the charging interface H6 is water-proof, water-tight, water-resistant, or another suitable anti-water configuration. For example, the charging interface H6 may be configured for use when diving in a body of water (e.g., within about 10 meters, about 25 meters, about 50 meters).

The scope interface H7 (e.g., a male interface, a female interface, a fastening interface, a magnetizing interface) is configured to engage (e.g., mechanically, electrically, chemically, thermally, magnetically) with a scope of the handheld unit 100 or the handheld unit 200, as disclosed herein, to enable various scoping functionality, as disclosed herein. The scope interface H7 is connected to, extends from, hosted by, or embedded with the circuit board H3 to enable various scoping functionality, as disclosed herein. For example, the scope interface H7 may longitudinally extend (e.g., rectilinearly, non-rectilinearly, arcuate, sinusoidal) from the circuit board H3. The scope interface H7 may include an insulating material, which include an electrically insulating material, a heat insulating material, or another suitable material. For example, the scope interface H7 may be a Universal Serial Bus (USB) interface, a USB-C interface, a Thunderbolt interface, or another suitable interface, whether propriety or open-source. The scope interface H7 is powered by the internal energy store H5. The circuit board H7 extends between the charging interface H6 and the scope interface H7. For example, the circuit board H7 spans between the charging interface H6 and the scope interface H7. Although the circuit board H7 extends between the scope interface H7 and the internal energy store H5, this configuration is not required and the scope interface H7 and the internal energy store H5 can be connected or deposited on one side of the circuit board H7. The charging interface H6 and the scope interface H7 may be of same gender (e.g., each being male or female) or of different genders (e.g., one is male and one is female).

In some situations, the scope interface H7 is configured for or constituted of such materials that are safe for sterilization, which may be performed via heat, chemicals, radiation, or other suitable processes, whether before or after scoping, as disclosed herein. For example, such sterilization may occur via exposure to steam, UV light, or another form of sterilization, whether within an autoclave or another suitable apparatus. In some situations, the scope interface H7 is water-proof, water-tight, water-resistant, or another suitable anti-water configuration. For example, the scope interface H7 may be configured for use when diving in a body of water (e.g., within about 10 meters, about 25 meters, about 50 meters).

The gyroscope or the accelerometer H8 enables a maintenance of horizon when rotating or tilting the handle H1 for purposes of image stabilization or orientation, as disclosed herein. The gyroscope or the accelerometer H8 is connected to, extends from, hosted by, or embedded with the circuit board H3 to enable the maintenance of a horizon when rotating or tilting the handle H1 for purposes of image stabilization or orientation, as disclosed herein. For example, the gyroscope or the accelerometer H8 enables or may be used for determining or maintaining a true horizon. For example, this configuration may allow rotating a remote visual presentation (e.g., on the computing terminal 300) as the tip portion rotates to keep the horizon level. The gyroscope or the accelerometer H8 is powered by the internal energy store H5. The gyroscope or the accelerometer H8 extends within the inner section between the first end portion of the handle H1 and the second end portion of the handle H1. The gyroscope or the accelerometer H8 extends within the inner section between the first compartment of the handle H1 and the second compartment of the handle H1. Although the gyroscope or the accelerometer H8 extends between the circuit board H3 and the bottom side, this configuration is not required and the gyroscope or the accelerometer H8 can extend between the circuit board H3 and the control panel H4, which may occur when the control panel H4 is embedded into or extends on or along the top side of the handle H1. Therefore, the handle H1 may host the gyroscope or the accelerometer H8, wherein the internal energy store H5 powers the gyroscope or the accelerometer H8 such that a horizon is maintained when the handheld unit 100 or the handle H1 is rotated or tilted. Note that the gyroscope or the accelerometer H8 may enable an ability to detect a rotational degree of the handheld unit 100 or the handheld unit 200 in addition to maintaining horizon/auto-orientation (when using a non zero degree lens), as disclosed herein.

The processor H9 enables various operations of the handheld unit 100 or the handheld unit 200, as disclosed herein. The processor H9 is connected to, extends from, hosted by, or embedded with the circuit board H3 to enable various operations of the handheld unit 100 or the handheld unit 200, as disclosed herein. The processor H9 is powered by the internal energy store H5. The processor H9 may be electrically or logically connected to the external energy store H2, the circuit board H3, the control panel H4, the internal energy store H5, the charging interface H6, the scope interface H7, the gyroscope or the accelerometer H8, the wireless communication interface H10, or the microphone H11, which enable control of any of foregoing. The processor H9 may be a single core processor, a multi-core processor, a controller, a central processing unit (CPU), a graphics processing unit (GPU), a tensor processing unit (TPU), a programmable logic controller (PLC), or another suitable processing form factor. The processor H9 extends within the inner section of the handle H1 between the first compartment of the handle H1 and the second compartment of the handle H1. The processor H9 extends within the inner section of the handle H1 between the first end portion of the handle H1 and the second end portion of the handle H1. Although the processor H9 extends between the circuit board H3 and the control panel H4, this configuration is not required and the processor H9 may extend between the circuit board H3 and the bottom side.

The wireless communication interface H10 may include a transmitter, a receiver, or a transceiver that enables various wireless communications, as disclosed herein. For example, such wireless communications may include sending of scoped imagery (e.g., streaming), audio content (e.g., streaming), or other content (e.g., settings). The wireless communication interface H10 is connected to, extends from, hosted by, or embedded with the circuit board H3 to enable various wireless communications, as disclosed herein. The wireless communication interface H10 is powered by the internal energy store H5. For example, the wireless communication interface H10 may be a Wi-Fi wireless communication interface, a Li-Fi wireless communication interface, a Bluetooth wireless communication interface, or another suitable wireless communication interface, whether involving a personal, local, wide, satellite, or another type of network, whether proprietary or open-source. The wireless communication interface H10 extends within the inner section of the handle H1 between the first compartment of the handle H1 and the second compartment of the handle H1. The wireless communication interface H10 extends within the inner section of the handle H1 between the first end portion of the handle H1 and the second end portion of the handle H1. Although the wireless communication interface H10 extends between the circuit board H3 and the control panel H4, this configuration is not required and the wireless communication interface H10 may extend between the circuit board H3 and the bottom side.

The microphone H11 enables various voice controls and verbal annotation in real-time during procedures, as disclosed herein. The microphone H11 is connected to, extends from, hosted by, or embedded with the circuit board H3 to enable various voice controls and verbal annotation in real-time during procedures, as disclosed herein. The microphone H11 is powered by the internal energy store H5. The microphone H11 extends within the inner section between the first end portion of the handle H1 and the second end portion of the handle H1. The microphone H11 extends within the inner section between the first compartment of the handle H1 and the second compartment of the handle H1. Although the microphone H11 extends between the circuit board H3 and the bottom side, this configuration is not required and the microphone H11 can extend between the circuit board H3 and the control panel H4, which may occur when the control panel H4 is embedded into or extends on or along the top side of the handle H1. The handheld unit 100 or the handle H1 may host the microphone H11, where the wireless interface of the computing terminal 300 may receive an audio content from the user captured via the microphone H11 powered by the internal energy store H5 when the scope extends within the cavity as the user holds the handle H1 outside the cavity, where the audio content relates to the imagery of the cavity. In some situations, the microphone H11 is configured for or constituted of such materials that are safe for sterilization, which may be performed via heat, chemicals, radiation, or other suitable processes, whether before or after scoping, as disclosed herein. For example, such sterilization may occur via exposure to steam, UV light, or another form of sterilization, whether within an autoclave or another suitable apparatus. In some situations, the microphone H11 is water-proof, water-tight, water-resistant, or another suitable anti-water configuration. For example, the microphone H11 may be configured for use when diving in a body of water (e.g., within about 10 meters, about 25 meters, about 50 meters).

The base D1 includes a set of terminal slots (three shown in FIG. 3 although more or less are possible) that are configured to host (e.g., mechanically, electrically, magnetically, thermally) the set of external energy stores D2. During such hosting, the set of external energy stores D2 is charged or recharged, each independent of another, such that each external energy store D2 can be individually withdrawn from the base D1 independent of others and used as the external energy store H2 to charge or recharge the internal energy store H5, as disclosed herein, or hot-swap with the external energy store H2, as disclosed herein. Each external energy store of the set of external energy stores D2 may be identical to the external energy store H2, at least in being able to fit into the first end portion of the handle H1, extend within the first compartment of the handle H1, engage with the charging interface H6, charge or recharge the internal energy store H5, disengage from the charging interface H6, and be removable from the first compartment of the handle H1 and the first end portion of the handle H1.

Therefore, as disclosed herein, the handle H1 is enabled for sterilization (e.g., low temp hydrogen peroxide, autoclave), hot-swapping of energy stores, wireless streaming, multi-scope compatibility, ergonomic design and controls for power and light intensity controls, voice controls and verbal annotation in real-time during procedures, maintenance of horizon when rotating or tilting the handle H1 for purposes of image stabilization or orientation, operating in light intensity control mode, imagery controls for endoscopy camera system (e.g., exposure, white and color balance, light intensity), or Over-The-Air (OTA) firmware updates (e.g., cellular, 5G, Wi-Fi), while being compact and light weight (e.g., under one pound, one kilogram). Similarly, as disclosed herein, the charging dock 400 can store and charge multiple energy stores D2 simultaneously and independent of each other, where each energy store D2 can be charged or docked or withdrawn independent of other energy stores D2 in the charging dock 4000.

Figure 5:
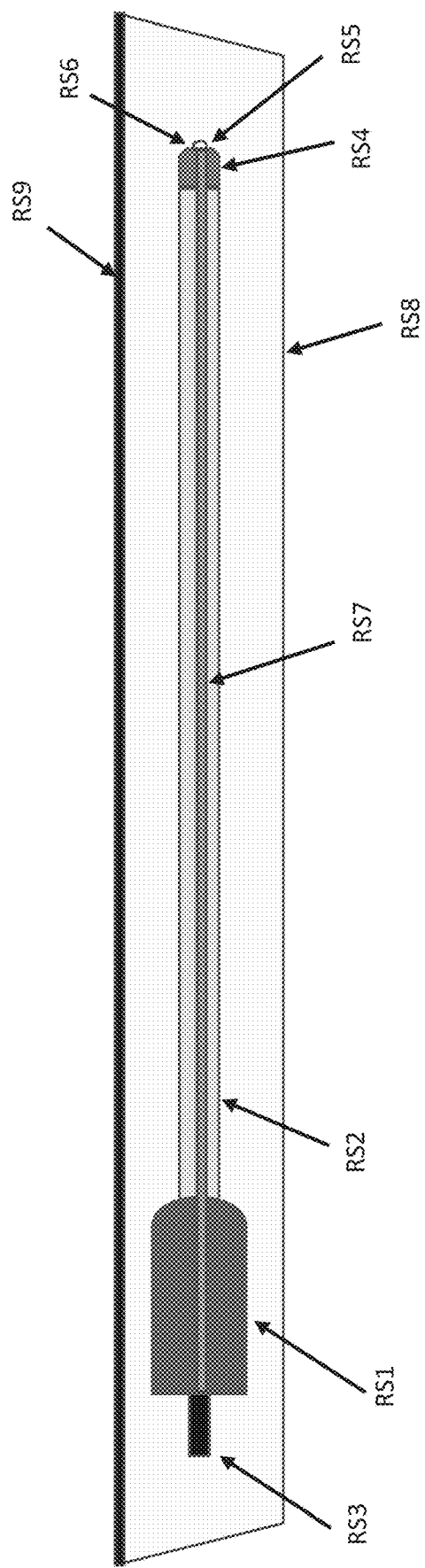
FIG. 5 shows a schematic diagram of an embodiment of a scope having a rigid section according to this disclosure.
Figure 6:
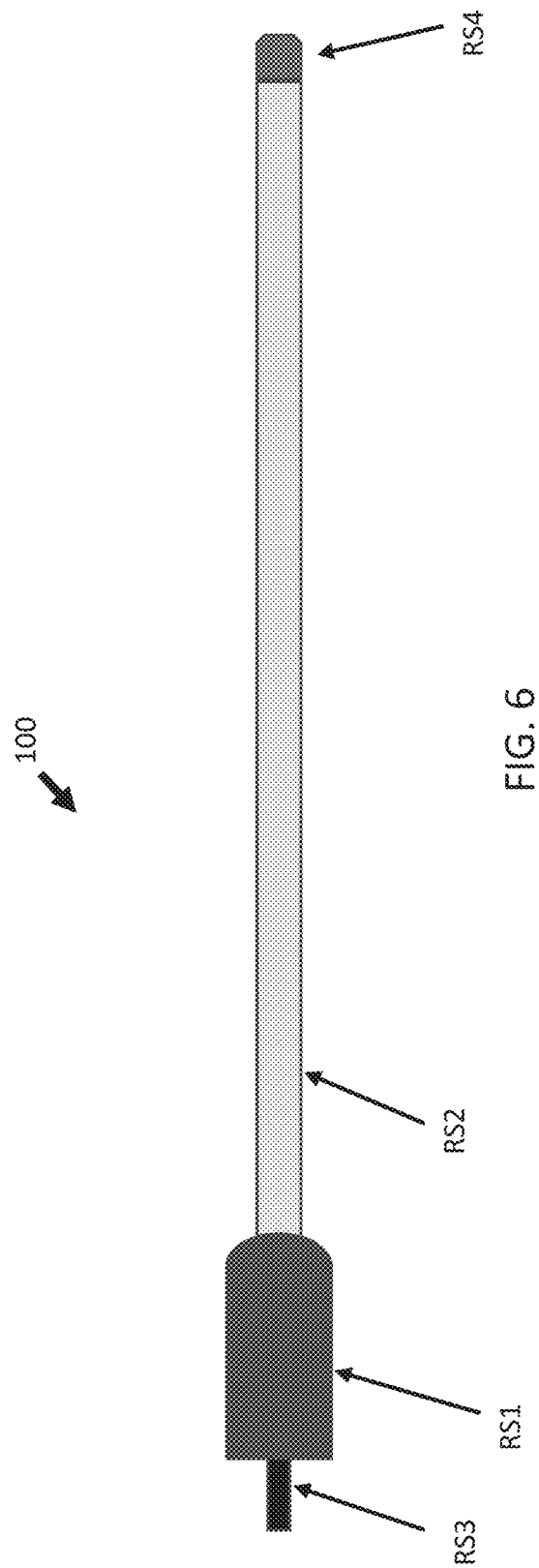
FIG. 6 shows a schematic diagram of an embodiment of a scope having a rigid section with a list of features thereof according to this disclosure.
Figure 7:
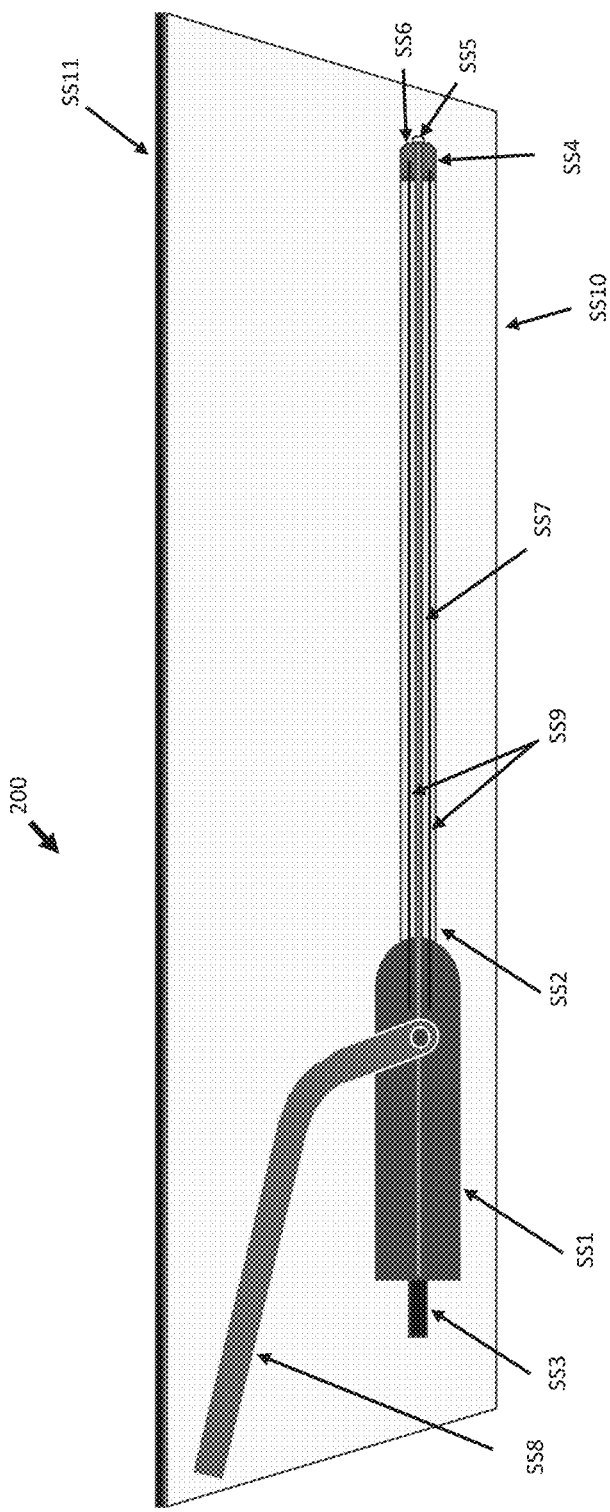
FIG. 7 shows a schematic diagram of an embodiment of a having a steerable section according to this disclosure.
Figure 8:
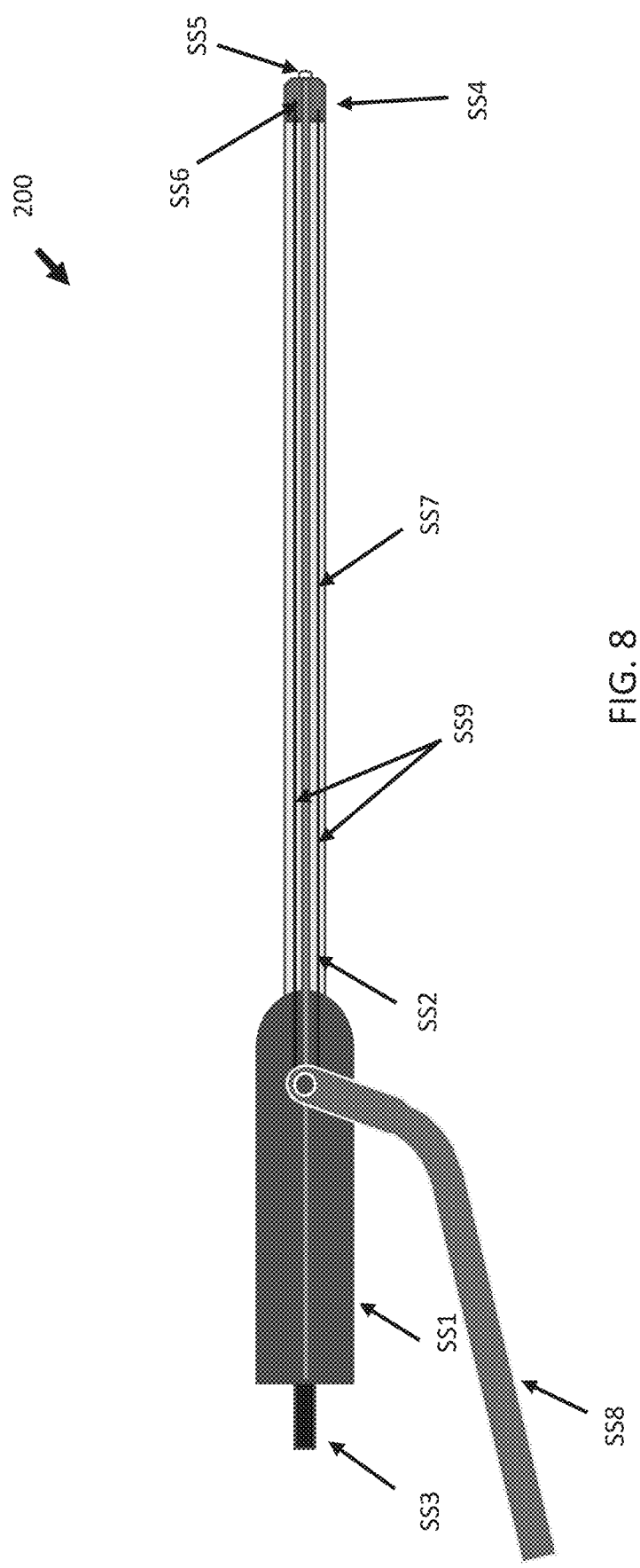
FIG. 8 shows a schematic diagram of an embodiment of a scope having a steerable section with a list of features thereof according to this disclosure.
Figure 9:
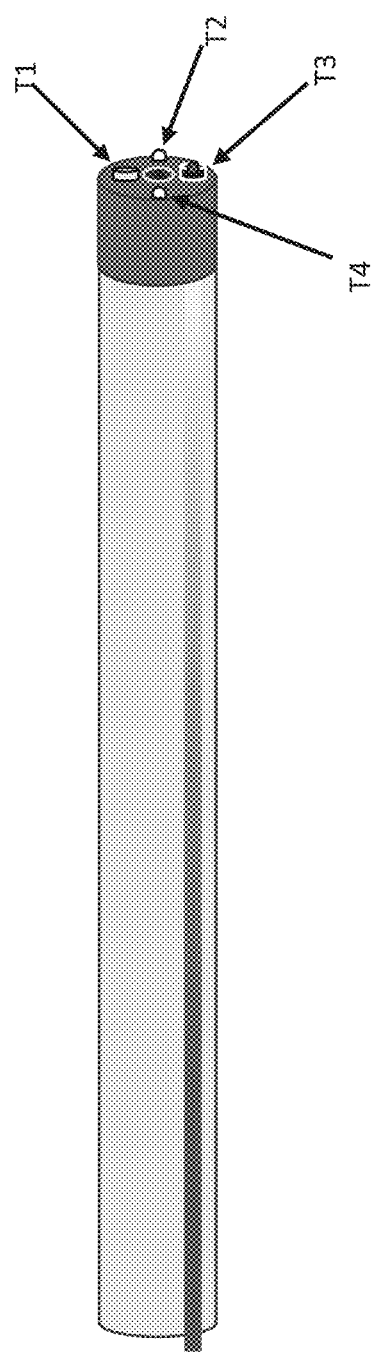
FIG. 9 shows a schematic diagram of an embodiment of a tip portion of a scope according to this disclosure.
Figure 10:
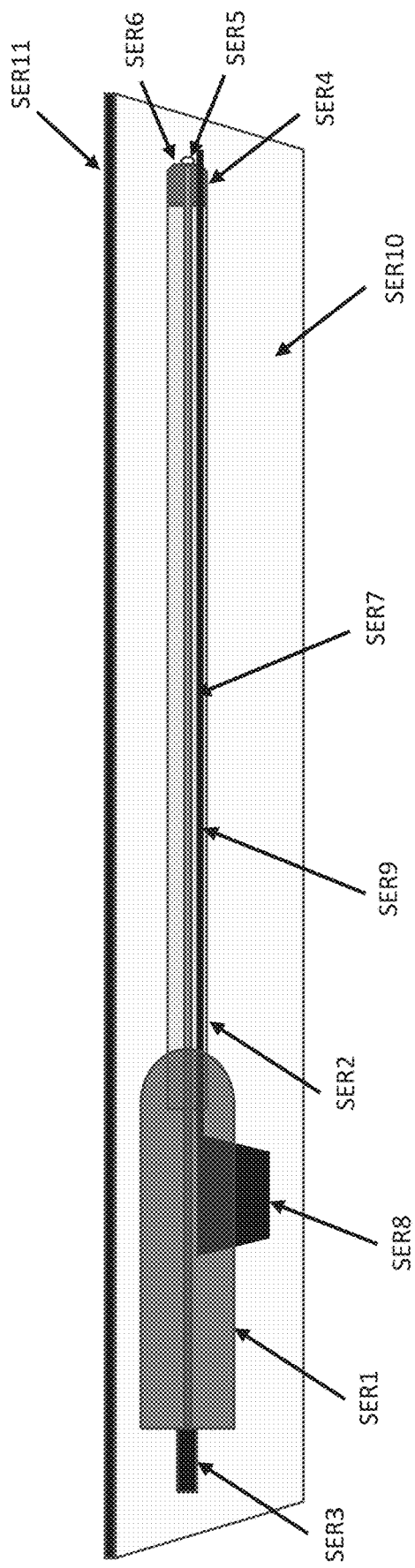
FIG. 10 shows a schematic diagram of an embodiment of a scope having a portion that is expandable or retractable according to this disclosure.

FIG. 5 shows a schematic diagram of an embodiment of a scope having a rigid section according to this disclosure. FIG. 6 shows a schematic diagram of an embodiment of a scope having a rigid section with a list of features thereof according to this disclosure. FIG. 7 shows a schematic diagram of an embodiment of a having a steerable section according to this disclosure. FIG. 8 shows a schematic diagram of an embodiment of a scope having a steerable section with a list of features thereof according to this disclosure. FIG. 9 shows a schematic diagram of an embodiment of a tip portion of a scope according to this disclosure. FIG. 10 shows a schematic diagram of an embodiment of a scope having a portion that is expandable or retractable according to this disclosure. FIGS. 11A-11D show a schematic diagram of an embodiment of a scope with a portion that is retractable, expandable, or capable of cutting or inputting or outputting a gas, a gel, a foam, a solid (e.g., a needle), or a liquid according to this disclosure. In particular, there is a scope having a connector RS1, a tube RS2, a handle interface RS3, a tip portion RS4, a sensor RS5, a light source RS6, and a line RS7. The scope is enclosed within a tray RS8 and covered by a cover RS9. The scope is detachably attachable to the handle H1 (or otherwise assembled therewith), although the scope may be monolithic with the handle H1.

The connector RS 1 is a housing, a case, or an enclosure from which the tube RS2 and the electrical interface RS3 extend. The connector RS1 is rectilinearly tubular in shape, but can be shaped differently. For example, the connector RS1 may be shaped as non-rectilinear, non-tubular, a puck, a sphere, a spheroid, a cube, a cuboid, an arc, a crescent, a pyramid, a cone, or another suitable shape, whether open-shaped or closed-shaped, whether symmetrical or asymmetrical. The connector RS1 may have a circular cross-section, although another suitable cross-section is possible (e.g., open-shaped, closed-shape, symmetrical, asymmetrical, square, rectangle, octagon, pentagon, triangle, trapezoid). The connector RS1 may include plastic, rubber, silicone, metal, alloy, or another suitable material. The connector RS1 may include an insulating material, which include an electrically insulating material, a heat insulating material, or another suitable material.

The connector RS1 extends (e.g., rectilinearly, non-rectilinearly, arcuate, sinusoidal) longitudinally along a plane. As shown in FIG. 5, the connector RS1 extends longitudinally along a horizontal plane, although this extension can vary depending on how the connector RS1 is oriented. For example, the connector RS1 can extend longitudinally along a vertical plane or a diagonal plane, depending on how the connector RS1 is oriented. Similarly, the connector RS1 extends longitudinally along an axis, whether an axis of symmetry or an axis of rotation. For example, the connector RS1 has a symmetrical shape along the horizontal plane, although this shaping may vary and the connector RS1 may have an asymmetrical shape along the horizontal plane, the vertical plane, or the diagonal plane.

The tube RS2 extends (e.g., rectilinearly, non-rectilinearly, arcuate, sinusoidal) from the connector RS1. For example, the tube RS2 cantileveredly extends from the connector RS1. The tube RS2 may be assembled with the connector RS1 (e.g., fastening, mating, bonding, molding, magnetizing) or monolithic with the connector RS1. The tube RS2 may have a single lumen or a set of lumens, which may extend (e.g., span) parallel to each other between the connector RS1 and the tip RS4. The tube RS2 may have a circular cross-section, although another suitable cross-section is possible (e.g., open-shaped, closed-shape, symmetrical, asymmetrical, square, rectangle, octagon, pentagon, triangle, trapezoid). The tube RS2 may include plastic, rubber, silicone, metal, alloy, or another suitable material. The tube RS2 may include an insulating material, which include an electrically insulating material, a heat insulating material, or another suitable material. The tube RS2 may has a sidewall constituting transparent, translucent, or opaque material. The tube RS2 is rigid (e.g., unable to be manually bent without usage of any tools), but the tube RS2 can be flexible.

If the tube RS2 has the set of lumens, then some of those lumens may be configured (e.g., sized, shaped, constituted) for conveying an instrument (or tool) or a subject matter, whether away from the connector RS1 or towards the connector RS1, as disclosed herein. For example, the instrument (or tool) may include a needle, a forceps, a clamp, a bracket, a scalpel, a knife, a blade, a scissors, a stent, an implant, or another suitable device, whether for medical or non-medical purposes. In such situations, the connector RS1 may have a corresponding set of interior lumens co-aligned with the set of lumens through which the instrument or the subject matter can pass.

The tube RS2 extends (e.g., rectilinearly, non-rectilinearly, arcuate, sinusoidal) longitudinally along a plane. As shown in FIG. 5, the tube RS2 extends longitudinally along a horizontal plane, although this extension can vary depending on how the tube RS2 is oriented. For example, the tube RS2 can extend longitudinally along a vertical plane or a diagonal plane, depending on how the tube RS2 is oriented. Similarly, the tube RS2 extends longitudinally along an axis, whether an axis of symmetry or an axis of rotation. For example, the tube RS2 has a symmetrical shape along the horizontal plane, although this shaping may vary and the tube RS2 may have an asymmetrical shape along the horizontal plane, the vertical plane, or the diagonal plane. The connector RS1 and the tube RS2 may extend along the horizontal plane and may share the axis, whether the axis of symmetry or the axis of rotation.

The handle interface RS3 extends (e.g., rectilinearly, non-rectilinearly, arcuate, sinusoidal) from the connector RS1. For example, the handle interface RS3 cantileveredly extends from the connector RS1. For example, the handle interface RS3 may extend in a first direction from the connector RS1 and the tube RS2 may extend in a second direction from the connector RS1, where the first direction is opposite the second direction, although perpendicular, acute or obtuse orientation is possible.

The handle interface RS3 may be assembled with the connector RS1 (e.g., fastening, mating, bonding, molding, magnetizing) or monolithic with the connector RS1. The handle interface RS3 may have a circular cross-section, although another suitable cross-section is possible (e.g., open-shaped, closed-shape, symmetrical, asymmetrical, square, rectangle, octagon, pentagon, triangle, trapezoid). The handle interface RS3 may include plastic, rubber, silicone, metal, alloy, or another suitable material. The handle interface RS3 may include an insulating material, which include an electrically insulating material, a heat insulating material, or another suitable material.

The handle interface RS3 extends (e.g., rectilinearly, non-rectilinearly, arcuate, sinusoidal) longitudinally along a plane. As shown in FIG. 5, the handle interface RS3 extends longitudinally along a horizontal plane, although this extension can vary depending on how the handle interface RS3 is oriented. For example, the handle interface RS3 can extend longitudinally along a vertical plane or a diagonal plane, depending on how the handle interface RS3 is oriented. Similarly, the handle interface RS3 extends longitudinally along an axis, whether an axis of symmetry or an axis of rotation. For example, the handle interface RS3 has a symmetrical shape along the horizontal plane, although this shaping may vary and the handle interface RS3 may have an asymmetrical shape along the horizontal plane, the vertical plane, or the diagonal plane. The connector RS1 and the handle interface RS3 may extend along the horizontal plane and may share the axis, whether the axis of symmetry or the axis of rotation.

The tube RS2 has the tip portion RS4 distal to the connector RS1. The tip portion RS4 is molded, but can be non-molded. For example, the tip portion RS4 may include plastic, rubber, silicone, metal, alloy, or another suitable material. The tip portion RS4 hosts the sensor RS5. For example, the sensor RS5 is a Complementary Metal-Oxide-Semiconductor (CMOS), which enables a camera or an image capture functionality, whether optical, infrared, or another suitable modality. For example, the light source can be embodied as a Light Emitting Diode (LED). The tip portion RS4 hosts the light source RS6 to output illumination for the camera or the image capture modality.

The tube hosts the line RS7 extending (e.g., spanning) between the handle interface RS3 and the tip portion RS4. For example, the line RS7 can include a cable, a ribbon, a fiber optic strand, a wire, or another suitable linear form factor, whether rectilinear or non-rectilinear (e.g., arcuate, sinusoidal). The line RS7 enables power and communication (e.g., controls, data, imagery) between the handle interface RS3 and the tip portion RS4, as disclosed herein. Since the tip portion RS4 hosts the sensor RS5 and the light source RS6, each whether single or many, the line RS7 enables such power and such communication (e.g., controls, data, imagery) between the handle interface RS3 and the sensor RS5 or the light source RS6, as disclosed herein. For example, such power may be sourced from the internal energy store H5 to the handle interface RS3, as disclosed herein. Likewise, such communication may be sourced from the circuit board H3 or the processor H9, as disclosed herein.

As shown in FIG. 5, the scope includes the connector RS1, the tube RS2, the handle interface RS3, the tip portion RS4, the sensor RS5, the light source RS6, and the line RS7. The scope is enclosed within the tray RS8 and covered by the cover RS9. The tray RS8 may be a container (e.g., U-shaped, V-shaped, C-shaped) that may contain the scope, whether before the procedure or after the procedure. The tray RS8 may constitute a transparent, translucent, or opaque material, whether plastic, rubber, metal, alloy, or another suitable material. Correspondingly, the tray RS8 is covered by the cover RS9, which may slide over the tray RS8, hinge from the tray RS8, whether laterally or from either end portion thereof, snap on/off from the tray RS8, or otherwise connect or attach to or freely rest on the tray RS8 to cover the tray RS8, at least for hygienic purposes. The cover RS9 constitute a transparent, translucent, or opaque material, whether plastic, rubber, metal, alloy, or another suitable material.

Therefore, as disclosed herein, the scope is enabled to host a chip-on-tip endoscope, have a multi-lumen tube of rigid material enabled for insertion/withdrawal of an instrument (or tool) or a subject matter therethrough, include solid wires bonded in lumens for added stiffness, be single use or reusable, be sterilizable, host a CMOS sensor and a LED light source on tip, be powered and controlled by the handle (e.g., onboard energy store), host mechanical and electrical interfaces at an end portion proximal to the handle H1, be able to suction and pump gas (e.g., CO2) or another fluid (e.g., liquid or gas) or foam or gel to maintain pneumoperitoneum (in conjunction with pressure sensor), host positive or negative (e.g., suction) pressure pump can be housed in the handle H1 powered by on-board energy store or be off the handle H1 and powered by on-board energy store or another power source (e.g., mains electricity, battery). Note that a solid (e.g., an instrument, a tool, a needle, a forceps, a blade, a scalpel, a knife, a clamp, an implant) may also be input or output, as disclosed herein.

FIGS. 7-8 show a scope that is similar to the scope shown in FIGS. 5-6. In particular, FIGS. 7-8 show the scope having a connector SS1, a tube SS2, a handle interface SS3, a tip portion SS4, a sensor SS5, a light source SS6, a line SS7, a lever SS8, and a set of pull wires SS9. The scope shown in FIGS. 7-8 is stored in a tray SS10 covered by a cover SS1. The connector SS1 is similar to the connector RS1. The tube SS2 is similar to the tube RS2. The handle interface SS3 is similar to the handle interface RS3. The tip portion SS4 is similar to the tip portion RS4. The sensor SS5 is similar to the sensor RS5. The light source SS6 is similar to the light source RS6. The line SS7 is similar to the line RS7. The tray RS8 is similar to the tray SS10. The cover SS11 is similar to the cover RS9. However, the scope shown in FIGS. 7-8 differs from the scope shown in FIGS. 5-6 by the scope shown in FIGS. 7-8 having the lever SS8 and the set of pull wires (or lines) SS9.

The lever SS8 is pivotally attached to the connector SS1. For example, such pivotal attachment may be via a pin extending through the lever SS8 and the connector SS1, or via the lever SS8 having a horn or a pair of horns extending into the connector SS1, or via the connector SS1 having a horn or a pair of horns extending into the lever SS8, or another suitable pivotal attachment. As such, the lever SS8 is configured to pivot towards or away from the connector SS1 or the handle H1 when the handle interface SS3 engages the scope interface H7, as disclosed herein. The lever SS8 is J-shaped, but can be shaped differently, whether L-shaped, I-shaped, D-shaped, O-shaped, 0-shaped, S-shaped, U-shaped, C-shaped, V-shaped, arcuate, crescent, or another suitable shape. The lever SS8 constitutes plastic, but can constitute another suitable material (e.g., metal, alloy, rubber, silicone).

In some situations, the lever SS8 is configured for or constituted of such materials that are safe for sterilization, which may be performed via heat, chemicals, radiation, or other suitable processes, whether before or after scoping, as disclosed herein. For example, such sterilization may occur via exposure to steam, UV light, or another form of sterilization, whether within an autoclave or another suitable apparatus. In some situations, the lever SS8 is water-proof, water-tight, water-resistant, or another suitable anti-water configuration. For example, the lever SS8 may be configured for use when diving in a body of water (e.g., within about 10 meters, about 25 meters, about 50 meters).

The set of pull wires SS9 extends (e.g., spans) between the lever and the tip portion SS4. For example, each wire in the set of pull wires SS9 may be attached (e.g., assembled, fastened, bonded, mated, interlocked, monolithic) to the lever SS8 on one end and the tip portion SS4 on another end. Each wire in the set of pull wires SS9 may include metal, alloy, plastic, rubber, silicone, fabric, yarn, or another suitable material, whether flexible or rigid. As such, when the tube SS2 is flexible, the lever SS8 may be pivoted such that the set of wires SS9 is selectively pulled based on pivoting to the lever SS8 to steer the tube SS2 (similar to a trunk of an elephant). Such steering may be along a single plane (e.g., horizontal, vertical, diagonal), two planes (e.g., horizontal, vertical, diagonal), or three planes (e.g., horizontal, vertical, diagonal).

As shown in FIG. 5, the scope may include the electrical interface RS3, the connector RS1, the tube RS2, and the line RS7, where the tube RS2 includes the tip portion RS4 distal to the connector RS1, where the electrical interface RS3 extends from the connector RS1, where the tube RS2 extends from the connector RS1, where the tip portion RS4 hosts the image sensor RS5 and the light source RS6, where the line RS7 extends within the tube RS2 between the electrical interface RS3 and the tip portion RS4 such that the image sensor RS5 and the light source RS6 are powered via the electrical interface RS3, where the internal energy store powers H5 the electrical interface RS3 when the scope extends within the cavity as the user holds the handle H1 outside the cavity. The electrical interface RS3 may extend from the connector RS1 in a first direction, where the tube RS2 extends from the connector RS 1 in a second direction, where the first direction is opposite the second direction. The tip portion RS4 may host a chip hosting the image sensor RS5 and the light source RS6. The tube RS2 may be rigid. The scope may include the channel TF1 extending within the tube RS2, where the channel TF1 includes an end portion, where the tip portion RS4 includes the end portion, where the end portion is open for an output of a subject matter into the cavity or an input of the subject matter from the cavity when the scope extends within the cavity as the user holds the handle H1 outside the cavity. As shown in FIGS. 11A-11D, the subject matter may include the instrument, the tool, the liquid, the gas, the gel, or the foam. The handheld unit 100 may host a device enabling the output or the input, where the internal energy store H5 powers the device when the scope extends within the cavity as the user holds the handle H1 outside the cavity, where the device includes a pump unit, an actuator unit, a motor unit, a pneumatic unit, a hydraulic unit, a pulley unit, a spool unit, a reel unit, or a winch unit. As shown in FIGS. 7-8, the scope may include the second line SS9, the third line SS8, and the lever SS8, where the lever SS8 is pivotably attached to the connector SS1, where the second line SS9 and the third line SS9 extend between the lever SS8 and the tip portion SS4 such that the tip portion SS4 is steerable (e.g., alone a single plane, two planes, three planes) via the lever SS8 when the scope extends within the cavity as the user holds the handle H1 outside the cavity. Therefore, as disclosed herein, the scope shown in FIGS. 7-8 is enabled for functionality of the scope shown in FIGS. 5-6 and, additionally, to have a steerable distal tip, steering via the handle H1 and guide wires in lumens of the tube SS2, steering in single plane, up to past about 180 degrees (+/−15 degrees) although multi-planar steering is possible with more parts for that (e.g., wires, actuators, motors, pulleys, hydraulics, pneumatics).

FIG. 9 shows a schematic diagram of an embodiment of a tip portion of a scope according to this disclosure. In particular, there is a scope of FIGS. 5-8 having a sensor T1, a light source T2, a fiber optic strand T3, and a nozzle T4.

The sensor T1 may be a temperature sensor (e.g., a thermometer), a pressure sensor, a haptic sensor, an optical sensor, an infrared sensor, a UV sensor, a sound sensor (e.g., a microphone), a distance sensor (e.g., a radar, a time-of-flight radar, a doppler radar), a motion sensor, a proximity sensor, a chemical sensor (e.g., a gas, a liquid), a CMOS sensor, or another suitable sensor, each whether single or many. The sensor T1 may be powered via the internal energy store H5, as disclosed herein, and controlled via the control panel H4, as disclosed herein.

The light source T2 may output a light of a single wavelength, a light of multiple wavelengths, a visible light, an infrared light, a UV light, or another suitable light. The light source T2 may be powered via the internal energy store H5, as disclosed herein, and controlled via the control panel H4, as disclosed herein. For example, the light source T2 may or may not be LED-based (e.g., incandescent, gas discharge).

The scope shown in FIGS. 5-8 may host the fiber optic strand T3 (e.g., the line RS7 or SS7). The fiber optic strand T3 may enable the sensor RS5 or SS5 to communicate imagery to the circuit board H3 or the processor H9, as disclosed herein. The fiber optic strand T3 may extend (e.g., span) between the handle interface RS3 or SS3 and the tip portion RS4 or SS4, which enables the handle interface RS3 or SS3 to send the imagery to the circuit board H3 or the processor H9, for further operations, as disclosed herein. Note that there fiber optic strand T3 may include a bundle of fiber optic strands T3.

The nozzle T4 enables an input or an output of a fluid (e.g., a liquid, a gas), a gel, a foam, a solid (e.g., an instrument, a tool, a needle, a forceps, a blade, a scalpel, a knife, a clamp, an implant), or another suitable subject matter from the handle H1 or to the handle H1. For example, there may be a pump, whether the handle H1 hosts the pump, whether internally or externally, or whether the pump is located off the handle H1, where the pump enables the input or the output of the fluid. The pump may be powered via the internal energy store H5, as disclosed herein, or controlled by the control panel H4, as disclosed herein.

In some situations, at least one, two, three, or four of the T1, T2, T3, or T4 is configured for or constituted of such materials that are safe for sterilization, which may be performed via heat, chemicals, radiation, or other suitable processes, whether before or after scoping, as disclosed herein. For example, such sterilization may occur via exposure to steam, UV light, or another form of sterilization, whether within an autoclave or another suitable apparatus. In some situations, the at least one, two, three, or four of the T1, T2, T3, or T4 is water-proof, water-tight, water-resistant, or another suitable anti-water configuration. For example, the at least one, two, three, or four of the T1, T2, T3, or T4 may be configured for use when diving in a body of water (e.g., within about 10 meters, about 25 meters, about 50 meters).

FIG. 10 shows a schematic diagram of an embodiment of a scope having a portion that is expandable or retractable according to this disclosure. FIGS. 11A-11D show a schematic diagram of an embodiment of a scope with a portion that is retractable, expandable, or capable of cutting or inputting or outputting a gas, a gel, a foam, a solid (e.g., a needle), or a liquid according to this disclosure. In particular, there is a scope having a connector SER1, a tube SER2, a handle interface SER3, a tip portion SER4, a sensor SER5, a light source SER6, a line SER7, an input element SER8, and a guide SER9. The scope shown in FIGS. 10-11 is stored in a tray SER10 covered by a cover SER11.

The connector SER1 is similar to the connector RS1 or SS1. The tube SER2 is similar to the tube RS2 or SS2. The handle interface SER3 is similar to the handle interface RS3 or SS3. The tip portion SER4 is similar to the tip portion RS4 or SS4. The sensor SER5 is similar to the sensor RS5 or SS5. The light source SER6 is similar to the light source RS6 or SS6. The line SER7 is similar to the line RS7 or SS7. The tray SER10 is similar to the tray RS8 or SS10. The cover SER11 is similar to the cover RS9 or SS11. However, the scope shown in FIGS. 10-11 differs from the scope shown in FIGS. 5-8 by the scope shown in FIGS. 10-11 having the input element SER8 and the guide SER9.

The input element SER8 may be a button, a lever, a switch, a rocker, a dial, a knob, or another suitable user input element, whether physical or virtual (e.g., on a display or a touchscreen when present). The connector SER1 hosts the input element SER8, which may avoid facing the cover SER11, although this configuration is not required and the input element SER8 may face the cover SER11. The input element SER8 may include plastic, rubber, silicone, metal, alloy or another suitable material. Although the SER8 is trapezoidal, this configuration is not required and the SER8 may be shaped differently (e.g., non-trapezoidal, cube, cuboid, oval, ovoid, spherical, pyramidal, conical, toroid, or another suitable shape, whether symmetrical or asymmetrical, whether open-shaped or closed-shaped.

In some situations, the input element SER8 is configured for or constituted of such materials that are safe for sterilization, which may be performed via heat, chemicals, radiation, or other suitable processes, whether before or after scoping, as disclosed herein. For example, such sterilization may occur via exposure to steam, UV light, or another form of sterilization, whether within an autoclave or another suitable apparatus. In some situations, the input element SER8 is water-proof, water-tight, water-resistant, or another suitable anti-water configuration. For example, the input element SER8 may be configured for use when diving in a body of water (e.g., within about 10 meters, about 25 meters, about 50 meters).

The guide SER9 is a line (e.g., a bar, a rod, a fiber, a wire, a cable, a chain, a fabric, a braid, a bundle) attached (e.g., cantileveredly) to the input element SER8. The guide SER9 extends within the tube SER2, which may be parallel to the line SER7, although this configuration is not required and non-parallel extension is possible. The tip portion SER4 may have an opening or a nozzle through which the guide SER9 may enter or exit, as controlled by the input element SER8 operated by the user. For example, the input element SER8 may be a switch that is moved or urged along or on the connector SER1 towards the tip portion SER4 or away from the tip portion SER4. Correspondingly, the input element SER8 may be pushed by the user toward the tip portion SER4 to enable the guide SER9 to expand or extend out of the opening of the tip portion SER4. Conversely, the input element SER8 may be pulled by the user away from the tip portion SER4 to enable the guide SER9 to retract or extend into the opening of the tip portion SER4.

In some situations, the guide SER9 is configured for or constituted of such materials that are safe for sterilization, which may be performed via heat, chemicals, radiation, or other suitable processes, whether before or after scoping, as disclosed herein. For example, such sterilization may occur via exposure to steam, UV light, or another form of sterilization, whether within an autoclave or another suitable apparatus. In some situations, the guide SER9 is water-proof, water-tight, water-resistant, or another suitable anti-water configuration. For example, the guide SER9 may be configured for use when diving in a body of water (e.g., within about 10 meters, about 25 meters, about 50 meters).

As shown in FIGS. 11A-11D, the tube SER2 has a channel (e.g., a lumen) TF1 leading to the opening or the nozzle at the tip portion SER4. The channel TF1 within the tube SER2 hosts the guide SER9 and enables the guide SER9 to travel (e.g., slidably) therein and to exit or enter the opening or the nozzle at the tip portion SER4. As shown in FIGS. 11A-11D, the guide SER9 is referenced by TF2.

The guide TF2 has an end portion distal to the input element SER8. The end portion of the guide TF2 may host an instrument (or tool) that is insertable into the channel TF1, can travel within the channel TF1 as guided by the guide TF2 controlled by the input element SER8, and lead exit or enter the opening or the nozzle at the tip portion SER4. As shown in FIGS. 11A-11D, the instrument (or tool) may be a medical instrument (or tool), such as a forceps or alligator tip TF3, a cold-cup biopsy unit TF4, a bovie type tip TF5 (e.g., an electrode, a molded electrode featuring a safety grip insulator), a needle TF6, a knife, a scalpel, a blade, a scissor, a heating element, or another suitable medical instrument. When the instrument (or tool) is used in non-medical purposes, then instrument (or tool) may be same or adapted accordingly. Also, if the guide TF2 has an lumen or a cavity, then the instrument may be a nozzle to input or output a subject matter, which may include a fluid, a gas, a liquid, a gas, a gel, a foam, or another suitable subject matter.

FIG. 12 shows a schematic diagram of an embodiment of a computing terminal according to this disclosure. FIG. 13 shows a schematic diagram of an embodiment of a computing terminal with a list of features thereof according to this disclosure. In particular, the computing terminal 300 includes an enclosure or a housing CT1, a power supply CT2, a fan CT3, a wireless networking interface CT4, a wired networking interface CT5, a motherboard CT6, a networking chipset CT7, a GPU CT8, a random access memory (RAM) CT9, an AI processing chipset CT10, a processor CT11, and a persistent memory CT12. For example, the computing terminal 300 may have a form factor of a desktop computer, a laptop computer, a smartphone, a wearable computer, a headgear computer, or another suitable computer.

The enclosure or housing CT1 (e.g., plastic, metal, rubber) encloses or houses the power supply CT2, the fan CT3, the wireless networking interface CT4, the wired networking interface CT5, the motherboard CT6, the networking chipset CT7, the GPU CT8, the RAM CT9, the AI processing chipset CT10, the processor CT11, and the persistent memory CT12. The power supply CT2 is configured to power the fan CT3, the wireless networking interface CT4, the wired networking interface CT5, the motherboard CT6, the networking chipset CT7, the GPU CT8, the RAM CT9, the AI processing chipset CT10, the processor CT11, and the persistent memory CT12. The power supply CT2 is powered by a battery or a cable coupled to the power supply CT2 and a socket (e.g., a wall socket of a main electricity source).

The fan CT3 (or a heat sink or another modality of thermal management) enables for thermal management generated from the power supply CT2, the wireless networking interface CT4, the wired networking interface CT5, the motherboard CT6, the networking chipset CT7, the GPU CT8, the RAM CT9, the AI processing chipset CT10, the processor CT11, or the persistent memory CT12.

The wireless networking interface CT4 may be a Wi-Fi interface, a Li-Fi interface, or another wireless networking interface, whether over a personal area network, a local area network, a wide area network, a satellite network, or another suitable network. The wireless networking interface CT4 may be configured to wirelessly communicate with the wireless networking interface H10 hosted by the handle H1.

The wired networking interface CT5 may be an HDMI interface, a USB interface, an ethernet interface, or another suitable networking interface.

The motherboard CT6 may be a PCB that hosts a set of circuitry to operate the computing terminal 300, as disclosed herein. For example, the motherboard CT6 may include a circuit, an amplifier, a switch, a transistor, a semiconductor, a controller, or other relevant electrical components to enable operation of the computing terminal 300.

Operably hosted, attached or connected to the motherboard CT6 is the networking chipset CT7 that enables the wireless networking interface CT4 to operate, the GPU CT8 that enables various video operations on the imagery received from the scope of the handheld unit 100 or the handheld unit 200, the RAM CT9 for the processor CT11, the AI processing chipset CT10 that enables various AI operations on the imagery received from the scope of the handheld unit 100 or the handheld unit 200, the processor CT11 that controls the power supply CT2, the fan CT3, the wireless networking interface CT4, the wired networking interface CT5, the motherboard CT6, the networking chipset CT7, the GPU CT8, the RAM CT9, the AI processing chipset CT10, or the persistent memory CT12. The persistent memory CT12 is configured to store information or serve information to the processor CT11. The AI processing chipset CT10 may be a hardware accelerator, a neural network accelerator, a machine learning accelerator, or another suitable accelerator. The processor CT11 may be a single core processor, a multicore processor, a system-on-chip, or another suitable processing unit.

As shown in FIGS. 3-11, the handle H1 and the scope may be assembled with each other by the user before the wireless communication interface of the computing terminal 300 receives the imagery of the cavity captured via the scope powered by the internal energy store H5 when the scope extends within the cavity as the user holds the handle D1 outside the cavity and disassembled from each other by the user after the wireless communication interface of the computing terminal 300 receives the imagery of the cavity captured via the scope powered by the internal energy store H5 when the scope extends within the cavity as the user holds the handle D1 outside the cavity. The handle H1 may have a portion extending between the scope and the external energy store H2, where the portion hosts the control panel H4 for the user to control the scope, where the internal energy store H5 powers the control panel H4 as the wireless communication interface of the computing terminal 300 receives the imagery of the cavity captured via the scope powered by the internal energy store H5 when the scope extends within the cavity as the user holds the handle D1 outside the cavity. The handle H1 has a portion extending between the scope and the external energy store H2, where the portion hosts the control panel H4 for the user to control the scope. The handle H1 may have a portion extending between the scope and the external energy store H2, where the portion hosts the control panel H4 for the user to steer the scope.

As shown in FIGS. 12-13, the computing terminal 300 may host the artificial intelligence (AI) processing chipset CT10 that processes the imagery of the cavity received by the wireless communication interface of the computing terminal when the scope extends within the cavity as the user holds the handle H1 outside the cavity. The computing terminal 300 may perform an image stabilization process on the imagery received by the wireless communication interface of the computing terminal 300 when the scope extends within the cavity as the user holds the handle H1 outside the cavity and maintains a point of reference to horizon on the imagery received by the wireless communication interface of the computing terminal 300 when the scope extends within the cavity as the user holds the handle H1 outside the cavity. The computing terminal 300 may include a display, where the computing terminal runs an artificial intelligence (AI) model on the imagery to enable a provision of an assistance to the user (e.g., a wizard, a guide) viewing the display when the scope extends within the cavity as the user holds the handle H1 outside the cavity, where the assistance is displayed on the display relating to the scope navigating the cavity.

Therefore, as disclosed herein, the computing terminal 300 is enabled to receive wireless stream from the handle H1, host standardized outputs for remote display (e.g., HDMI), host standardized USB (or another standard) inputs for peripheral devices (e.g., a physical mouse, a physical keyboard), provide automatic software image stabilization and maintenance of reference to horizon (gyro), allow for wireless or wired connection to an external router for internet (or another network access), process AI models in real-time on imagery from the handle H1 to provide assistance for select procedures (e.g., medical, non-medical), download AI models (e.g., new, update) from a cloud application with internal access through the external router, allow for OTA (e.g., Wi-Fi, cellular) firmware updates to itself or the handle H1, display a Graphical User Interface (GUI) on separate or integrated screen (all-in-one), which may be a touchscreen, allow for various imagery and data capture controls for the handheld unit 100 or the handheld unit 200, enable patient data file access or storage with seamless upload to an integrated cloud application with internet access, enable patient data file annotations and other editing capability (e.g., captured from microphone on the handle H1), which may allow for transcriptions and adding to electronic medical record (EMR), or enable live streaming of procedures for invited/authenticated viewers with internet access.

Figures 15A, 15B:
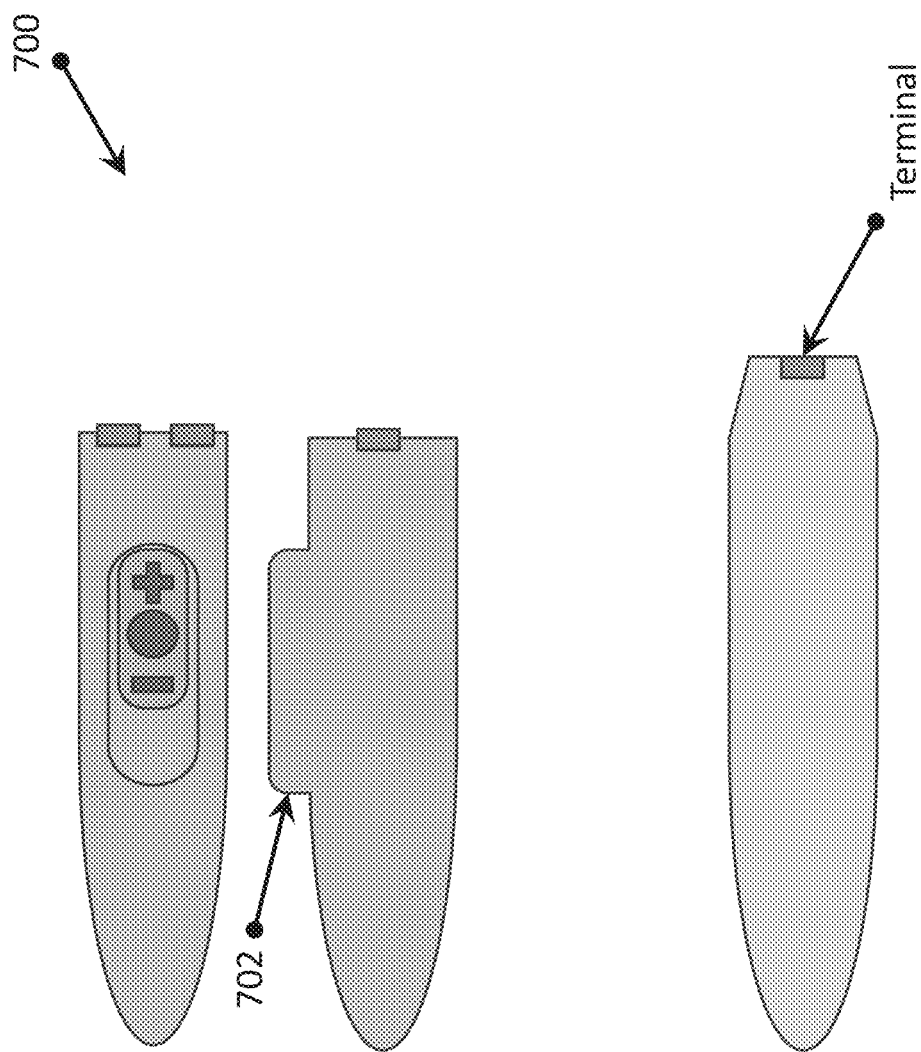
FIGS. 15A-15B show a schematic diagram of an embodiment of a power module according to this disclosure.
Figure 18:
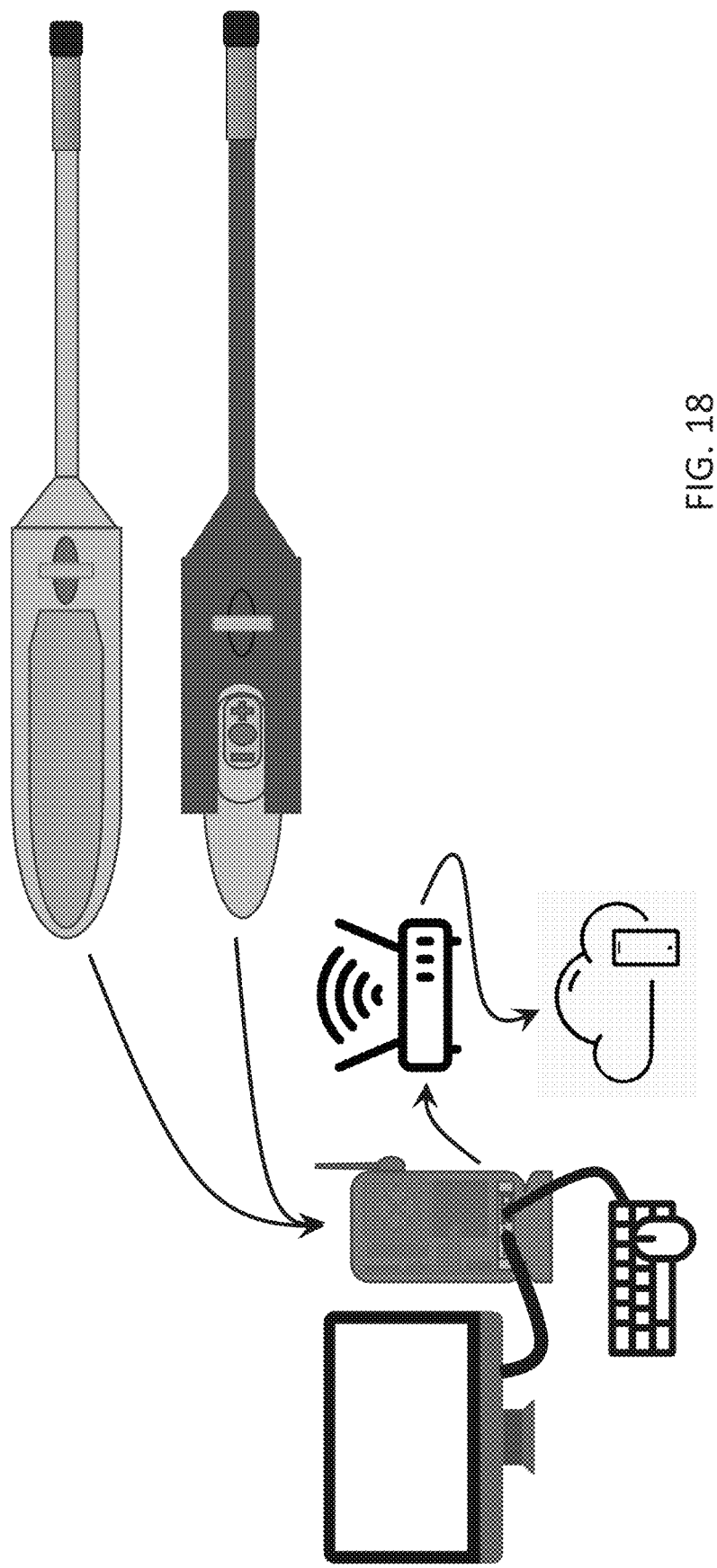
FIG. 18 shows a schematic diagram of an embodiment of a system or a kit being manufactured or used according to this disclosure.

FIGS. 14A-14B show a schematic diagram of an embodiment of a scope configured to receive a power module in a non-encapsulated manner and an embodiment of a handheld unit configured to receive a power module in an encapsulated manner according to this disclosure. FIGS. 15A-15B show a schematic diagram of an embodiment of a power module according to this disclosure. FIGS. 16A-16B show a schematic diagram of an embodiment of a scope in receipt of a power module in a non-encapsulated manner according to this disclosure. FIGS. 17A-17B show a schematic diagram of an embodiment of a handheld unit configured to receive a power module in an encapsulated manner according to this disclosure. FIG. 18 shows a schematic diagram of an embodiment of a system or a kit being manufactured or used according to this disclosure. In particular, there is a handheld unit 500, a handheld unit 600, and a power module 700. The power module 700 may be used in context of the handheld unit 500 or the handheld unit 600. The handheld unit 500 or the handheld unit 600 is similar to the handheld unit 100 or the handheld unit 200.

As shown in FIGS. 14A-14B and FIGS. 16A-16B, the handheld unit 500 includes a tube 502, a handle 504, a control panel 506, and a channel (or passage) 508. The tube 502 similar to the tube RS2 or SS2. The handle 504 is similar to the handle H1. However, unlike the handle H1, the handle 504 has a top side defining a slot (or a channel) 510 that is open, where the top side hosts the control panel 506, which is shown to be a physical control panel, although a virtual control panel is possible. For example, the slot 510 may have an open-shape, such as a U-shape, a C-shape, a V-shape, or another suitable shape. The tube 502 has a tip portion similar to the RS4 or the SS4 and the control panel 506 enables control thereof. For example, such control may enable steering of the tube 502 or the tip portion.

Although the tube 502 and the handle 504 are monolithic, this configuration is not required and the tube 502 and the handle 504 may be assembled (e.g., fastened, mated, magnetized, adhered) with each other. The tube 502 or the handle 504 constitutes plastic, but can constitute other suitable materials. For example, the tube 502 or the handle 504 may constitute metal, alloy, rubber, silicone, or other suitable materials, whether natural or synthetic. In some situations, the tube 502 or the handle 504 is configured for or constituted of such materials that are safe for sterilization, which may be performed via heat, chemicals, radiation, or other suitable processes, whether before or after scoping, as disclosed herein. For example, such sterilization may occur via exposure to steam, UV light, or another form of sterilization, whether within an autoclave or another suitable apparatus. In some situations, the tube 502 or the handle 504 is water-proof, water-tight, water-resistant, or another suitable anti-water configuration. For example, the tube 502 or the handle 504 may be configured for use when diving in a body of water (e.g., within about 10 meters, about 25 meters, about 50 meters).

As shown in FIGS. 14A-14B and FIGS. 17A-17B, the handheld unit 600 is similar to the handheld unit 500. However, the handheld unit 600 differs from the handheld unit 500 in that the handheld unit 600 has a handle 602 in a clamshell form factor. For example, the handle 602 may be a one-piece container having of two portions joined by a hinge (e.g., a butterfly hinge, a living hinge), which allows the container to come together for closing or to separate for opening. However, note that the hinge may be omitted and the two portions may detach or attach to one another in any suitable manner (e.g., snapping, magnetizing, fastening, mating, adhering). Note that the clamshell form factor may enable a reusable battery/sensor pack into a single-use disposable endoscope and allow this entire assembly.

When the handle 602 is closed, then the handle 602 is configured for or constituted of such materials that are safe for sterilization, which may be performed via heat, chemicals, radiation, or other suitable processes, whether before or after scoping, as disclosed herein. For example, such sterilization may occur via exposure to steam, UV light, or another form of sterilization, whether within an autoclave or another suitable apparatus. In some situations, the handle 604 is water-proof, water-tight, water-resistant, or another suitable anti-water configuration. For example, the handle 604 may be configured for use when diving in a body of water (e.g., within about 10 meters, about 25 meters, about 50 meters).

Each of the handheld unit 500 or the handheld unit 600 is configured to enable receipt or withdrawal of the power module 700, which is similar to the external energy store H2 or the internal energy store H5. The power module 700 is a housing, a case, or an enclosure that houses, encases, or encloses an energy cell or a set of energy cells, a processor, a wireless networking interface, a gyroscope or an accelerometer, and a microphone, whether internally or externally. The energy cell or the set of energy cells may be charged or recharged by the dock D1 when the power module 700 is docked in the dock D1, as disclosed herein. The housing, the case, or the enclosure constitutes plastic, but can constitute other suitable materials. For example, the power module 700 may constitute metal, alloy, rubber, silicone, or other suitable materials, whether natural or synthetic. In some situations, the power module 700 is configured for or constituted of such materials that are safe for sterilization, which may be performed via heat, chemicals, radiation, or other suitable processes, whether before or after scoping, as disclosed herein. For example, such sterilization may occur via exposure to steam, UV light, or another form of sterilization, whether within an autoclave or another suitable apparatus. In some situations, the power module 700 is water-proof, water-tight, water-resistant, or another suitable anti-water configuration. For example, the power module 700 may be configured for use when diving in a body of water (e.g., within about 10 meters, about 25 meters, about 50 meters).

The power module 700 has a tower 702 projecting, protruding, or bulging therefrom. The tower 702 host a control panel thereon, whether physical or virtual, as disclosed herein. The tower 702 is configured (e.g., sized, shaped, constituted) to fit into the slot 510, as disclosed herein, or within the handle 602, as disclosed herein. Although the tower 702 is shown as cuboid, this shaping is not required and the tower 702 may have a shape of a cube, a sphere, a pyramid, a cone, an ovoid, or another suitable shape. In some situations, the control panel may be omitted from the tower 702 or the power module 700, in which case controls may be on the handle 504 or the handle 602, which may be powered when the power module 700 docks to the handle 504 or the handle 602, as disclosed herein. If the tower 702 is absent, then the control panel may be located on another section of the power module 700.

The cell or the set of energy cells is similar to the store of energy of the external energy store H2 of the handheld unit 100 or the handheld unit 200 and sufficiently power dense as the internal energy store H5 of the handheld unit 100 or the handheld unit 200. For example, the energy cell or the set of energy cells may be charged or recharged by the dock D1 when the power module 700 is docked in the dock D1, as disclosed herein. The processor is similar to the processor of the handheld unit 100 or the handheld unit 200. The wireless networking interface is similar to the wireless networking interface H10 of the handle H1. The gyroscope or the accelerometer is similar to the gyroscope or the accelerometer H8 of the handle H1. The microphone is similar to the microphone H11 of the handle H1.

Therefore, as shown in FIGS. 14A-14B and FIG. 18, the power module 700 has a terminal that is configured to engage (e.g., mechanically, electrically) with an interface within the handle 502 or the handle 602, similar to how the handle H1 and the scope, each as shown in FIGS. 1-11, engage with each other, as disclosed herein. As such, one the terminal and the interface engage with each other, the power module 700 is able to power and control the tip portion, as disclosed herein.

With respect to the handheld unit 500, the power module 700 is inserted into the handle 504 such that the tower 702 travels within the slot 510 until the power module 700 docks with the handle 504 for the terminal and interface to engage with each other, as disclosed herein. Once the power module 700 is docked with the handle 504 and the terminal and interface to engage with each other, since the tower 702 hosts the control panel powered by the energy cell or the set of energy cells within the power module 700, the tip portion is controllable via the control panel through the terminal and the interface, as disclosed herein. For example, when the tip portion of the tube 502 includes various sensors, camera, nozzles, as disclosed herein, the control panel on the tower 702 is able to control those via the terminal and the interface, as disclosed herein. Likewise, since the handle 504 hosts an input element 506 (e.g., a dial, a knob, a button, a switch, a lever) and internally hosts as set of guide wires (or lines) connected to the input element 506, similar to what is disclosed in context of FIGS. 1 and 7-11, the input element 506 is configured to steer the tube 502 or the tip portion of the tube 502, as disclosed herein. When the tip portion of the tube 502 includes the opening or the nozzle for the guide SER9 guiding the instrument, as disclosed herein, the handle 504 may have the channel 508 disposed therein and configured for conveying the guide SER9 or the instrument. Although the channel 508 is shown on the bottom side of the handle 504, this configuration is not required and the channel 508 can be located on the top side of the handle 504 or laterally on the handle 504.

As shown in FIGS. 14A-14B and FIG. 18, the handle 504 has the channel 510, where the power module 700 has the tower 702, where the tower 702 hosts the control panel for the scope, where the tower 702 extends within the channel 510 when the power module 700 is assembled with the handle 504 by the user. The channel 510 has an open end section, where the tower 702 enters the channel 510 from the open end section when the power module 700 is assembled with the handle 504 by the user, where the tower 702 exits the channel 510 from the open end section when the power module 700 is disassembled from the handle 504 by the user. The channel 510 may have a U-shape, a C-shape, or a V-shape. The power module 700 may host the energy cell, the processor, and the wireless communication interface, where the wireless communication interface of the computing terminal 300 receives the imagery of the cavity captured via the scope powered by the energy cell of the power module 700 and controlled by the processor of the power module 700 when the scope extends within the cavity as the user holds the handle 504 outside the cavity. The power module 700 may host a gyroscope or an accelerometer, where the energy cell powers the gyroscope or the accelerometer such that a horizon is maintained when the handheld unit 500 is rotated or tilted. The power module 700 may host a microphone, where the wireless interface of the computing terminal 300 receives an audio content from the user captured via the microphone powered by the energy cell of the power module 700 and controlled by the processor of the power module 700 when the scope extends within the cavity as the user holds the handle 504 outside the cavity, where the audio content relates to the imagery of the cavity. The scope 500 may have a tip portion distal to the handle 504, wherein the handheld unit 500 has the passage 508 extending within the handle 504 and the tip portion through which an output of a subject matter into the cavity or an input of the subject matter from the cavity is enabled when the scope extends within the cavity as the user holds the handle outside 504 the cavity. The output of the subject matter into the cavity or the input of the subject matter from cavity may be enabled via a device, where the device includes a pump unit, an actuator unit, a motor unit, a pneumatic unit, a hydraulic unit, a pulley unit, a spool unit, a reel unit, or a winch unit, whether the handheld unit 500 hosts the device or the device is positioned off the handheld unit 500.

With respect to the handheld unit 600, note that the power module 700 have the tower 702 or may lack the tower 702. As such, the handle 602 may be adapted accordingly to fit such corresponding structure. For example, as shown in FIGS. 17A-17B, the control panel on the power module 700, where the tower 702 is lacking, may be positioned under the control panel of the handle 602 such that the control panel of the handle 602 controls the control panel of the power module 700 when the power module 700 is docked within the handle 602 to enable the terminal and the interface to engage with each other to control the tip portion. Note that data, such as imagery, controls, and other data types, may be communicated via the terminal of the power module 700 engaging the interface of the handle 600, as disclosed herein.

As shown in FIGS. 14A-14B, and FIG. 18, the handle 602 may have a compartment and a door such that the handle enables a clamshell form factor, where the compartment stores the power module 700 as the wireless communication interface of the computing terminal 300 receives the imagery of the cavity captured via the scope powered by the energy module 700 when the scope extends within the cavity as the user holds the handle 602 outside the cavity, where the power module is insertable into the compartment when the door is open and removable from the compartment when the door is open. The power module 700 may host the energy cell, the processor, and the wireless communication interface, wherein the wireless communication interface of the computing terminal 300 receives the imagery of the cavity captured via the scope powered by the energy cell of the power module 700 and controlled by the processor of the power module 700 when the scope extends within the cavity as the user holds the handle 600 outside the cavity. The power module may host the gyroscope or the accelerometer, where the power module is configured to power the gyroscope or the accelerometer such that a horizon is maintained when the handheld unit 600 or the handle 602 is rotated or tilted. The power module 700 may host the microphone, where the wireless interface of the computing terminal 300 receives an audio content from the user captured via the microphone powered by the energy cell of the power module 700 and controlled by the processor of the power module 700 when the scope extends within the cavity as the user holds the handle 600 outside the cavity, where the audio content relates to the imagery of the cavity. The scope may have a tip portion distal to the handle 602, where the handheld unit 600 has a passage extending within the handle 602, its tube and the tip portion through which an output of a subject matter into the cavity or an input of the subject matter from the cavity is enabled when the scope extends within the cavity as the user holds the handle 602 outside the cavity. The handle 602 may include a control panel for the user to control the scope, where the power module 700 is configured to power the control panel as the wireless communication interface of the computing terminal 300 receives the imagery of the cavity captured via the scope powered by the power module 700 when the scope extends within the cavity as the user holds the handle 602 outside the cavity.

As shown in FIG. 18, the handheld unit 500 or the handheld unit 600 are operated similarly to the handheld unit 100 or the handheld unit 200, as disclosed herein. However, unlike the handheld 100 or the handheld unit 200 wirelessly communicating with the computing terminal from the handle H1, the handheld unit 500 or the handheld unit 600 communicate with the computing terminal from the power module 700, as disclosed herein. Note that the external energy store H2, the internal energy store H5, or the power module 700 may host a wirelessly power receiver, whether of induction type or far-field power type (e.g., radio, line-of-sight, infrared, laser, acoustic).

Figure 19B:
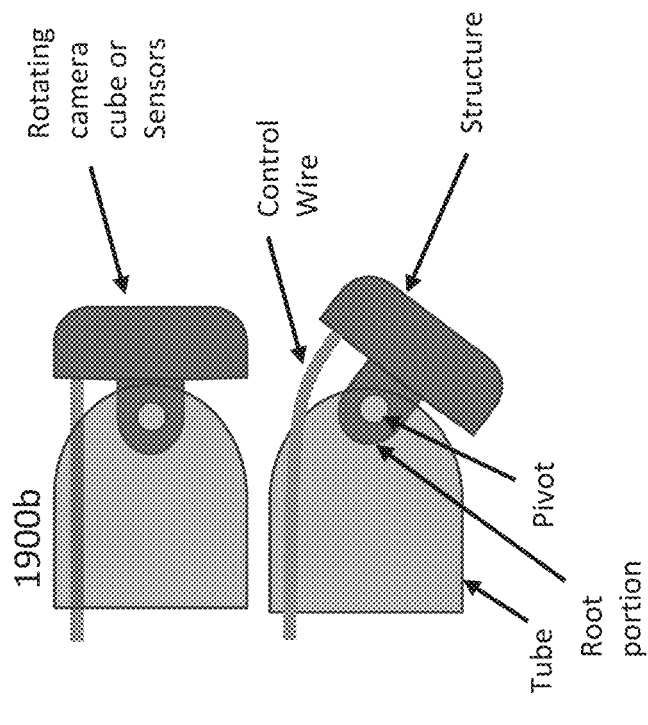
FIGS. 19A-19B shows a schematic diagram of an embodiment of a scope having an end portion that is movable according to this disclosure.
Figure 19A:
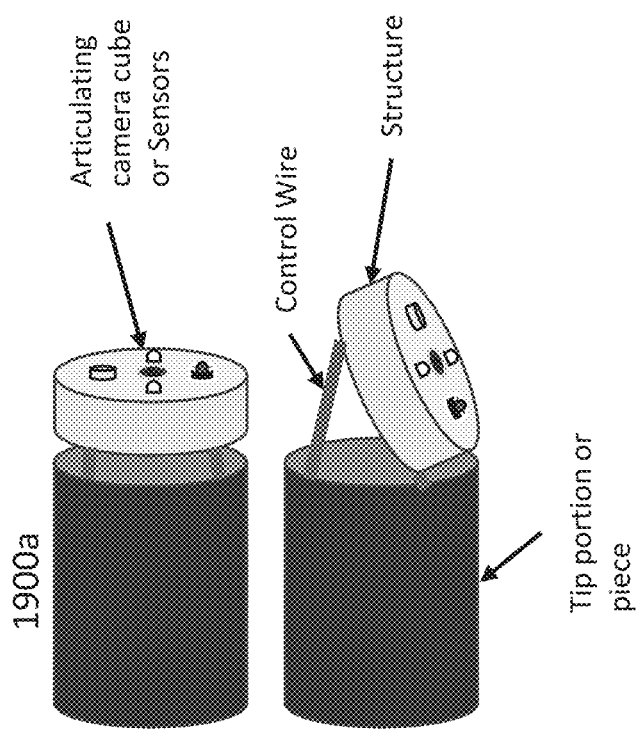
Figures 20A, 20B, 20C, 20D:
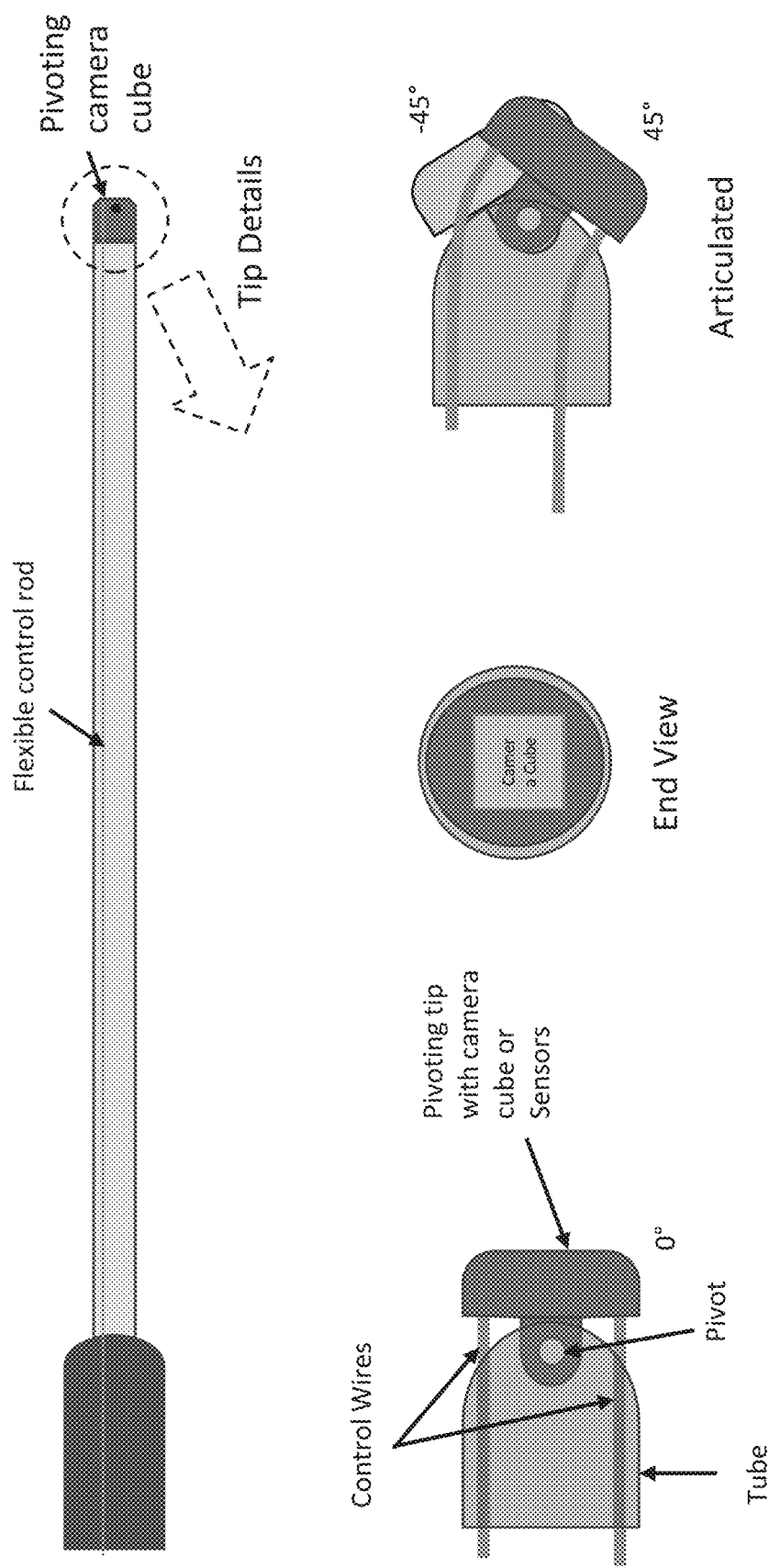
FIGS. 20A-20D show a schematic diagram of an embodiment of a scope having an end portion that is pivotable according to this disclosure.

FIGS. 19A-19B show a schematic diagram of an embodiment of a scope having an end portion that is movable according to this disclosure. In particular, there are a scope 1900a and a scope 1900b, which differ from each other in terms of how an end portion, which may be a tip portion or vice versa, is movable. Otherwise, the scope 1900a or the scope 1900b may be configured like any other scopes disclosed herein.

Each of the scope 1900a and the scope 1900b has a tip portion (or a piece) having an end portion distal to a handle, as disclosed herein. The end portion may be movable (e.g., articulatable, pivotable, swingable, rotatable, spinnable) relative to the scope. The end portion may host a camera, a sensor, a nozzle, or an opening for an instrument or a tool, as disclosed herein. The scope may host a line, as disclosed herein, contacting the end portion to enable the end portion to be movable by pushing, pulling, rotating, spinning, or twisting the line, as disclosed herein. Although the scope 1900b may have a single line, this configuration is not required. As such, the line may be a first line, and the scope 1900a may host a second line contacting the end portion to hold the end portion, as per the scope 1900a. The scope 1900a may internally host the first line and the second line parallel to each other, although this configuration is not required. Although the end portion of the scope 1900a is shown to pivot downward, this configuration is not limiting or required. For example, the end portion of the scope 1900a can pivot upward if the first line and the second line reversed in extension or when a handle, a scope, or a handheld unit, each as disclosed herein, are rotated or spun (clockwise or counterclockwise like a screwdriver).

Whether the scope 1900a or the scope 1900b, the end portion may be a plate hosting the camera, the sensor, the nozzle, or the opening for the instrument or the tool, as disclosed herein. The plate may be a disc or another suitable form factor. The scope 1900b may have the end portion including a root portion that is movable. For example, the end portion may include a structure (e.g., a plate) and a pivot (e.g., a shaft, a pin) about which the structure is pivotable, where the structure hosts the camera, the sensor, the nozzle, or the opening for the instrument or the tool, as disclosed herein. The structure may include the root portion through which the pivot extends. As such, the structure and the root portion may appear as a T-shape or a mushroom shape, when viewed from a profile view. Although the end portion of the scope 1900b is shown to pivot downward, this configuration is not limited or required. For example, the end portion of the scope 1900a can pivot upward if the line pulls inward or when a handle, a scope, or a handheld unit, each as disclosed herein, are rotated or spun (clockwise or counterclockwise like a screwdriver).

Whether the scope 1900a or the scope 1900b, the end portion is movable to enable a Field of View (FoV) to be angled, whether the scope 1900a or the scope 1900b is rigid (e.g., unable to be manually bent without usage of any tools) or flexible. This movement may be mechanical where an actuator (or a motor (e.g., electric, brushed, brushless)) is operated to articulate, spin, pivot or rotate the end portion (e.g., camera cube: CMOS and LED), as disclosed herein. For example, this movement may be mechanically inducted by a line, such as a wire, a rod, a cable, a rope, or a braid, or other form mechanical actuation. Further, this movement may enable a range of FoV, such as about 0 degrees to about 70 degrees range, although the range of FoV may be higher or lower as needed or appropriate. Although end portion may host the camera, the sensor, the nozzle, or the opening for the instrument or the tool, this configuration is not required and at least one of foregoing may be omitted. Likewise, although the range of FoV may be mechanically inducted, this configuration is not required and a software (e.g., a firmware, an application program running locally on a computing terminal or remotely in a cloud application) may be programmed to have an image FoV adjusted using CMOS (or other suitable technology) configuration and other software (local or remote). Note that when a handle, a scope, or a handheld unit, each as disclosed herein, are rotated or spun (clockwise or counterclockwise like a screwdriver), such as by the user, then FoV may change, regardless of how provided.

FIGS. 20A-20D show a schematic diagram of an embodiment of a scope having an end portion that is pivotable according to this disclosure. In particular, there is a scope 2000 which may be configured similar to the scope 1900b. However, instead of having a single line like the scope 1900b, the scope 2000 has the first line and the second line controlling movement thereof, which may enable the range of FoV to be higher than the scope 1900b. For example, the range of FoV may span between about −60 degrees and about +60 degrees, although more or less is possible.

FIGS. 21A-21D show a schematic diagram of an embodiment of a scope having an end portion that is pivotable according to this disclosure. In particular, there is a scope 2100, which may be configured similar to the scope 1900a, the scope 1900b, the scope 2000 or any other scope disclosed herein. However, the scope 2100 differs from those scopes in that the scope 2100 has a tip portion distal to a handle, as disclosed herein. The tip portion hosts a structure and a pivot (e.g., a shaft, a pin) about which the structure pivots, where the structure hosts a camera, a sensor, a nozzle, or an opening for an instrument or a tool, as disclosed herein. The structure may be a plate, such as a disc or another suitable form factor. The pivot extends through the structure such that the structure moves by a seesaw movement, as shown in FIGS. 21A-21D. The seesaw movement can be induced in various ways. For example, the seesaw movement can be induced by the scope 2100 hosting a line (e.g., a wire, a rod, a braid), as disclosed herein, contacting the structure above or below the pivot, as shown in FIGS. 21A-21D, to urge the structure to move in the seesaw movement. The seesaw movement may enable the range of FoV to be between about 0 degrees and about 70 degrees, although lower or higher FoV is possible.

The tip portion is shown to have an upper side, a lower side, and a lateral side spanning between the upper side and the lower side. The upper side may be longitudinally longer than the lower side, which enables the lateral side to be straight or curved (e.g., rounded or arcuate), which may improve the range of FoV.

FIGS. 22A-22D show a schematic diagram of an embodiment of a scope having an end portion that is pivotable according to this disclosure. In particular, there is a scope 2200, which may be configured similar to the scope 1900a, the scope 1900b, the scope 2000, the scope 2100, or any other scope disclosed herein. However, the scope 2200 differs from those scopes in that the scope 2200 has a tip portion distal to a handle, as disclosed herein. The tip portion hosts a structure and a pivot (e.g., a shaft, a pin) about which the structure pivots, where the structure hosts a camera, a sensor, a nozzle, or an opening for an instrument or a tool, as disclosed herein. The structure may be a plate, such as a disc or another suitable form factor. The pivot extends through the structure such that the structure moves by a swinging movement, as shown in FIGS. 22A-22D.

The swinging movement can be induced in various ways. For example, the seesaw movement can be induced by the scope 2200 hosting a line (e.g., a wire, a rod, a braid), as disclosed herein, contacting the structure above the pivot, as shown in FIGS. 22A-22D, to urge the structure to move in the swinging movement. The swinging movement may enable the range of FoV to be between about 0 degrees and about 70 degrees, although lower or higher FoV is possible.

FIGS. 23A-23D show a schematic diagram of an embodiment of a scope having an end portion hosting a ball and socket joint according to this disclosure. In particular, there is a scope 2300, which may be configured similar to the scope 1900a, the scope 1900b, the scope 2000, the scope 2100, the scope 2200 or any other scope disclosed herein. However, the scope 2300 differs from those scopes in that the scope 2300 has a tip portion distal to a handle, as disclosed herein. The tip portion hosts a ball-and-socket joint and a structure coupled to the ball-and-socket joint enabling the structure to move, where the structure hosts a camera, a sensor, a nozzle, or an opening for an instrument or a tool, as disclosed herein. Although the ball-and socket-joint may be motorized or actuated, this configuration is not required. As such, the ball-and socket-joint is shown to have a socket portion located within the tip portion and a ball portion located in the socket portion. The structure, which may be a plate, a disc, or another suitable form factor, is assembled or monolithic with the ball portion, whether directly, or indirectly. For example, there may be a bridge portion spanning between the ball portion and the structure to enable the structure to move, as shown in FIGS. 23A-23D. To urge the structure to move, the scope may host a line (e.g., a control wire, a rod, a cable) contacting the ball-and-socket joint or the structure to enable the structure to be movable by pushing, pulling, rotating, spinning, or twisting the line. For example, such movement may be multiplanar.

Figure 24:
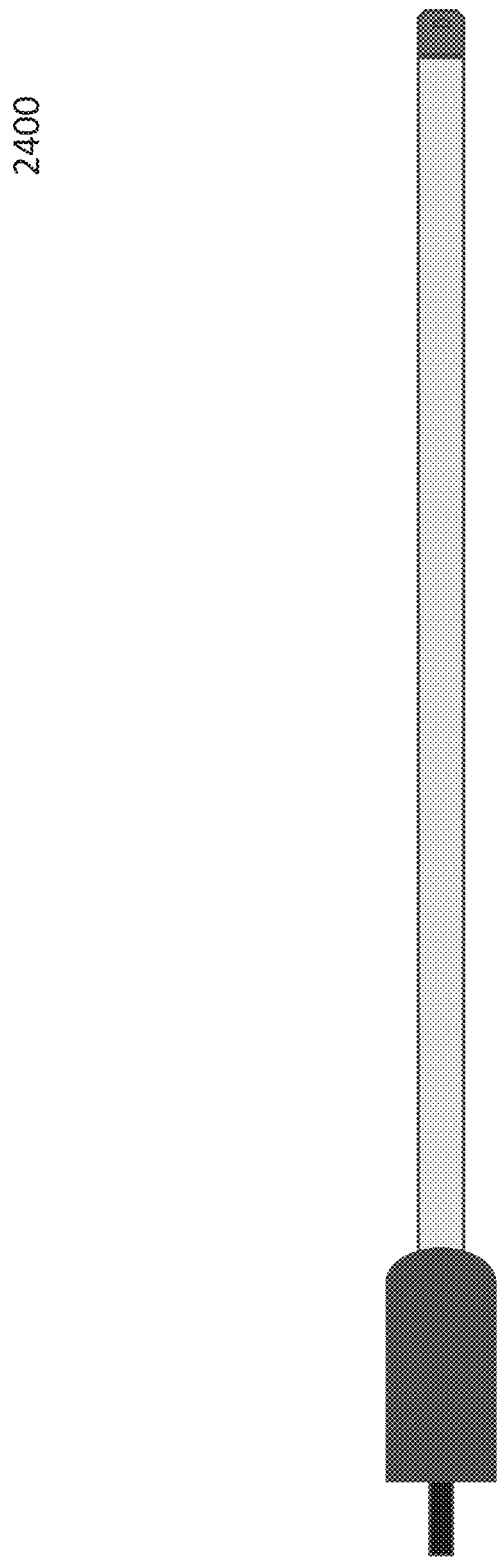
FIG. 24 shows a schematic diagram of an embodiment of a scope that is reusable and rigid according to this disclosure.

FIG. 24 shows a schematic diagram of an embodiment of a scope that is reusable and rigid according to this disclosure. In particular, there is a scope 2400, which may be configured similar to any scope disclosed herein. The scope 2400 may have a chip-on-tip configuration of all suitable diameters and lengths. The scope 2400 may have a multi-lumen configuration, which may be an extruded tube of rigid (e.g., unable to be manually bent without usage of any tools) plastic (or another suitable material) for shaft. The scope 2400 could include solid wires bonded in lumens for added stiffness. The scope 2400 may be point of use sterilizable. The scope 2400 may host a CMOS Sensor and LED on tip, as disclosed herein, although many suitable CMOS and LED options are possible. The scope 2400 may be powered and controlled by a handle, as disclosed herein, or may have proximal end mechanical and electrical interfaces.

Figure 26A:
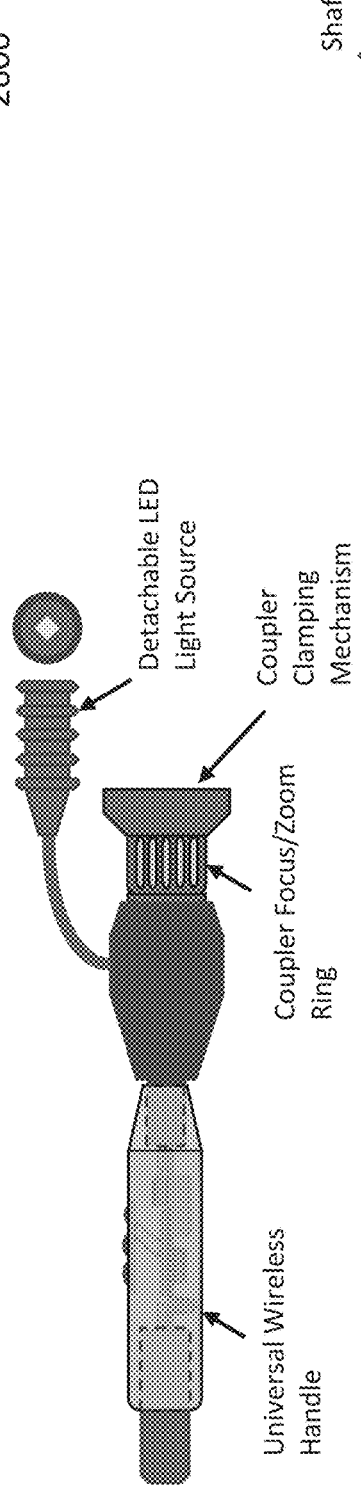
FIGS. 26A-26C show a schematic diagram of an embodiment of an adapter engaging with a handle and an endoscope according to this disclosure.
Figure 26B:
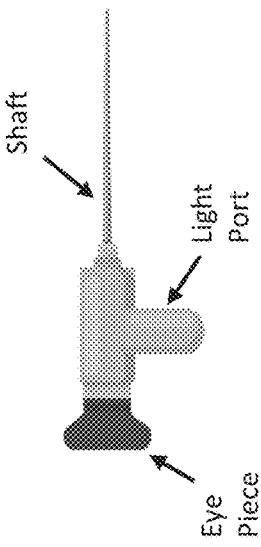
Figure 26C:
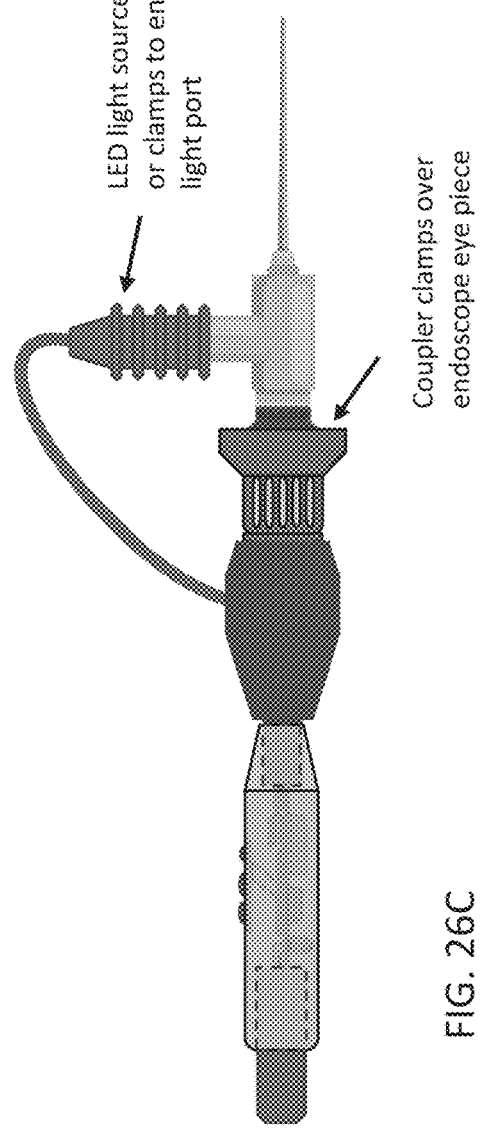

FIGS. 25A-25E show a schematic diagram of an embodiment of a handle engaging an adapter engageable with an endoscope according to this disclosure. FIGS. 26A-26C shows a schematic diagram of an embodiment of an adapter engaging with a handle and an endoscope according to this disclosure. In particular, there a system 2500 including an adapter, a coupler, and a light source. The system 2500 may be similar in function, operation, or constituency as to what is disclosed in U.S. Pat. No. 11,723,514 and U.S. Pat. No. 11,864,730, each incorporated by reference herein for all purposes. Any handle disclosed herein can work with or adapted to work with the system 2500.

The adapter, which may be embodied as a housing, a tubular member, or another suitable form factor, may be an analog adapter hosting (e.g., internally) a CMOS structure or any other relevant structure. The adapter may have a first end portion and a second end portion, where the first end portion hosts an interface (e.g., a USB plug) engageable (e.g., attachable, connectable), whether mechanically or electrically, with a handle, as disclosed herein. The second portion has an open end portion (e.g., a cavity) configured to receive the coupler, as shown in FIGS. 25A-25E, for secure attachment thereto. The adapter may constitute plastic, although other suitable materials are possible (e.g., rubber, metal).

The coupler, which may be embodied as a housing, a tubular member, or another suitable form factor, may include a first portion, a second portion, and a third portion, where the second portion may be interposed between the first portion and the second portion, whether assembled or monolithic therewith. The first portion of the coupler may be configured for insertion into the second portion of the adapter, to be positioned therein. For example, such insertion may include a mechanical connection, such as by fastening, mating, magnetizing, adhering, interlocking, or other suitable mechanical connections. The second portion may host a focus ring, which may be movable (e.g., rotatable, spinnable) relative to the second portion about the second portion, to improve an optical focus of an endoscope, as disclosed herein. The third portion may host a clamp configured to clamp an eyepiece of an endoscope, as disclosed herein. The third portion may be wider than each of the first portion and the second portion.

The light source, which may be embodied as a housing, a tubular member, or another suitable form factor, hosts an illumination source (e.g., a bulb, a diode, an incandescent bulb, an LED, a gas discharge lamp, a set of LEDs) that is configured to source a light into a light port of an endoscope, as disclosed herein.

There may be a tether (e.g., a cable, a power line) spanning between the light source and the adapter, whether the first portion or the second portion thereof, to conduct an electrical energy from an energy store of a handle to the light source, as disclosed herein, thereby enabling the light source to source the light into the light port. The tether may have a first end portion extending from the light source and a second end portion extending from the adapter, whether the first portion or the second portion thereof. The first end portion of the tether may be selectively attachable or detachable from the light source, although this configuration is not required and may be omitted (e.g., not attachable, not detachable, monolithic). The second end portion of the tether may be selectively attachable to or detachable from the adapter, whether the first portion or the second portion thereof, although this configuration is not required and may be omitted (e.g., not attachable, not detachable, monolithic).

As such, the adapter may be attachable to the handle, and the coupler may be have the first portion and the second portion, where the first portion is engageable with the adapter when the adapter is attached to the handle, and the second portion is engageable with the eyepiece of the endoscope when the adapter is attached to the handle. The light source may be configured to source the light into the light port of the endoscope when the adapter is attached to the handle and the second portion is engaged with the eyepiece, where the light source is powered by the energy store. The tether may span between the light source and the adapter, where the tether is detachable from the adapter or the light source, where the light source is powered by the energy store through the tether.

Figure 27:
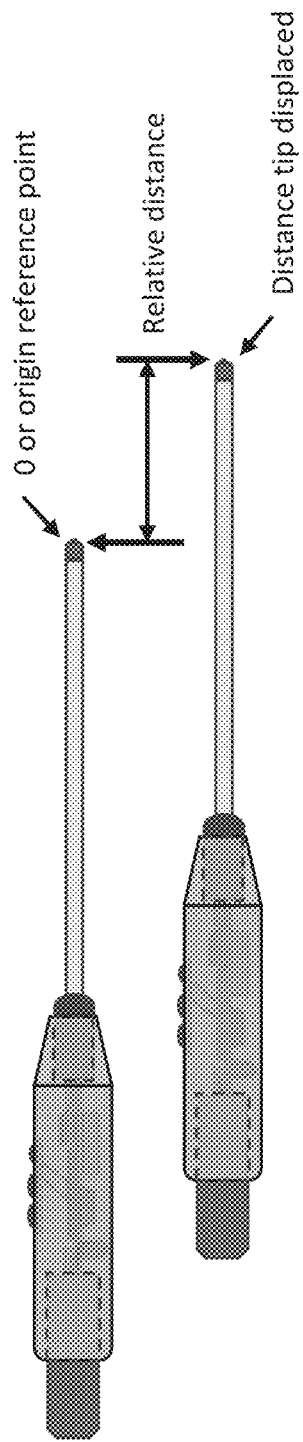
FIG. 27 shows a schematic diagram of an embodiment of a handheld unit configured for determining a relative distance awareness function according to this disclosure.
Figure 30A:
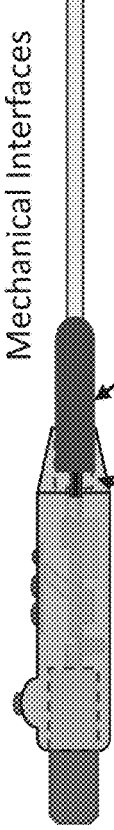
FIGS. 30A-30D show a schematic diagram of an embodiment of a handheld unit with a set of interfaces according to this disclosure.
Figure 30B:
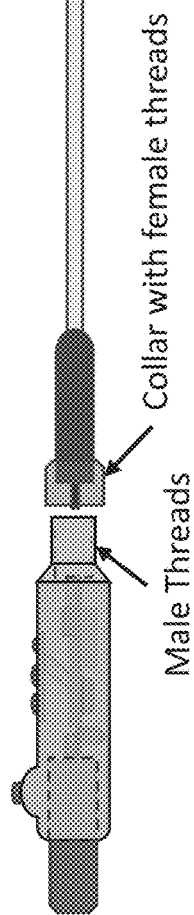
Figure 30C:
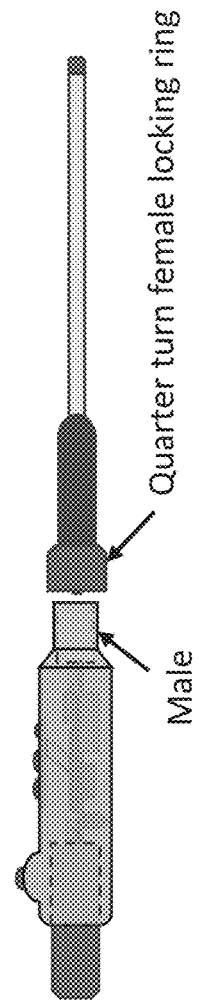
Figure 30D:
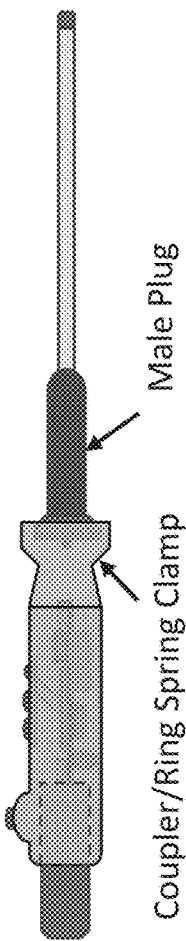

FIG. 27 shows a schematic diagram of an embodiment of a handheld unit configured for determining a relative distance awareness function according to this disclosure. In particular, there is a handheld unit 2700, which can be configured as any handheld unit disclosed herein. The handheld unit 2700 may include a scope with a tip portion. The handheld unit 2700 hosts a motion displacement sensor (e.g., an accelerometer, a gyroscope) enabled to facilitate a detection of a relative distance of displacement of the tip portion from an origin point as indicated (e.g., set) by the user, as disclosed herein. For example, the handheld unit may include a handle hosting the motion displacement sensor. The handle may host a user input device (e.g., physical, virtual, touchscreen, button, joystick, switch) for the user to operate to set (e.g., select) the origin point. The scope may be rigid, although the scope may be flexible. The relative distance of displacement may be along a horizontal plane, a vertical plane, or a diagonal plane. For example, the user can select an arbitrary zero point (tip location). Then, at least some tip displacement can be calculated by interpretation of accelerometer data over limited distances. For example, such relative distance can be used in a UroLift procedure, which may be used for diagnosis or therapy of Benign Prostatic Hyperplasia (BPH) or other medical conditions disclosed herein. For example, there may be a set of clips is installed that hold a wall of a bladder open. The set of clips is placed at a distance (e.g., about or within two or three centimeters) from an opening of a neck of the bladder. The tip portion may be placed in the neck and the origin point may be set (e.g., zero the accelerometer). Then, there may be a detection (e.g., local to handle) when the tip portion has then moved the distance (e.g., about or within two or three centimeters) into the bladder. Then, the user knows an approximate location of the tip portion and can place (e.g., secure) the set of clips as needed.

FIGS. 28A-28B show a schematic diagram of an embodiment of a handheld unit with an interface according to this disclosure. FIGS. 29A-29D show a schematic diagram of an embodiment of a handheld unit with a set of interfaces according to this disclosure. FIGS. 30A-30D show a schematic diagram of an embodiment of a handheld unit with a set of interfaces according to this disclosure. FIGS. 31A-31D show a schematic diagram of an embodiment of a handheld unit with a set of interfaces according to this disclosure. In particular, there is a handheld unit 2800, which can be configured as any handheld unit disclosed herein. The handheld unit 2800 includes a handle and a scope coupled to the handle, whether mechanically or electrically, as disclosed herein. The scope may have a tip portion, as disclosed herein. As shown in FIGS. 28A-28B, the handle may be reusable, although single use is possible. Likewise, the handle may host or grant access to a user input device (e.g., physical, virtual, joystick, button, switch, lever, dial, knob), depending on where the user input device is positioned, as disclosed herein. Similarly, the scope may be single use, although the scope may be reusable.

There may be various electrical interfaces and/or mechanical interfaces used to couple the cope attachment to the handle or control the tip portion. For example, there could be levers, pulleys, push rods, wires or other mechanical actuators and connections. Likewise, there could be a Universal Serial Bus (USB) interface, a Circular Plastic Connector (CPC) interface, inductive contacts or other force contacts for electrical connection.

As shown in 29A-29D, the handle and the scope may engage with each other via a USB interface, whether A-type, C-type, micro-type, or other suitable types, regardless of whether handle or the scope hosts a male interface portion or a female interface portion. Further, 29A-29D show the handle and the scope engage with each other via a mating interface (e.g., pins and receptacles), regardless of whether handle or the scope hosts a male interface portion or a female interface portion. Similarly, 29A-29D show the handle and the scope engage with each other via a pin (e.g., spring) and a contact (e.g., flat). Likewise, 29A-29D show the handle and the scope engage with each other via an inductive contact interface.

As shown in FIGS. 30A-30D, the handle and the scope engage with each other via a male plug and a female receptacle, regardless of whether handle or the scope hosts a male plug or a female receptacle. Further, FIGS. 30A-30D show the handle and the scope engage with each other via a threading interface (e.g., a threaded collar), regardless of whether handle or the scope hosts which threading section. Similarly, FIGS. 30A-30D show the handle and the scope engage with each other via a twist lock interface (e.g., a quarter turn female locking ring). Likewise, FIGS. 30A-30D show the handle and the scope engage with each other via a clamp ring interface (e.g., a spring clamp and a plug), regardless of whether handle or the scope hosts which section.

As shown in FIGS. 31A-31D, when the handle hosts a first line and the scope hosts a second line, there may be an intermediary mechanism, adapter, or a structure that enables the first line to engage the second line or vice versa, although a direction connection between the first line and the second line is possible to enable control thereby. As such, the handle may host a user input unit (e.g., physical, virtual, joystick, button, switch, lever) and the first line, where the scope has a tip portion distal to the handle, and the scope hosts the second line. Therefore, the tip portion may be controllable by the user input unit via the first line engaging the second line or vice versa. Such engagement may occur in various ways. For example, the tip portion may be controllable by the user input unit via the first line engaging the second line or vice versa via a mechanism including a ball end and a ferule engaging with each other, where the ball end may be capture in the ferule upon a push connection and the ball end can be disconnected with greater than typical tip actuation force. Likewise, the tip portion may be controllable by the user input unit via the first line engaging the second line or vice versa via a mechanism including a hook and a loop engaging with each other, where the hook may be rotated into the loop with a twist lock type connection, and the hook or the loop may be disconnected from each other with a twist lock disconnect. Similarly, the tip portion may be controllable by the user input unit via the first line engaging the second line or vice versa via a mechanism including a rod and a socket engaging with each other, where the rod may have an end portion forced into the socket upon a first tip actuation.

All handheld units disclosed herein may be used to perform or assist in performance of a procedure when the scope extends within a cavity of a patient as the handle is held by the user. For example, the procedure may be used to prevent, diagnose, monitor, ameliorate, or treat a neurological condition, such as epilepsy, headache/migraine, whether primary or secondary, whether cluster or tension, neuralgia, seizures, vertigo, dizziness, concussion, aneurysm, palsy, Parkinson's disease, Alzheimer's disease, or others, as understood to skilled artisans and which are only omitted here for brevity. For example, the procedure, as disclosed herein, may be used to prevent, diagnose, monitor, ameliorate, or treat a neurodegenerative disease, such as Alzheimer's disease, Parkinson's disease, multiple sclerosis, post-operative cognitive dysfunction, and postoperative delirium, or others, as understood to skilled artisans and which are only omitted here for brevity. For example, the procedure, as disclosed herein, may be used to prevent, diagnose, monitor, ameliorate, or treat an inflammatory disease or disorder, such as Alzheimer's disease, ankylosing spondylitis, arthritis (osteoarthritis, rheumatoid arthritis (RA), Sjogren's syndrome, temporal arteritis, Type 2 diabetes, psoriatic arthritis, asthma, atherosclerosis, Crohn's disease, colitis, dermatitis, diverticulitis, fibromyalgia, hepatitis, irritable bowel syndrome (IBS), systemic lupus erythematosus (SLE), nephritis, fibromyalgia, Celiac disease, Parkinson's disease, ulcerative colitis, chronic peptic ulcer, tuberculosis, periodontitis, sinusitis, hepatitis, Graves disease, psoriasis, pernicious anemia (PA), peripheral neuropathy, lupus or others, as understood to skilled artisans and which are only omitted here for brevity. For example, the procedure, as disclosed herein, may be used to prevent, diagnose, monitor, ameliorate, or treat a gastrointestinal condition, such as ileus, irritable bowel syndrome, Crohn's disease, ulcerative colitis, diverticulitis, gastroesophageal reflux disease, or others, as understood to skilled artisans and which are only omitted here for brevity. For example, the procedure, as disclosed herein, may be used to prevent, diagnose, monitor, ameliorate, or treat a bronchial disorder, such as asthma, bronchitis, pneumonia, or others, as understood to skilled artisans and which are only omitted here for brevity. For example, the procedure, as disclosed herein, may be used to prevent, diagnose, monitor, ameliorate, or treat a coronary artery disease, heart attack, arrhythmia, cardiomyopathy, or others, as understood to skilled artisans and which are only omitted here for brevity. For example, the procedure, as disclosed herein, may be used to prevent, diagnose, monitor, ameliorate, or treat a urinary disorder, such as urinary incontinence, urinalysis, overactive bladder, or others, as understood to skilled artisans and which are only omitted here for brevity. For example, the procedure, as disclosed herein, may be used to prevent, diagnose, monitor, ameliorate, or treat eat a cancer, such as bladder cancer, breast cancer, prostate cancer, lung cancer, colon or rectal cancer, skin cancer, thyroid cancer, brain cancer, leukemia, liver cancer, lymphoma, pancreatic cancer, or others, as understood to skilled artisans and which are only omitted here for brevity. For example, the procedure, as disclosed herein, may be used to prevent, diagnose, monitor, ameliorate, or treat a metabolic disorder, such as diabetes (type 1, type 2, or gestational), Gaucher's disease, sick cell anemia, cystic fibrosis, hemochromatosis, or others, as understood to skilled artisans and which are only omitted here for brevity. For example, the procedure, as disclosed herein, may be used to prevent, diagnose, monitor, ameliorate, or treat a urologic disorder, such BPH, kidney stones, enlarged prostate, or others, as understood to skilled artisans and which are only omitted here for brevity.

When the procedure is non-medical, all handheld devices disclosed herein may be used to perform or assist in performance of a procedure when the scope extends within a cavity of a non-patient or an inanimate object. For example, the non-medical procedure may be used for visual inspection work where the target area is inaccessible by other means, or where accessibility may require destructive, time consuming and/or expensive dismounting activities. For example, the non-medical endoscopic procedure may be used for in nondestructive testing techniques for recognizing defects or imperfections (e.g., the visual inspection of aircraft engines, gas turbines, steam turbines, diesel engines, automotive engines, truck engines, machined or cast parts, surface finishes, complete through-holes, military applications, forensic applications in law enforcement, plumbing, building inspection, in gunsmithing for inspecting the interior bore of a firearm, detection or de-arming of explosive devices).

Various embodiments of the present disclosure may be implemented in a data processing system suitable for storing and/or executing program code that includes at least one processor coupled directly or indirectly to memory elements through a system bus. The memory elements include, for instance, local memory employed during actual execution of the program code, bulk storage, and cache memory which provide temporary storage of at least some program code in order to reduce the number of times code must be retrieved from bulk storage during execution.

I/O devices (including, but not limited to, keyboards, displays, pointing devices, DASD, tape, CDs, DVDs, solid state drives (SSD), thumb drives and other memory media, etc.) can be coupled to the system either directly or through intervening I/O controllers. Network adapters may also be coupled to the system to enable the data processing system to become coupled to other data processing systems or remote printers or storage devices through intervening private or public networks. Modems, cable modems, and Ethernet cards are just a few of the available types of network adapters.

This disclosure may be embodied in a system, a method, and/or a computer program product. The computer program product may include a computer readable storage medium (or media) having computer readable program instructions thereon for causing a processor to carry out aspects of the present disclosure. The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, an SSD, a mechanically encoded device such as punch-cards or raised structures in a groove having instructions recorded thereon, and any suitable combination of the foregoing.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, among others. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In various embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions. The various illustrative logical blocks, modules, circuits, and algorithm steps described in connection with the embodiments disclosed herein may be implemented as electronic hardware, computer soft-ware, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The flowchart and block diagrams in the figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Words such as "then," "next," etc. are not intended to limit the order of the steps; these words are simply used to guide the reader through the description of the methods. Although process flow diagrams may describe the operations as a sequential process, many of the operations can be performed in parallel or concurrently. In addition, the order of the operations may be re-arranged. A process may correspond to a method, a function, a procedure, a subroutine, a subprogram, etc. When a process corresponds to a function, its termination may correspond to a return of the function to the calling function or the main function.

Although various embodiments have been depicted and described in detail herein, skilled artisans know that various modifications, additions, substitutions and the like can be made without departing from this disclosure. As such, these modifications, additions, substitutions and the like are considered to be within this disclosure.

What is claimed is:

1. A system, comprising:
 a handheld unit having a handle, an energy store, a scope, and a first wireless communication interface, wherein the handle has a channel, wherein the energy store has a body and a tower extending radially from the body, wherein the tower hosts a control panel for the scope, wherein the tower extends within the channel when the energy store is assembled with the handle by a user, wherein the handle has an outer wall, wherein the outer wall has the channel, and wherein the control panel extends through the channel; and
 a computing terminal hosting a second wireless communication interface, wherein the second wireless communication interface receives an imagery of a cavity captured via the scope powered by the energy store when the scope extends within the cavity as the user holds the handle outside the cavity.

2. The system of claim 1, wherein the energy store is a first energy store, wherein the handheld unit hosts a second energy store, wherein the first energy store charges the second energy store such that the first energy store is hot-swappable from the handheld unit by the user as the second wireless communication interface receives the imagery of the cavity captured via the scope powered by the second energy store when the scope extends within the cavity as the user holds the handle outside the cavity.

3. The system of claim 1, wherein the scope is detachably attachable to the handle.

4. The system of claim 1, wherein the handle hosts a gyroscope or an accelerometer, wherein the energy store powers the gyroscope or the accelerometer such that a horizon is maintained when the handheld unit is rotated or tilted.

5. The system of claim 1, wherein the handheld unit hosts a microphone, wherein the second wireless communication interface receives an audio content from the user captured via the microphone powered by the energy store when the scope extends within the cavity as the user holds the handle outside the cavity, wherein the audio content relates to the imagery of the cavity.

6. The system of claim 1, wherein the scope includes an electrical interface, a connector, a tube, and a line, wherein the tube includes a tip portion distal to the connector, wherein the electrical interface extends from the connector, wherein the tube extends from the connector, wherein the tip portion hosts an image sensor and a light source, wherein the line extends within the tube between the electrical interface and the tip portion such that the image sensor and the light source are powered via the electrical interface, wherein the energy store powers the electrical interface when the scope extends within the cavity as the user holds the handle outside the cavity.

7. The system of claim 6, wherein the tip portion hosts a chip hosting the image sensor and the light source.

8. The system of claim 6, wherein the tube is rigid.

9. The system of claim 6, wherein the channel is a first channel, wherein the scope includes a second channel extending within the tube, wherein the second channel includes an end portion, wherein the tip portion includes the end portion, wherein the end portion is open for an output of a subject matter into the cavity or an input of the subject matter from the cavity when the scope extends within the cavity as the user holds the handle outside the cavity.

10. The system of claim 1, wherein the handle and the scope are monolithic with each other.

11. The system of claim 1, wherein the scope has a tip portion distal to the handle, wherein the tip portion hosts a sensor, a light source, and an opening, wherein the opening enables an output of a subject matter into the cavity or an input of the subject matter from the cavity when the scope extends within the cavity as the user holds the handle outside the cavity.

12. The system of claim 1, wherein the computing terminal performs an image stabilization process on the imagery received by the second wireless communication interface when the scope extends within the cavity as the user holds the handle outside the cavity and maintains a point of reference to horizon on the imagery received by the second wireless communication interface when the scope extends within the cavity as the user holds the handle outside the cavity.

13. The system of claim 1, wherein the control panel is virtual.

14. The system of claim 1, wherein the handle has a compartment and a door such that the handle enables a clamshell form factor, wherein the compartment stores the energy store as the second wireless communication interface receives the imagery of the cavity captured via the scope powered by the energy store when the scope extends within the cavity as the user holds the handle outside the cavity, wherein the energy store is insertable into the compartment when the door is open and removable from the compartment when the door is open.

15. The system of claim 1, wherein the scope is designed for a single use.

16. The system of claim 15, wherein the handle is designed for the single use.

17. The system of claim 15, wherein the handle and the scope are monolithic with each other.

18. The system of claim 1, wherein the handle and the scope are longitudinally co-aligned with each other.

19. The system of claim 1, wherein the scope has an end portion distal to the handle, wherein the end portion is movable relative to the scope, wherein the end portion hosts a camera, a sensor, a nozzle, or an opening for an instrument or a tool.

20. The system of claim 1, wherein the scope has a tip portion distal to the handle, wherein the tip portion hosts a structure and a pivot about which the structure is pivotable, wherein the structure hosts a camera, a sensor, a nozzle, or an opening for an instrument or a tool.

21. The system of claim 1, wherein the scope has a tip portion distal to the handle, wherein the tip portion hosts a ball-and-socket joint and a structure coupled to the ball-and-socket joint enabling the structure to move, wherein the structure hosts a camera, a sensor, a nozzle, or an opening for an instrument or a tool.

22. The system of claim 1, further comprising:
an adapter attachable to the handle;
a coupler having a first portion and a second portion, wherein the first portion is engageable with the adapter when the adapter is attached to the handle, wherein the second portion is engageable with an eyepiece of an endoscope when the adapter is attached to the handle; and
a light source configured to source a light into a light port of the endoscope when the adapter is attached to the handle and the second portion is engaged with the eyepiece, wherein the light source is powered by the energy store.

23. The system of claim 1, wherein the scope has a tip portion, wherein the handheld unit hosts a motion displacement sensor enabled to facilitate a detection of a relative distance of displacement of the tip portion from an origin point as indicated by the user.

24. The system of claim 1, wherein the handle and the scope engage with each other via a Universal Serial Bus (USB) interface.

25. The system of claim 1, wherein the handle and the scope engage with each other via a pin and a contact.

26. The system of claim 1, wherein the handle and the scope engage with each other via an inductive contact interface.

27. The system of claim 1, wherein the handle and the scope engage with each other via a male plug and a female receptacle.

28. The system of claim 1, wherein the handle and the scope engage with each other via a threading interface.

29. The system of claim 1, wherein the handle and the scope engage with each other via a twist lock interface.

30. The system of claim 1, wherein the handle and the scope engage with each other via a clamp ring interface.

* * * * *